US012697328B2

(12) United States Patent
Hu et al.

(10) Patent No.: US 12,697,328 B2
(45) Date of Patent: Aug. 4, 2026

(54) METHODS FOR TREATING METASTASIS WITH CATHEPSIN C INHIBITORS

(71) Applicant: Shanghai Institute of Nutrition and Health, Chinese Academy of Sciences, Shanghai (CN)

(72) Inventors: Guohong Hu, Shanghai (CN); Yansen Xiao, Shanghai (CN); Min Cong, Shanghai (CN); Chenxi Liang, Shanghai (CN)

(73) Assignee: SHANGHAI INSTITUTE OF NUTRITION AND HEALTH, CHINESE ACADEMY OF SCIENCES, Shanghai (CN)

( * ) Notice: Subject to any disclaimer, the term of this patent is extended or adjusted under 35 U.S.C. 154(b) by 676 days.

(21) Appl. No.: 18/044,430

(22) PCT Filed: Sep. 10, 2021

(86) PCT No.: PCT/CN2021/117698
§ 371 (c)(1),
(2) Date: Mar. 8, 2023

(87) PCT Pub. No.: WO2022/053019
PCT Pub. Date: Mar. 17, 2022

(65) Prior Publication Data

US 2023/0321056 A1 Oct. 12, 2023

(30) Foreign Application Priority Data

Sep. 11, 2020 (CN) ......................... 202010955820.1

(51) Int. Cl.
*A61K 31/439* (2006.01)
*A61K 31/277* (2006.01)
(Continued)

(52) U.S. Cl.
CPC .......... *A61K 31/439* (2013.01); *A61K 31/277* (2013.01); *A61K 31/4045* (2013.01);
(Continued)

(58) Field of Classification Search
None
See application file for complete search history.

(56) References Cited

U.S. PATENT DOCUMENTS 5,602,102 A 2/1997 Thiele et al.
8,889,708 B2 11/2014 Grauert et al.
(Continued)

FOREIGN PATENT DOCUMENTS

WO WO 2012/119941 A1 9/2012
WO WO 2014/091443 A1 6/2014
(Continued)

OTHER PUBLICATIONS

Tejinder et al., Targeting of cathepsin C induces autophagic dysregulation that directs ER stress mediated cellular cytotoxicity in colorectal cancer cells, Cellular Signalling, vol. 46, 2018, pp. 92-102 (Year: 2018).*

(Continued)

*Primary Examiner* — Jeffrey S Lundgren
*Assistant Examiner* — Anthony Joseph Seitz
(74) *Attorney, Agent, or Firm* — NKL Law; Bin Lu; Allen Xue

(57) ABSTRACT

Provided herein are methods for treating metastasis of a cancer with a pharmaceutical composition comprising an effective amount of a cathepsin C (CTSC) inhibitor. The CTSC inhibitor, in some embodiments, is a compound of Formula (I), or a pharmaceutically acceptable salt thereof, for example, brensocatib. The treatment methods inhibit, slow, or reverse the progression of the metastasis. In some (Continued)

embodiments, the methods further comprise reducing neutrophil infiltration and/or formation of neutrophil extracellular traps (NETs).

(I)

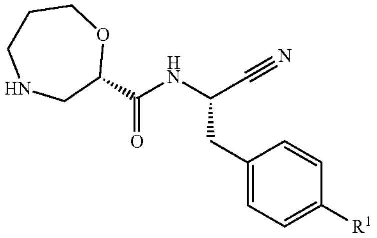

12 Claims, 34 Drawing Sheets

(51) Int. Cl.

| | |
|---|---|
| ***A61K 31/4045*** | (2006.01) |
| ***A61K 31/495*** | (2006.01) |
| ***A61K 31/496*** | (2006.01) |
| ***A61K 38/05*** | (2006.01) |
| ***A61P 35/00*** | (2006.01) |

(52) U.S. Cl.

CPC .......... *A61K 31/495* (2013.01); *A61K 31/496* (2013.01); *A61K 38/05* (2013.01); *A61P 35/00* (2018.01)

(56) References Cited

U.S. PATENT DOCUMENTS

| | | | |
|---|---|---|---|
| 8,987,249 | B2 | 3/2015 | Anderskewitz et al. |
| 8,999,975 | B2 | 4/2015 | Grundl et al. |
| 9,073,869 | B2 | 7/2015 | Anderskewitz et al. |
| 9,440,960 | B2 | 9/2016 | Grauert et al. |
| 9,522,894 | B2 | 12/2016 | Lonn et al. |
| 9,713,606 | B2 | 7/2017 | Anderskewitz et al. |
| 9,856,228 | B2 | 1/2018 | Lauritzen et al. |
| 9,879,026 | B2 | 1/2018 | Vintonyak et al. |
| 10,238,633 | B2 | 3/2019 | Anderskewitz et al. |
| RE47,636 | E | 10/2019 | Vintonyak et al. |

FOREIGN PATENT DOCUMENTS

| | | | |
|---|---|---|---|
| WO | WO 2014/140075 A1 | 9/2014 | |
| WO | WO 2015/032942 A1 | 3/2015 | |
| WO | WO 2015/032943 A1 | 3/2015 | |
| WO | WO 2015/032945 A1 | 3/2015 | |
| WO | WO-2015110826 A1 * | 7/2015 | .............. A61P 43/00 |

OTHER PUBLICATIONS

Zhang et al., IDDF2019-ABS-0160 Cathepsin C promotes tumor growth and metastasis through activating TNF-α/MAPK (p38) pathway in hepatocellular carcinoma Gut 2019;68:A55 (Year: 2019).*

Korkmaz et al., Journal of Medicinal Chemistry 2020 63 (22), 13258-13265 (Year: 2020).*

Khaket et al., Targeting of cathepsin C induces autophagic dysregulation that directs ER stress mediated cellular cytotoxicity in colorectal cancer cells. Cell Signal. Jun. 2018;46:92-102 (Year: 2018).*

Tan et al., Cathepsins mediate tumor metastasis. World J Biol Chem. Nov. 26, 2013;4(4):91-101 (Year: 2013).*

Beaumont et al., "Design of Ester Prodrugs to Enhance Oral Absorption of Poorly Permeable Compounds: Challenges to the Discovery Scientist," *Curr. Drug. Metab.*, 4, pp. 461-485 (Sharjah, U.A.E) (Nov. 2003).

Berge et al., "Pharmaceutical Salts," *J. Pharm. Sci.*, 66, pp. 1-19 (Amsterdam, The Netherlands) (Jan. 1977).

Bondebjerg et al., "Novel semicarbazide-derived inhibitors of human dipeptidyl peptidase I (hDPPI)," *Bioorg Med Chem.* 13, pp. 4008-4424 (Amsterdam, The Netherlands) (Jul. 2005).

Bondebjerg et al., "Dipeptidyl Nitriles as Human Dipeptidyl Peptidase 1 Inhibitors," *Bioorg Med Chem Lett.* 16, pp. 3614-3617 (Amsterdam, The Netherlands) (Jul. 2006).

Doyle et al., "Discovery of Second Generation Reversible Covalent DPP1 Inhibitors Leading to an Oxazepane Amidoacetonitrile Based Clinical Candidate (AZD7986)," *J. Med. Chem.* 59, pp. 9457-9472 (Washington, DC, US) (Oct. 2016).

International Search Report dated Dec. 8, 2021 issued in Int'l Appln. PCT/CN2021/117698.

Khaket et al., "Targeting of cathepsin C induces autophagic dysregulation that directs ER stress mediated cellular cytotoxicity in colorectal cancer cells," *Cellular Signalling* 46, pp. 92-102 (Amsterdam, The Netherlands) (Jun. 2018).

Kessenbrock et al., "Netting neutrophils in autoimmune small-vessel vasculitis," *Nat. Med.* 15(6), pp. 623-625 (electronic publication) (Jun. 2009).

Kolackzkowska et al., "Molecular Mechanisms of NET formation and degradation revealed by intravital imaging in the liver vasculature," *Nat. Commum.* 6, 6673 (New York, NY, US) (2015).

Korkmaz et al., "Neutrophil proteinase 3 and dipeptidyl peptidase I (cathepsin C) as pharmacological targets in granulomatosis with polyangiitis (Wegener granulomatosis)," *Semin. Immunopathol.* 35(4), pp. 411-421 (electronic publication) (Feb. 2013).

Rautio et al., "Prodrugs: design and clinical applications," *Nature Reviews Drug Discovery* 7, pp. 255-270 (London, England, UK) (Mar. 2008).

Stahl et al. "Handbook of Pharmaceutical Salts: Properties, selection and use," *Chemistry International*, 24(3), pp. 20-21 (Berlin, Germany) (2002).

Suski et al., "Isolation of plasma membrane-associated membranes from rat liver," *Nat. Protoc.* 9, pp. 312-322 (electronic publication) (Jan. 2014).

Taylor et al., "Lysyl oxidase contributes to mechanotransduction-mediated regulation of transforming growth factor-beta signaling in breast cancer cells," *Neoplasia* 13(5), pp. 406-418 (Amsterdam, The Netherlands) (May 2011).

Teijeira et al. "CXCR1 and CXCR2 chemokine receptor agonists produced by tumors induce neutrophil extracellular traps that interfere with immune cytotoxicity," *Immunity* 52(5), pp. 856-871 e858 (Amsterdam, The Netherlands) (May 2020).

Valk et al., "Prognostically useful gene-expression profiles in acute myeloid leukemia," *N. Engl. J. Med.* 350(16), pp. 1617-1628 (Waltham, MA, US) (Apr. 2004).

Xiao et al., "Cathepsin C promotes breast cancer lung metastasis by modulating neutrophil infiltration and neutrophil extracellular trap formation," *Cancer Cell* 39(3), pp. 423-437 (Cambridge, Massachusetts, US) (Mar. 2021).

Zhang et al., "Cathepsin C Interacts with TNF-α/p38 MAPK Signaling Pathway to Promote Proliferation and Metastasis in Hepatocellular Carcinoma," *Cancer Res. Treat.*, 52(1), pp. 10-23 (Seoul, Korea) (Jan. 2020).

Zhang et al., "Neutrophil membrane-coated nanoparticles inhibit synovial inflammation and alleviate joint damage in inflammatory arthritis," *Nat. Nanotechnol* 13, pp. 1182-1190 (Baden-Wuerttemberg, Germany) (Sep. 2018).

Zhuang et al., "Differential effects on lung and bone metastasis of breast cancer by Wnt signalling inhibitor DKK1," *Nat. Cell Biol.* 19(10), pp. 1274-1285 (London, England, UK) (Oct. 2017).

* cited by examiner

METHODS FOR TREATING METASTASIS WITH CATHEPSIN C INHIBITORS

CROSS REFERENCE TO RELATED APPLICATION

This application is a national stage under 35 U.S.C. § 371 of International Application No. PCT/CN2021/117698, filed Sep. 10, 2021, wherein International Application No. PCT/CN2021/117698 claims the benefit of Chinese Patent Application No. CN202010955820.1, filed Sep. 11, 2020 and now expired, the contents of each of which are herein incorporated by reference in their entireties.

FIELD OF THE INVENTION

The present invention relates to the field of oncology, and in particular, to use of a cathepsin C inhibitor in treating tumors such as primary tumors or metastases.

BACKGROUND OF THE INVENTION

Among numerous tumors, metastasis is a main factor that causes patients to die, and 90% of deaths of tumor patient are caused by metastasis. The lung is the most common target organ for metastasis of breast cancer, and is also a place for air exchange in the human body. The occurrence of lung metastasis is a deadly threat to tumor patients.

Breast cancer is a female tumor with the highest incidence rate and mortality rate both domestically and internationally. In the triple-negative breast cancer subtype that has the worst therapeutic effect right now, lung metastasis is the main reason for treatment failure and patient death. The microenvironment regulation by tumor cells plays an important role in every step of the metastasis formation of tumor cells. A lot of research has shown that extracellular proteins secreted by tumor cells, including proteases, cytokines, growth factors, extracellular matrix proteins, and the like, play a key role in the process of regulating a tumor microenvironment by cancer cells.

As a type of important tumor microenvironment regulation molecules, proteases participate in a series of processes closely related to tumor cell metastasis. Therefore, research on how tumor-related secretory proteins, in particular secretory factors having protease activities, regulate metastasis has important biological significance and clinical application value.

Cathepsin C (CTSC) is also referred to as dipeptidyl peptidase 1 (DPP1), which was found by Gutman and Fruton in 1984. Located at chromosome 11q14.1-q14.3, CTSC is an important common protease. However, there are few reports of relevant roles played by CTSC in tumor metastasis.

Therefore, there is an urgent need to study the impact of proteases on tumor metastasis, in particular the impact of CTSC on tumor metastasis, and on the basis of this, to develop novel pharmaceutical formulations for inhibiting tumor metastasis, thereby extending the survival time and improving the survival quality of tumor patients.

SUMMARY OF THE INVENTION

The present disclosure in one aspect, relates to the use of CTSC inhibitors to treat or inhibit metastasis of a cancer or to treat a primary cancer. The cancer in one embodiment, is a breast cancer. The metastasis in one embodiment, lung metastasis of breast cancer, liver metastasis of breast cancer, bone metastasis of breast cancer, or bone metastasis of lung cancer. In a further embodiment, the metastasis is lung metastasis of a breast cancer. In another embodiment, the metastasis is of a lung cancer.

In another aspect, a method is provided for treating a metastasis of a cancer in a patient in need of treatment. The method comprises administering to the patient in need of treatment for a treatment period, a pharmaceutical composition comprising a CTSC inhibitor, wherein the treating inhibits, slows, or reverses the progression of the metastasis.

In another aspect, a method is provided for treating a primary cancer in a patient in need of treatment. The method comprises administering to the patient in need of treatment for a treatment period, a pharmaceutical composition comprising a CTSC inhibitor, wherein the treating inhibits, slows, or reverses the progression of the primary cancer.

In one embodiment, the CTSC inhibitor is brensocatib (formerly known as AZD7986), or a pharmaceutically acceptable salt thereof:

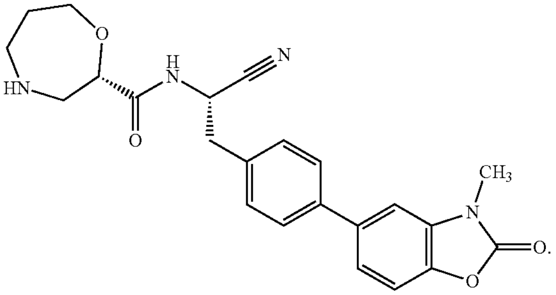 [SMILES: Cn1c(=O)oc2ccc(-c3ccc(C[C@@H](C#N)NC(=O)[C@@H]4CNCCCO4)cc3)cc21]

In yet another embodiment, the CTSC inhibitor is one of the inhibitors set forth in Table 1 herein.

In one embodiment of the methods provided herein, the method comprises administering to the patient for a treatment period, a pharmaceutical composition comprising an effective amount of a compound of Formula (I), or a pharmaceutically acceptable salt thereof:

(I)

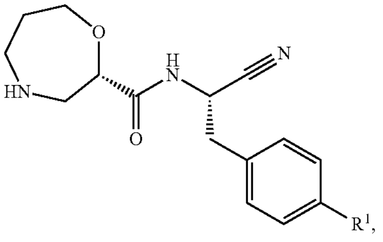

wherein, $R^1$ is

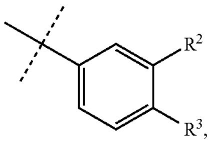

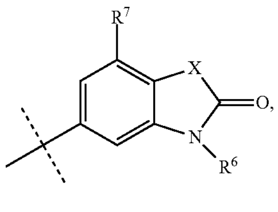

-continued

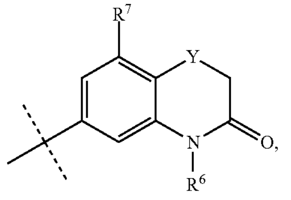

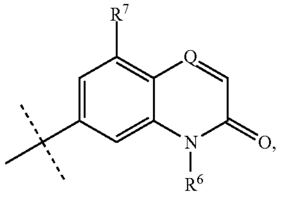

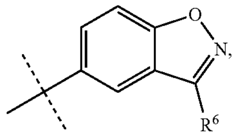

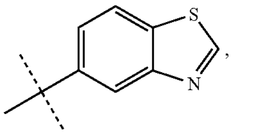

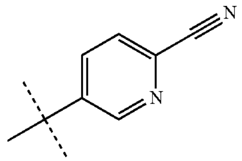

or

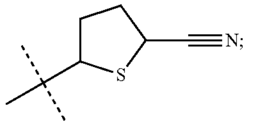

$R^2$ is hydrogen, F, Cl, Br, $OSO_2C_{1-3}$alkyl, or $C_{1-3}$alkyl;

$R^3$ is hydrogen, F, Cl, Br, CN, $CF_3$, $SO_2C_{1-3}$alkyl, $CONH_2$ or $SO_2NR^4R^5$, wherein $R^4$ and $R^5$ together with the nitrogen atom to which they are attached form an azetidine, pyrrolidine or piperidine ring;

X is O, S or $CF_2$;

Y is O or S;

Q is CH or N;

$R_6$ is $C_{1-3}$alkyl, wherein the $C_{1-3}$alkyl is optionally substituted by 1, 2 or 3 F and optionally by one substituent selected from OH, $OC_{1-3}$alkyl, $N(C_{1-3}alkyl)_2$, cyclopropyl, or tetrahydropyran; and $R^7$ is hydrogen, F, Cl or $CH_3$, wherein the treating inhibits, slows, or reverses the progression of the primary cancer or the metastasis.

In one embodiment of the method, the pharmaceutical composition comprises a compound of Formula (I), wherein $R^1$ is

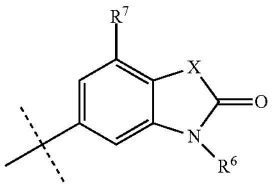

or

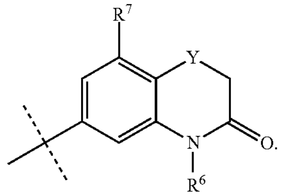

In a further embodiment, $R^1$ is

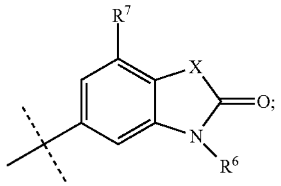

X is O, or $CF_2$; $R^6$ is $C_{1-3}$alkyl, wherein the $C_{1-3}$alkyl is optionally substituted by 1, 2 or 3 F; and $R^7$ is hydrogen, F, Cl or $CH_3$. In even a further embodiment, $R^7$ is hydrogen.

In one embodiment, the pharmaceutical composition comprises an effective amount of brensocatib.

In one embodiment of the method for treating metastasis of a cancer provided herein, the metastasis is of a breast cancer. In a further embodiment, the metastasis of a breast cancer is a lung metastasis of a breast cancer, liver metastasis of a breast cancer, bone metastasis of a breast cancer or brain metastasis of a breast cancer. In even a further embodiment, the metastasis of a breast cancer is lung metastasis of a breast cancer. The breast cancer, in one embodiment, is luminal breast cancer, human epidermal growth factor receptor 2 (HER2) positive breast cancer, or triple-negative breast cancer.

In one embodiment of the treatment of a primary cancer provided herein, the primary cancer is lung cancer, liver cancer or breast cancer. In a further embodiment, the primary cancer is breast cancer. In a further embodiment, the breast cancer is luminal breast cancer, human epidermal growth factor receptor 2 (HER2) positive breast cancer, or triple-negative breast cancer. In another embodiment, the primary cancer is liver cancer. In yet another embodiment, the primary cancer is lung cancer. In a further embodiment, the lung cancer is non-small cell lung cancer (NSCLC). In another embodiment, the lung cancer is small cell lung cancer.

In another embodiment of the method for treating metastasis of a cancer provided herein, the metastasis is a bone metastasis of lung cancer, a liver metastasis of pancreatic cancer, or a liver metastasis of gastric cancer. In yet another embodiment of the method for treating metastasis of a cancer provided herein, the metastasis is a lung metastasis of breast cancer, a liver metastasis of breast cancer, a bone metastasis of breast cancer, a brain metastasis of breast cancer, a bone metastasis of lung cancer, a liver metastasis of pancreatic cancer, a liver metastasis of colon cancer, or a liver metastasis of gastric cancer. In even another embodiment, the metastasis is of a lung cancer. In one embodiment, the metastasis is of a pancreatic cancer or a gastric cancer. In yet even another embodiment, the metastasis is of a bone cancer, liver cancer, stomach cancer or a colorectal cancer.

In one embodiment of the methods provided herein, the pharmaceutical composition is administered orally. In a further embodiment, administration is once per day during the treatment period.

The treatment period, according to some embodiments of the method provided herein, is from about 6 months to about 36 months. In a further embodiment, the treatment period is between about 6 months and about 24 months. In a further embodiment, the treatment period is between about 6 months and about 18 months. In even a further embodiment, the treatment period is between about 6 months and about 12 months. In another embodiment, the treatment period is between about 12 months and about 36 months. In even another embodiment, the treatment period is between about 18 months and about 36 months.

In one embodiment of the method for treating a primary cancer or a metastasis of a cancer provided herein, the volume of the primary cancer (primary tumor) or metastasis is reduced during the treatment period or subsequent to the treatment period, compared to the volume of the primary cancer (primary tumor) or metastasis prior to the treatment period. In a further embodiment, the volume is reduced by from about 5% to about 25%, or from about 25% to about 50% or from about 50% to about 75% during the treatment period or subsequent to the treatment period, compared to the volume prior to the treatment period.

In some embodiments of the method for treating a primary cancer or a metastasis of a cancer provided herein, the treating entails reducing circulating neutrophil extracellular traps (NETs) in in the patient during the treatment period or subsequent to the treatment period, compared to the number of circulating NETs in the patient prior to the treatment period, or as compared to the number of circulating NETs in a second patient having the same primary cancer or metastasis but not administered the pharmaceutical composition. In a further embodiment, the number of circulating NETs is reduced by at least 50% compared to the number of circulating NETs prior to the treatment period.

In yet another embodiment of the method for treating metastasis of a cancer provided herein, the method includes reducing NETs in the primary cancer (primary tumor) metastasis during the treatment period or subsequent to the treatment period, compared to the number of NETs in the primary cancer (primary tumor) or metastasis prior to the treatment period. In a further embodiment, the number of NETs in the primary cancer (primary tumor) or metastasis is reduced by at least 50% compared to the number of NETs prior to the treatment period.

In some embodiments of the method for treating a primary cancer or a metastasis of a cancer provided herein, the treating entails reducing neutrophil migration in the primary cancer or the metastasis during the treatment period or subsequent to the treatment period, as compared to the neutrophil migration prior to the treatment period, or as compared to the neutrophil migration in a second patient having the same primary cancer or metastasis but not administered the pharmaceutical composition. Neutrophil migration is reduced, in a further embodiment, by from about 25% to about 75%, by from about 25% to about 50% or by at least about 25%.

BRIEF DESCRIPTION OF THE DRAWINGS

FIG. 1 correlates CTSC protein expression to lung metastasis in clinical samples of breast cancer.

FIGS. 1B-D show fluorescence signals of the lungs after tail vein injection of CTSC overexpressing SCP28 cells in mice (B), the number of pulmonary surface metastatic nodules after tail vein injection of CTSC overexpressing SCP28 cells in mice (C), and a survival analysis of mice injected with CTSC overexpressing SCP28 cells compared to a control group of mice injected with SCP28 cells (n=10 for each group) (D).

FIG. 3 indicates that CTSC knockdown inhibits lung metastasis of breast cancer.

FIG. 4 illustrates that CTSC expression promotes lung metastasis of breast cancer in immune-complete mice.

FIG. 5 demonstrates that CTSC is involved in early stage metastatic colonization of breast cancer cells in the lungs. FIG. 5D shows reduced metastasis formation in the lungs of mice injected with LM2 cells with CTSC knocked down, while

FIG. 6 confirms that neutrophil recruitment in lung metastasis is influenced by CTSC expression levels.

FIG. 9 correlates CTSC expression to neutrophil infiltration and NET formation in clinical samples of lung metastasis of breast cancer.

FIGS. 10 B-E show that brensocatib treatment suppresses the formation of pulmonary metastatic nodules (B), reduces body weight loss (C), increases survival rates (D), and reduces neutrophil infiltration in pulmonary lesions (E) after administration of brensocatib to mice having been injected with of 4T1 cells.

FIG. 11 illustrates the ability of brensocatib to inhibit neutrophil recruitment, NETosis induction and tumor sphere formation by various metastatic cancer cells. FIG. 11K-P shows tumor sphere formation of colon cancer cells SW480 (K), lung cancer cells A549 (L), gastric cancer cells AGS (M), hepatocellular carcinoma cells HUH7 (N) and pancreatic cancer cells KP4 (O) cultured in medium of neutrophils pre-treated with CM of the cancer cells (CM), or brensocatib (Bren).

FIG. 12 illustrates the ability of brensocatib to inhibit liver primary tumor and metastasis.

DETAILED DESCRIPTION OF THE INVENTION

Figure 1A:
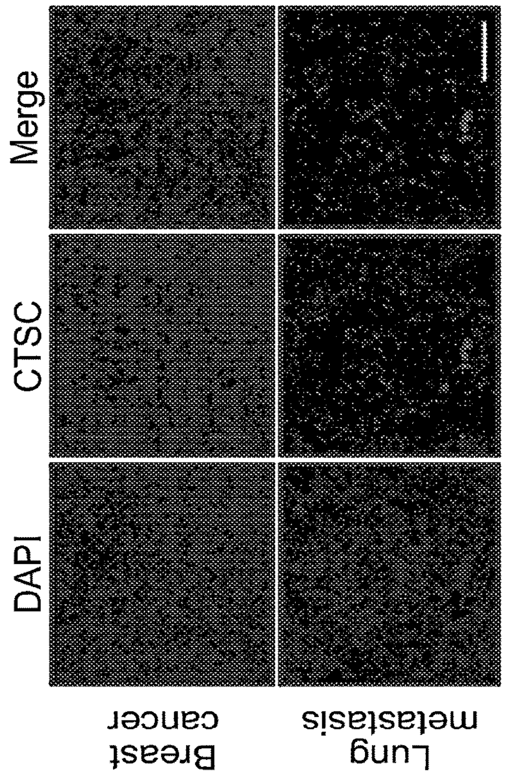
FIG. 1A shows immunofluorescence (IF) images of relative CTSC protein levels in paired primary tumors and lung metastases, and FIG. 1B plots relative CTSC protein levels in samples of primary tumors and lung metastasis lesions in pairs of 7 breast cancer patients as determined by IF, where the scale of the plot is 100 μm.

The present disclosure is based in part on the finding that CTSC promotes metastasis of breast cancer. Additionally, the present disclosure demonstrates that, by regulating neutrophil infiltration and/or formation of NETs in the metastatic microenvironment, CTSC promotes the occurrence of lung metastasis and liver metastasis on breast cancer cells, prompting the identification of pharmaceutical inhibitors of CTSC for the treatment of tumor metastases. Without wishing to be bound by theory, by inhibiting CTSC, neutrophil infiltration and formation of NETs, CTSC inhibitors regulate the tumor microenvironment of cancer to slow, reduce, or inhibit metastasis in other organs.

As such, in one aspect of the invention, a method for treating metastasis of a cancer in a patient in need of treatment is provided. The method comprises administering to the patient a pharmaceutical composition comprising an effective amount of a CTSC inhibitor. The treating inhibits, slows, or reverses the progression of the metastasis, e.g., decreases the size of the metastatic growth.

In another aspect of the invention, a method for treating a primary cancer in a patient in need of treatment is provided. The method comprises administering to the patient a pharmaceutical composition comprising an effective amount of a CTSC inhibitor. The treating inhibits, slows, or reverses the progression of the primary cancer, e.g., decreases the size of the primary tumor growth.

As used herein "cancer" refers to any malignant and/or invasive growth or tumor caused by abnormal cell growth. Cancer includes solid tumors named for the type of cells that form them, cancer of blood, bone marrow, or the lymphatic system. Examples of solid tumors include sarcomas and carcinomas. Cancer also includes primary cancer that originates at a specific site in the body, a metastatic cancer that has spread from the place in which it started to other parts of the body, a recurrence from the original primary cancer after remission, and a second primary cancer that is a new primary cancer in a person with a history of previous cancer of a different type from the latter one. A "primary cancer" or "primary tumor", as used herein, refers to the original or first cancer or tumor in a subject or patient.

As used herein, the term "metastasis" refers to a malignant growth at a different or secondary site located at a distance from a primary site of cancer where the metastasis includes cancer cells from the primary growth. For example, a "lung metastasis" refers to a secondary cancer/tumor in the lung that originated elsewhere, i.e., from a primary cancer. A "metastasis of a cancer" and "cancer metastasis" are used interchangeably herein, and refer to the secondary cancer growth at a distance from the primary cancer site.

As used herein, the term "expression" includes production of mRNA from genes or portions of genes, includes production of proteins encoded by RNA or genes or portions of genes, and includes the appearance of detection substances related to expression. For example, cDNA, the binding of a binding ligand (e.g., an antibody) with a gene or other oligonucleotides, proteins or protein fragments, and a chromogenic portion of the binding ligand all fall within the scope of the term "expression". Therefore, the increase of blot density on immunoblotting, e.g., western blotting, also falls within the scope of the term "expression" based on biological molecules.

As used herein, the term "effective amount" refers to an amount effective, at dosages and for periods of time necessary or sufficient, to achieve the desired therapeutic or prophylactic result.

As used herein, the term "treating" means reducing the frequency with which symptoms of a disease (e.g., tumor growth and/or metastasis, or other effect mediated by the numbers and/or activity of immune cells, and the like) are experienced by a patient. The term includes the administration of the compounds or agents of the present invention to prevent or delay the onset of the symptoms, complications, or biochemical indicia of a disease, alleviating the symptoms or arresting or inhibiting further development of the disease, condition, or disorder. Treatment may be prophylactic (to prevent or delay the onset of the disease, or to prevent the manifestation of clinical or subclinical symptoms thereof) or therapeutic suppression or alleviation of symptoms after the manifestation of the disease.

As used herein, the term "patient" refers to a human or animal subject. In a preferred embodiment, the patient is human.

The term "pharmaceutically acceptable", unless otherwise noted, is used to characterize a moiety (e.g., a salt, dosage form, or excipient) as being appropriate for use in accordance with sound medical judgment. In general, a pharmaceutically acceptable moiety has one or more benefits that outweigh any deleterious effect that the moiety may have. Deleterious effects may include, for example, excessive toxicity, irritation, allergic response, and other problems and complications.

As used herein, "$C_{1-3}$" means a carbon group having 1, 2 or 3 carbon atoms.

The term "alkyl", unless otherwise noted, includes both straight and branched chain alkyl groups and may be, substituted or non-substituted. "Alkyl" groups include, but are not limited to, methyl, ethyl, n-propyl, i-propyl, butyl, pentyl.

The term "and/or" when used in a list of two or more items, means that any one of the listed items can be employed by itself or in combination with any one or more of the listed items. For example, the expression "A and/or B" is intended to mean either or both of A and B, i.e., A alone, B alone, or A and B in combination. The expression "A, B and/or C" is intended to mean A alone, B alone, C alone, A and B in combination, A and C in combination, B and C in combination, or A, B, and C in combination.

As used herein, terms in the singular and the singular forms "a," "an," and "the," for example, include plural referents unless the content clearly dictates otherwise.

Where a range of values is provided, it is understood that each intervening value, between the upper and lower limit of that range and any other stated or intervening value in that stated range is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either both of those included limits are also included in the disclosure. Whenever the phrase "comprising" is used, variations such as "consisting essentially of" and "consisting of" are also contemplated.

Provided herein are methods for treating a primary cancer or a metastasis of a cancer, comprising in part, administering a pharmaceutical composition comprising an effective amount of a CTSC inhibitor to a patient in need of treatment. The treating inhibits, slows, or reverses the progression of the primary cancer or the metastasis, e.g., decreases the size of the primary tumor or the metastatic growth. CTSC, also known as dipeptidyl peptidase 1 (DPP1), is a protease and its genetic sequence is located at chromosome 11q14.1-q14.3.

CTSC has been reported to be important to serine activation expressed in immune cells. For example, CTSC can activate neutrophil elastase (NE), proteinase 3 (PR3), cathepsin G (CTSG), and neutrophil serine protease 4 (NSP4) in neutrophils, chymase and Tryptase αII/βII/γ in mast cells, and granzymes A/B in lymphocytes.

Taking the activation of NE, PR3, CTSG, and NSP4 of neutrophils by CTSC as an example, CTSC positioned by lysosome or Golgi apparatus activates three serine proteases of NE, PR3, and CTSG of neutrophils by removing two amino acids at the N-terminus, thereby playing a role of regulating inflammatory reaction. In an early phase of the neutrophil maturation process, i.e., the phases of myeloblasts and promyelocytes in morphology, NSPs are instantaneously expressed in the form of proenzymes, and dipeptides that block their own enzyme activity included at the N-termini of proenzymes of neutrophil serine proteases (NE, PR3, CTSG, and NSP4) are cleaved by CTSC during the Golgi apparatus transport process or within primary granules (azurophilic granules), and then are stored in the primary granules in an active form. However, there is also literature reporting that PR3 is constitutively expressed on a cell membrane in an inactivated state.

While CTSC plays an important role for neutrophils to have normal immune functions, the role of CTSC in metastatic cancer has not been fully elucidated. It has been found in the present disclosure that, by improving neutrophil infiltration at a lesion site and by increasing the number of NETs, CTSC improves the tumor microenvironment and promotes lung metastasis of breast cancer. As such, one aspect of the invention relates to a method for treating metastasis of a cancer in a patient in need of treatment, comprising administering to the patient a pharmaceutical composition comprising an effective amount of a CTSC inhibitor. The treating inhibits, slows, or reverses the progression of the metastasis.

The CTSC inhibitor, in one embodiment, is one of the CTSC inhibitors set forth in Table 1 or Table 2, below.

TABLE 1

| Compound | Structural formula |
|---|---|
| BI-9740 | 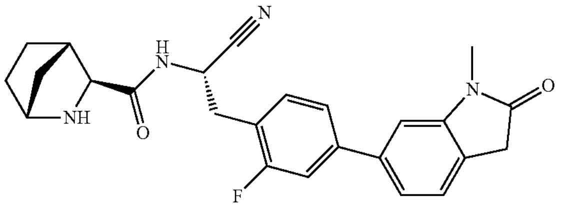 [SMILES: CN1C(=O)Cc2ccc(-c3ccc(C[C@@H](C#N)NC(=O)[C@H]4N[C@@H]5CC[C@H]4C5)c(F)c3)cc21] |
| GSK-2793660 | 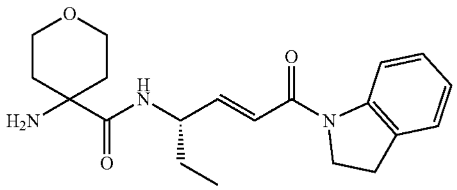 [SMILES: CC[C@@H](/C=C/C(=O)N1CCc2ccccc21)NC(=O)C1(N)CCOCC1] |
| Gly-Phe-CHN2 | 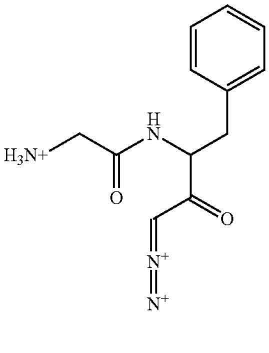 [SMILES: [NH2+]=[N+]=CC(=O)C(Cc1ccccc1)NC(=O)C[NH3+]] |

TABLE 1-continued
| Compound | Structural formula |
| --- | --- |
| IcatC$_{XPZ\text{-}01}$ | 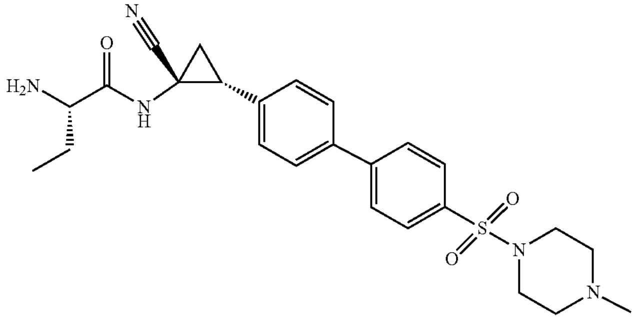 [SMILES: CC[C@H](N)C(=O)N[C@]1(C#N)C[C@@H]1c1ccc(-c2ccc(S(=O)(=O)N3CCN(C)CC3)cc2)cc1] |
| Compound 1, U.S. Pat. No. 8,877,775 | 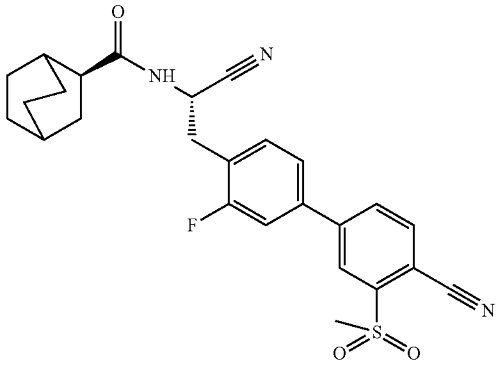 [SMILES: CS(=O)(=O)c1cc(-c2ccc(C[C@@H](C#N)NC(=O)[C@H]3CC4CCC3CC4)c(F)c2)ccc1C#N] |
| Compound 1, U.S. Pat. No. 9,440,960 B2 | 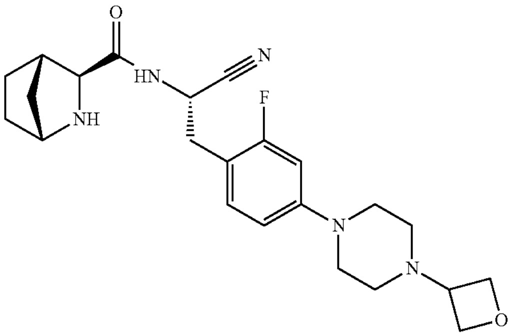 [SMILES: N#C[C@H](Cc1ccc(N2CCN(C3COC3)CC2)cc1F)NC(=O)[C@H]1N[C@@H]2CC[C@H]1C2] |
| Compound 1, U.S. Pat. No. 9,879,026 | 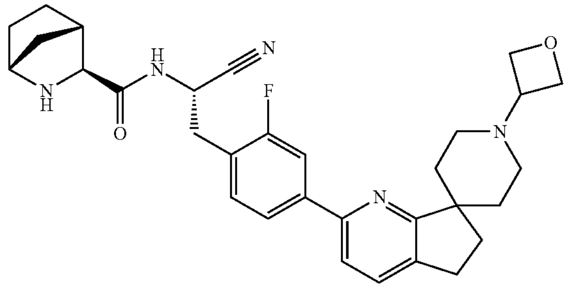 [SMILES: N#C[C@H](Cc1ccc(-c2ccc3c(n2)C2(CC3)CCN(C3COC3)CC2)cc1F)NC(=O)[C@H]1N[C@@H]2CC[C@H]1C2] |

TABLE 1-continued
| Compound | Structural formula |
|---|---|
| Compound 25, U.S. Pat. No. 9,879,026 | 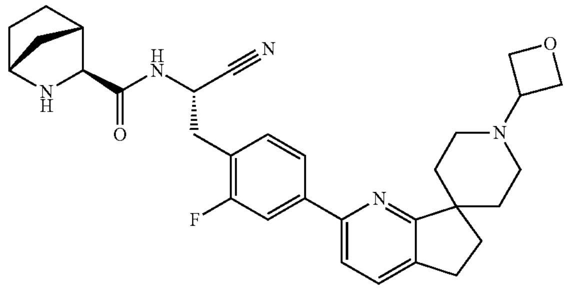 [SMILES: N#C[C@H](Cc1ccc(-c2ccc3c(n2)C2(CC3)CCN(C3COC3)CC2)cc1F)NC(=O)[C@H]1N[C@@H]2CC[C@H]1C2] |
| PZ1018 | 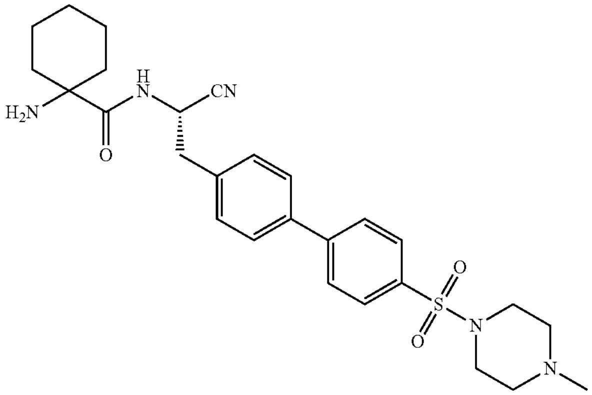 [SMILES: CN1CCN(S(=O)(=O)c2ccc(-c3ccc(C[C@@H](C#N)NC(=O)C4(N)CCCCC4)cc3)cc2)CC1] |
| PZ1025 | 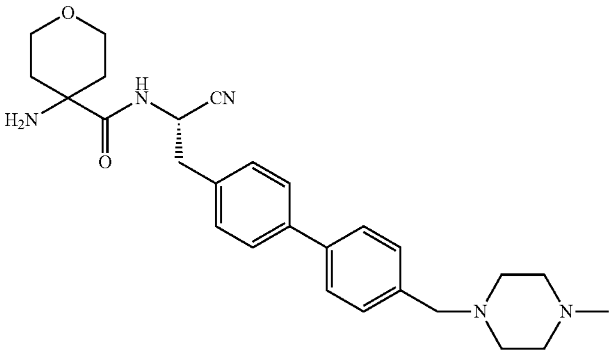 [SMILES: CN1CCN(Cc2ccc(-c3ccc(C[C@@H](C#N)NC(=O)C4(N)CCOCC4)cc3)cc2)CC1] |
| PZ1034 | 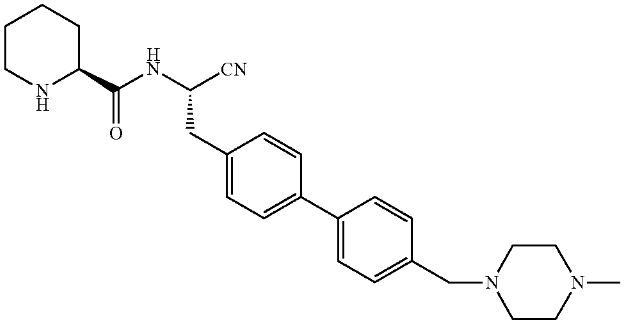 [SMILES: CN1CCN(Cc2ccc(-c3ccc(C[C@@H](C#N)NC(=O)[C@@H]4CCCCN4)cc3)cc2)CC1] |
U.S. Pat. Nos. 8,877,775; 9,440,960 and 9,879,026 are incorporated by reference herein in their entireties for all purposes.

;1

TABLE 2

| Compound | Structural formula |
| --- | --- |
| brensocatib | 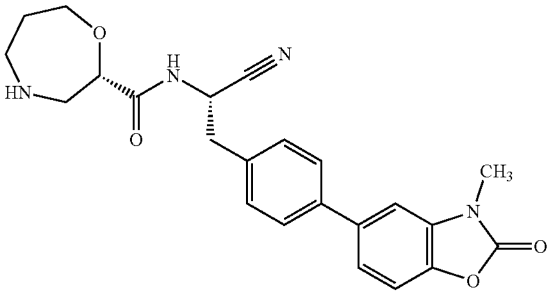 [SMILES: Cn1c(=O)oc2ccc(-c3ccc(C[C@@H](C#N)NC(=O)[C@@H]4CNCCCO4)cc3)cc21] |
| (2S)-N-[(1S)-1-cyano-2-phenylethyl]-1,4-oxazepane-2-carboxamide compounds of Formula (I), defined herein | 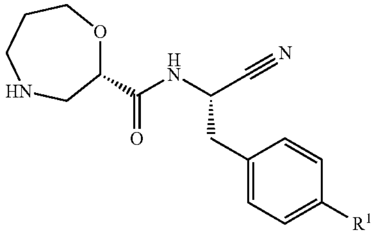 |

Other CTSC inhibitors for use in the methods provided herein have been disclosed in U.S. Pat. Nos. 8,889,708, 8,987,249, and 9,073,869, and International Patent Application Publication Nos. WO 2012/119941, WO 2015/032945, WO 2015/032943, and WO 2015/032942, the contents of each of which is herein incorporated by reference. Other CTSC inhibitors amenable for use in the methods described herein have been disclosed in U.S. Pat. Nos. 8,999,975, 9,440,960, 9,713,606, 9,856,228, 9,879,026, RE47,636E, 10,238,633, Bondebjerg et al., "Novel semicarbazide-derived inhibitors of human dipeptidyl peptidase I (hDPPI)," *Bioorg Med Chem.* 13:4008-4424 (2005), and Bondebjerg et al., "Dipeptidyl Nitriles as Human Dipeptidyl Peptidase 1 Inhibitors," *Bioorg Med Chem Lett.* 16:3614-3617 (2006), the contents of each of which is herein incorporated by reference in their entireties.

In some embodiments of the method for treating a primary cancer or a metastasis of a cancer provided herein, the method comprises administering to a patient in need of treatment, for a treatment period, a pharmaceutical composition comprising an effective amount of a compound of Formula (I), or a pharmaceutically acceptable salt thereof:

(I)

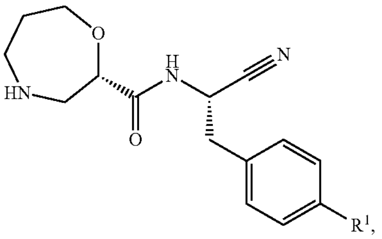

wherein, $R^1$ is

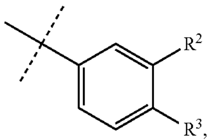

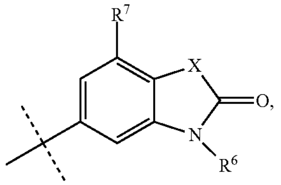

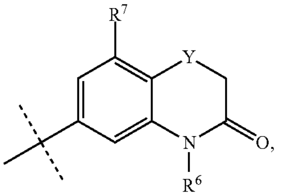

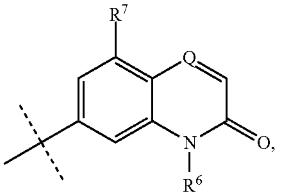

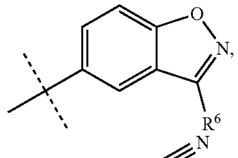

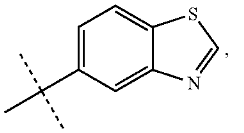

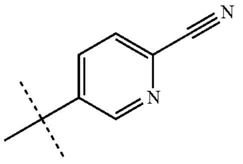

or

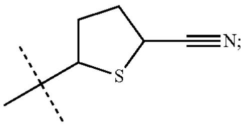

$R^2$ is hydrogen, F, Cl, Br, $OSO_2C_{1-3}$alkyl, or $C_{1-3}$alkyl;

$R^3$ is hydrogen, F, Cl, Br, CN, $CF_3$, $SO_2C_{1-3}$alkyl, $CONH_2$ or $SO_2NR^4R^5$, wherein $R^4$ and $R^5$ together with the nitrogen atom to which they are attached form an azetidine, pyrrolidine or piperidine ring;

X is O, S or $CF_2$;

Y is O or S;

Q is CH or N;

$R^6$ is $C_{1-3}$alkyl, wherein the $C_{1-3}$alkyl is optionally substituted by 1, 2 or 3 F and optionally by one substituent selected from OH, $OC_{1-3}$alkyl, $N(C_{1-3}alkyl)_2$, cyclopropyl, or tetrahydropyran; and $R^7$ is hydrogen, F, Cl or $CH_3$, wherein the treating inhibits, slows, or reverses the progression of the primary cancer or inhibits, slows, or reverses the progression metastasis.

In a further embodiment, the method is a method of treating a metastasis of a cancer.

In one embodiment, a pharmaceutical composition comprising an effective amount of a compound of Formula (I) is administered to the patient, wherein, $R^1$ is

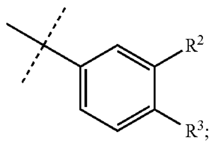

$R^2$ is hydrogen, F, Cl, Br, $OSO_2C_{1-3}$alkyl, or $C_{1-3}$alkyl; $R^3$ is hydrogen, F, Cl, Br, CN, $CF_3$, $SO_2C_{1-3}$alkyl, $CONH_2$ or $SO_2NR^4R^5$, wherein $R^4$ and $R^5$ together with the nitrogen atom to which they are attached form an azetidine, pyrrolidine or piperidine ring. In a further embodiment, $R^2$ is hydrogen, F, Cl or $C_{1-3}$alkyl; and $R^3$ is hydrogen, F, Cl, CN or $SO_2C_{1-3}$alkyl. In a further embodiment, $R^3$ is hydrogen, F or CN.

In another embodiment, a pharmaceutical composition comprising an effective amount of a compound of Formula (I) is administered to the patient, wherein, $R^1$ is

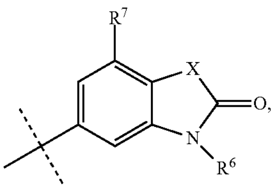

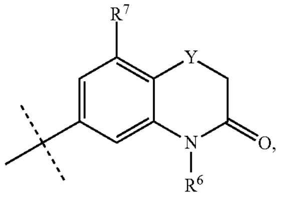

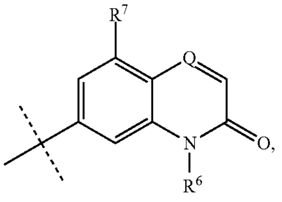

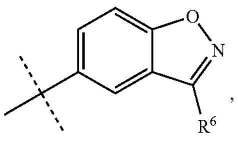

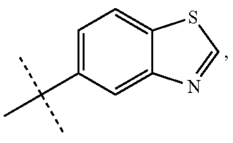

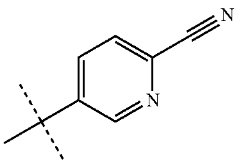

or

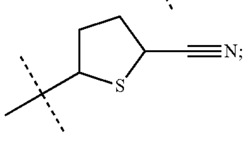

X is O, S or $CF_2$; Y is O or S; Q is CH or N; $R^6$ is $C_{1-3}$alkyl, wherein the $C_{1-3}$alkyl is optionally substituted by 1, 2 or 3 F and optionally substituted by OH, $OC_{1-3}$alkyl, $N(C_{1-3}\ alkyl)_2$, cyclopropyl, or tetrahydropyran; and $R^7$ is hydrogen, F, Cl or $CH_3$. In a further embodiment, $R^1$ is

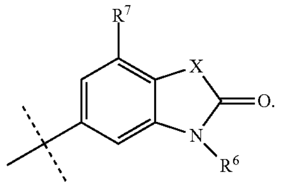

In another embodiment, a pharmaceutical composition comprising an effective amount of a compound of Formula (I) is administered to the patient, wherein, $R^1$ is

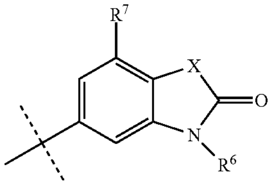

or

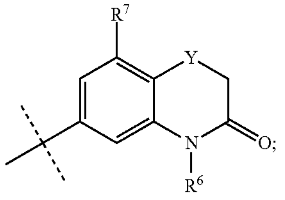

X is O, S or $CF_2$; Y is O or S; $R^6$ is $C_{1-3}$alkyl, optionally substituted by 1, 2 or 3 F and optionally substituted by OH, $OC_{1-3}$alkyl, $N(C_{1-3}alkyl)_2$, cyclopropyl, or tetrahydropyran; and $R^7$ is hydrogen, F, Cl or $CH_3$. In a further embodiment, $R^1$ is

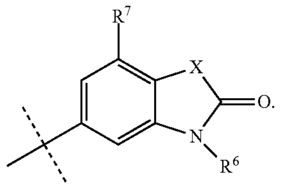

In some embodiments, a pharmaceutical composition comprising an effective amount of a compound of Formula (I) is administered to the patient, wherein, $R^1$ is

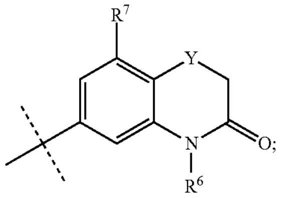

X is O; S or $CF_2$; $R^6$ is $C_{1-3}$alkyl, wherein the $C_{1-3}$alkyl is optionally substituted by 1, 2 or 3 F; and $R^7$ is hydrogen, F, Cl or $CH_3$.

In yet another embodiment, a pharmaceutical composition comprising an effective amount of a compound of Formula (I) is administered to the patient, wherein, $R^1$ is

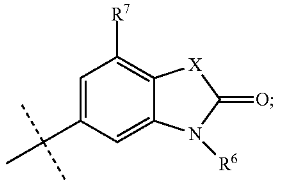

X is O; $R^6$ is $C_{1-3}$alkyl, wherein the $C_{1-3}$alkyl is optionally substituted by 1, 2 or 3 F; and $R^7$ is hydrogen. In a further embodiment, $R^6$ is $C_{1-3}$alkyl, i.e., methyl, ethyl, or propyl. In still a further embodiment, $R^6$ is methyl.

In even another embodiment, a pharmaceutical composition comprising an effective amount of a compound of Formula (I) is administered to the patient, wherein $R^2$ is hydrogen, F, Cl, Br, $OSO_2C_{1-3}$alkyl or $C_{1-3}$alkyl. In a further embodiment, $R^2$ is hydrogen, F, Cl or $C_{1-3}$alkyl. In still a further embodiment, $R^2$ is hydrogen, F or $C_{1-3}$alkyl.

In one embodiment of a method provided herein, a pharmaceutical composition comprising an effective amount of a compound of Formula (I) is administered to the patient, wherein $R^3$ is hydrogen, F, Cl, Br, CN, $CF_3$, $SO_2C_{1-3}$alkyl $CONH_2$ or $SO_2NR^4R^5$, wherein $R^4$ and $R^5$ together with the nitrogen atom to which they are attached form an azetidine, pyrrolidine or piperidine ring. In a further embodiment, $R^3$ is hydrogen, F, Cl, CN or $SO_2C_{1-3}$alkyl. In still a further embodiment, $R^3$ is hydrogen, F or CN.

In one embodiment of a method provided herein for treating a primary cancer or a metastasis of a cancer, a pharmaceutical composition comprising an effective amount of a compound of Formula (I) is administered to the patient, wherein $R^6$ is $C_{1-3}$alkyl, and the $C_{1-3}$alkyl is optionally substituted by 1, 2 or 3 F and optionally by one substituent selected from OH, $OC_{1-3}$alkyl, $N(C_{1-3}alkyl)_2$, cyclopropyl, or tetrahydropyran. In a further embodiment, $R^6$ is $C_{1-3}$alkyl, wherein the $C_{1-3}$alkyl is optionally substituted by 1, 2 or 3 F. In still a further embodiment, $R^6$ is methyl or ethyl. In still a further embodiment $R^6$ is methyl.

In even another embodiment, $R^7$ is hydrogen, F, Cl or $CH_3$. In a further embodiment $R^7$ is hydrogen.

In one embodiment, a pharmaceutical composition administered to the patient comprises an effective amount of (2S)—N-{(1S)-1-cyano-2-[4-(3-methyl-2-oxo-2,3-dihydro-1,3-benzoxazol-5-yl)phenyl]ethyl}-1,4-oxazepane-2-carboxamide (brensocatib):

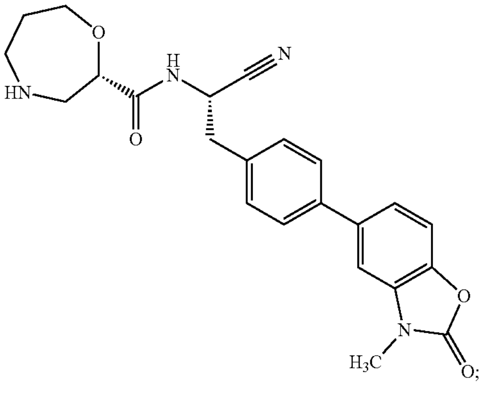 [SMILES: Cn1c(=O)oc2ccc(-c3ccc(C[C@@H](C#N)NC(=O)[C@@H]4CNCCCO4)cc3)cc21]

or a pharmaceutically acceptable salt thereof. In a further embodiment, the compound of Formula (I) is brensocatib. In a further embodiment, the method is a method for treating a metastasis of a cancer. In another embodiment, a pharmaceutical composition comprising an effective amount of brensocatib is administered to a patient in need of treatment of a primary cancer.

In some embodiments, the compound administered to the patient is one of the following compounds of Formula (I):

(2S)—N-[(1S)-1-Cyano-2-(4'-cyanobiphenyl-4-yl)ethyl]-1,4-oxazepane-2-carboxamide, (2S)—N-{(1S)-1-Cyano-2-[4-(3-methyl-2-oxo-2,3-dihydro-1,3-benzoxazol-5-yl)phenyl]ethyl}-1,4-oxazepane-2-carboxamide, (2S)—N-{(1S)-1-Cyano-2-[4-(3,7-dimethyl-2-oxo-2,3-dihydro-1,3-benzoxazol-5-yl)phenyl]ethyl}-1,4-oxazepane-2-carboxamide, 4'[(2S)-2-Cyano-2-{[(2S)-1,4-oxazepan-2-ylcarbonyl]amino}ethyl]biphenyl-3-yl methanesulfonate, (2S)—N-{(1S)-1-Cyano-2-[4-(3-methyl-1,2-benzoxazol-5-yl)phenyl]ethyl}-1,4-oxazepane-2-carboxamide, (2S)—N-{(1S)-1-Cyano-2-[4'-(trifluoromethyl)biphenyl-4-yl]ethyl}-1,4-oxazepane-2-carboxamide, (2S)—N-[1S)-1-Cyano-2-(3',4'-difluorobiphenyl-4-yl)ethyl]-1,4-oxazepane-2-carboxamide, (2S)—N-{1S)-1-Cyano-2-[4-(6-cyanopyridin-3-yl)phenyl)]ethyl}-1,4-oxazepane-2-carboxamide, (2S)—N-{(1S)-1-Cyano-2-[4-(4-methyl-3-oxo-3,4-dihydro-2H-1,4-benzothiazin-6-yl)phenyl]ethyl}-1,4-oxazepane-2-carboxamide, (2S)—N-{(1S)-1-Cyano-2[4-(3-ethyl-7-methyl-2-oxo-2,3-dihydro-1,3-benzoxazol-5-yl)phenyl]ethyl}-1,4-oxazepane-2-carboxamide, (2S)—N-[(1S)-1-Cyano-2-{4-[3-(2-hydroxy-2-methylpropyl)-2-oxo-2,3-dihydro-1,3-benzoxazol-5-yl]phenyl}ethyl]-1,4-oxazepane-2-carboxamide, (2S)—N-[(1S)-1-Cyano-2-{4-[3-(2,2-difluoroethyl)-7-fluoro-2-oxo-2,3-dihydro-1,3-benzoxazol-5-yl]phenyl}ethyl]-1,4-oxazepane-2-carboxamide, (2S)—N-[(1S)-1-Cyano-2-(4-{3-[2-(dimethylamino)ethyl]-2-oxo-2,3-dihydro-1,3-benzoxazol-5-yl}phenyl)ethyl]-1,4-oxazepane-2-carboxamide, ((2S)—N-{(1S)-1-Cyano-2-[4-(3,3-difluoro-1-methyl-2-oxo-2,3-dihydro-1H-indol-6-yl)phenyl]ethyl}-1,4-oxazepane-2-carboxamide, (2S)—N-{1S)-1-Cyano-2-[4-(7-fluoro-3-methyl-2-oxo-2,3-dihydro-1,3-benzoxazol-5-yl)phenyl]ethyl}-1,4-oxazepane-2-carboxamide, (2S)—N-{(1S)-1-Cyano-2-[4-(3-ethyl-2-oxo-2,3-dihydro-1,3-benzoxazol-5-yl)phenyl]ethyl}-1,4-oxazepane-2-carboxamide, (2S)—N-[(1S)-1-Cyano-2-{4-[3-(cyclopropylmethyl)-2-oxo-2,3-dihydro-1,3-benzoxazol-5-yl]phenyl}ethyl]-1,4-oxazepane-2-carboxamide, (2S)—N-[(1S)-1-Cyano-2-{4-[3-(2-methoxyethyl)-2-oxo-2,3-dihydro-1,3-benzothiazol-5-yl]phenyl}ethyl]-1,4-oxazepane-2-carboxamide, (2S)—N-[(1S)-1-Cyano-2-{4-[2-oxo-3-(propan-2-yl)-2,3-dihydro-1,3-benzoxazol-5-yl]phenyl}ethyl]-1,4-oxazepane-2-carboxamide, (2S)—N-{(1S-1-Cyano-2-[(4-(4-methyl-3-oxo-3,4-dihydro-2H-1,4-benzoxazin-6-yl)phenyl]ethyl}-1,4-oxazepane-2-carboxamide, (2S)—N-[(1S)-1-Cyano-2-{4-[3-(2-methoxyethyl)-2-oxo-2,3-dihydro-1,3-benzoxazol-5-yl]phenyl}ethyl]-1,4-oxazepane-2-carboxamide, (2S)—N{(1S)-1-Cyano-2-[4-(5-cyanothiophen-2-yl)phenyl]ethyl}-1,4-oxazepane-2-carboxamide, (2S)—N-[(1S)-2-(4'-Carbamoyl-3'-fluorobiphenyl-4-yl)-1-cyanoethyl]-1,4-oxazepane-2-carboxamide,
(2S)—N-{(1S)-1-Cyano-2-[4-(1-methyl-2-oxo-1,2-dihydroquinolin-7-yl)phenyl]ethyl}-1,4-oxazepane-2-carboxamide,
(2S)—N-[(1S)-1-Cyano-2-{4-[2-oxo-3-(tetrahydro-2H-pyran-4-ylmethyl)-2,3-dihydro-1,3-benzoxazol-5-yl]phenyl}ethyl]-1,4-oxazepane-2-carboxamide,
(2S)—N-{(1S)-2-[4-(7-Chloro-3-methyl-2-oxo-2,3-dihydro-1,3-benzoxazol-5-yl)phenyl]-1-cyanoethyl}-1,4-oxazepane-2-carboxamide,
(2S)—N-[(2S)-1-Cyano-2-{4-[3-(2,2-difluoroethyl)-2-oxo-2,3-dihydro-1,3-benzoxazol-5-yl]phenyl}ethyl]-1,4-oxazepane-2-carboxamide,
(2S)—N-[(1S)-1-Cyano-2-{4[2-oxo-3-(2,2,2-trifluoroethyl)-2,3-dihydro-1,3-benzoxazol-5-yl]phenyl}ethyl]-1,4-oxazepane-2-carboxamide,
(2S)—N-{(1S)-1-Cyano-2-[4-(3-methyl-2-oxo-2,3-dihydro-1,3-benzothiazol-5-yl)phenyl]ethyl}-1,4-oxazepane-2-carboxamide,
(2S)—N(1S)-1-Cyano-2['-(methylsulfonyl)biphenyl-4-yl]ethyl)-1,4-oxazepane-2-carboxamide,
(2S)—N-{(1S)-2-[4'-(Azetidin-1-ylsulfonyl)biphenyl-4-yl]-1-cyanoethyl}-1,4-oxazepane-2-carboxamide,
(2S)—N-[(1S)-1-Cyano-2-(4'-fluorobiphenyl-4-yl)ethyl]-1,4-oxazepane-2-carboxamide,
(2S)—N-{(1S)-2-[4-(1,3-Benzothiazol-5-yl)phenyl]-1-cyanoethyl}-1,4-oxazepane-2-carboxamide, or
(2S)—N-[(1S)-1-Cyano-2-(4'-cyanobiphenyl-4-yl)ethyl]-1,4-oxazepane-2-carboxamide, or a pharmaceutically acceptable salt of one of the foregoing compounds.

In one embodiment of the methods provided herein, the patient is administered a pharmaceutical composition comprises an effective amount of brensocatib:

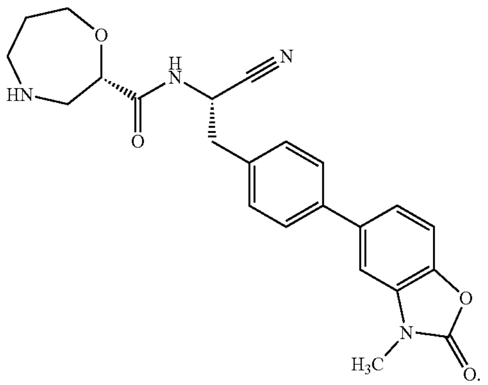 [SMILES: Cn1c(=O)oc2ccc(-c3ccc(C[C@@H](C#N)NC(=O)[C@@H]4CNCCCO4)cc3)cc21]

In some embodiments, brensocatib is in polymorphic Form A as disclosed in U.S. Pat. No. 9,522,894, the disclosure of which is incorporated herein by reference in its entirety for all purposes. In some embodiments, brensocatib is characterized by an X-ray powder diffraction pattern having a peak at about 12.2±0.2 (° 2-theta), measured using CuKα radiation. In some embodiments, brensocatib is characterized by an X-ray powder diffraction pattern having a peak at about 20.6±0.2 (° 2-theta), measured using CuKα radiation. In some embodiments, brensocatib is characterized by an X-ray powder diffraction pattern having a peak at about 12.2±0.2 and about 20.6±0.2 (° 2-theta), measured using CuKα radiation. In some embodiments, brensocatib is characterized by an X-ray powder diffraction pattern having a peak at about 12.2±0.2, about 14.3±0.2, about 16.2±0.2, about 19.1±0.2 and about 20.6±0.2 (° 2-theta), measured using CuKα radiation.

The skilled person will recognize that the compounds of the present disclosure may be prepared, in known manner, in a variety of ways. For example, in one embodiment, compounds of Formula (I) are prepared according to the methods set forth in U.S. Pat. No. 9,522,894, incorporated by reference herein in its entirety for all purposes.

The CTSC inhibitors described herein, for example compounds of Formula (I), can be present in the pharmaceutical composition as a pharmaceutically acceptable salt.

Without wishing to be bound by theory, a pharmaceutically acceptable salt of a CTSC inhibitor described herein, for example, a compound of Formula (I), may be advantageous due to one or more of its chemical or physical properties, such as stability in differing temperatures and humidities, or a desirable solubility in $H_2O$, oil, or other solvent. In some instances, a salt may be used to aid in the isolation or purification of the CTSC inhibitor.

Where the CTSC inhibitor is sufficiently acidic, pharmaceutically acceptable salts include, but are not limited to, an alkali metal salt, e.g., Na or K, an alkali earth metal salt, e.g., Ca or Mg, or an organic amine salt. Where the CTSC inhibitor is sufficiently basic, pharmaceutically acceptable salts include, but are not limited to, inorganic or organic acid addition salts. In one embodiment, a pharmaceutically acceptable salt is a chloride salt, a maleate salt, a sulfate salt, a citrate salt, a mesylate salt, a tartrate salt, a bromide salt, a nitrate salt, a phosphate salt, an acetate salt, or a gluconate salt.

In some embodiments, there may be more than one cation or anion depending on the number of charged functions and the valency of the cations or anions.

For reviews on suitable salts, and pharmaceutically acceptable salts amenable for use herein, see Berge et al., *J. Pharm. Sci,* 1977, 66, 1-19 or "Handbook of Pharmaceutical Salts: Properties, selection and use", P. H. Stahl, P. G. Vermuth, IUPAC, Wiley-VCH, 2002, incorporated by reference herein in its entirety for all purposes.

The CTSC inhibitors described herein may form mixtures of its salt and co-crystal forms. It should therefore be understood that the methods provided herein can employ such salt/co-crystal mixtures of the CTSC inhibitors, for example, the compounds of Formula (I).

Salts and co-crystals may be characterized using well known techniques, for example X-ray powder diffraction, single crystal X-ray diffraction (for example to evaluate proton position, bond lengths or bond angles), solid state NMR, (to evaluate for example, C, N or P chemical shifts) or spectroscopic techniques (to measure for example, OH, NH or COOH signals and IR peak shifts resulting from hydrogen bonding).

It is also to be understood that CTSC inhibitors may exist in solvated form, e.g., hydrates, including solvates of a pharmaceutically acceptable salt of a compound of Formula (I) or another CTSC inhibitor described herein.

Certain CTSC inhibitors described herein may also contain linkages (e.g., carbon-carbon bonds, carbon-nitrogen bonds such as amide bonds) wherein bond rotation is restricted about that particular linkage, e.g., restriction resulting from the presence of a ring bond or double bond. Accordingly, it is to be understood that the present disclosure encompasses all such isomers. In addition, the CTSC inhibitor may contain multiple tautomeric forms. Stereoisomers may be separated using conventional techniques, e.g., chromatography or fractional crystallization, or the stereoisomers may be made by stereoselective synthesis.

In one embodiment, the pharmaceutical composition comprises an effective amount of an isotopically-labeled (or "radio-labelled") CTSC inhibitor, for example, a compound of Formula (I). Such a derivative is a derivative of a CTSC inhibitor where one or more atoms are replaced by an atom having an atomic mass or mass number different from the atomic mass or mass number typically found in nature. Examples of radionuclides that may be incorporated include 2H (also written as "D" for deuterium). As such, in one embodiment, the CTSC inhibitor is one of the inhibitors described herein where one or more hydrogen atoms are replaced by one or more deuterium atoms; and the deuterated compound is used in one of the methods provided herein.

In another embodiment, the CTSC inhibitor is administered in the form of a prodrug which is broken down in the human or animal body to give one of the CTSC inhibitors described herein. Examples of prodrugs include in vivo hydrolysable esters of a compound of the Formula (I).

An in vivo hydrolysable (or cleavable) ester of a CTSC inhibitor compound that contains a carboxy or a hydroxy group is, for example, a pharmaceutically acceptable ester which is hydrolyzed in the human or animal body to produce the parent acid or alcohol. For examples of ester prodrugs derivatives, see: *Curr. Drug. Metab.* 2003, 4, 461, incorporated by reference herein in its entirety for all purposes. Various other forms of prodrugs are known in the art, and can be used in the methods provided herein. For examples of prodrugs, see: *Nature Reviews Drug Discovery* 2008, 7, 255, the disclosure of which is incorporated by reference herein in its entirety for all purposes.

The dosage administered will vary depending on the CTSC inhibitor employed and the mode of administration. The dosage administered will vary with the CTSC inhibitor employed and the mode of administration. For example, in one embodiment, the daily dosage of the CTSC inhibitor, may be in the range from 0.05 micrograms per kilogram body weight (μg/kg) to 100 micrograms per kilogram body weight (μg/kg). In another embodiment, if the CTSC inhibitor is administered orally, then the daily dosage of the compound used in the methods of the invention may be in the range from 0.01 micrograms per kilogram body weight (μg/kg) to 100 milligrams per kilogram body weight (mg/kg).

In one embodiment, the daily dosage of the CTSC inhibitor is from about 5 mg to about 70 mg, from about 10 mg to about 60 mg, or from about 10 mg to about 40 mg. In a further embodiment, the CTSC inhibitor is a compound of Formula (I), or a pharmaceutically acceptable salt thereof. In even a further embodiment, the compound is brensocatib. In another embodiment, the daily dosage of the CTSC inhibitor is about 10 mg, about 25 mg, about 40 mg, or about 65 mg. In a further embodiment, the CTSC inhibitor is a compound of Formula (I), or a pharmaceutically acceptable salt thereof. In even a further embodiment, the compound is brensocatib.

In one embodiment, the CTSC inhibitor is administered in an oral dosage form. In one embodiment, the oral dosage of the CTSC inhibitor is from about 5 mg to about 70 mg, from about 10 mg to about 60 mg, or from about 10 mg to about 40 mg. In a further embodiment, the CTSC inhibitor is a compound of Formula (I), or a pharmaceutically acceptable salt thereof. In even a further embodiment, the compound is brensocatib. In another embodiment, the oral dosage of the CTSC inhibitor is about 10 mg, about 25 mg, about 40 mg, or about 65 mg. In a further embodiment, the CTSC inhibitor is a compound of Formula (I), or a pharmaceutically acceptable salt thereof. In even a further embodiment, the compound is brensocatib.

In the methods provided herein, a pharmaceutical composition comprising an effective amount of a CTSC inhibitor is administered in patient in need of treatment of a primary cancer or a metastasis of a cancer.

The pharmaceutical composition, in one embodiment, is in a solid dosage form. Solid dosage forms used for oral administration include capsules, tablets, pills, powders, and granules. Among these solid dosage forms, an active compound is mixed with at least one conventional inert excipient (or vehicle), such as sodium citrate or dicalcium phosphate, or mixed with the following ingredients: (a) a filler or a compatibilizer, such as starch, lactose, sucrose, glucose, mannitol, and silicic acid; (b) a bonding agent, such as hydroxymethyl cellulose, alginate, gelatin, polyvinylpyrrolidone, sucrose, and gum arabic; (c) a moisturizer, such as glycerin; (d) a disintegrant, such as agar, calcium carbonate, potato starch or tapioca starch, alginic acid, some composite silicates, and sodium carbonate; (e) a slow solvent, such as paraffin; (f) an absorbing accelerator, such as quaternary amine compounds; (g) a wetting agent, such as cetyl alcohol and glyceryl monostearate; (h) an adsorbent, such as kaolin; and (i) a lubricant, such as talc, calcium stearate, magnesium stearate, solid polyethylene glycol, sodium dodecyl sulfate, or a mixture thereof. Dosage forms of capsules, tablets, and pills may also contain a buffer agent.

In one embodiment, a pharmaceutical composition is in tablet form. In a further embodiment, the pharmaceutical composition in tablet form further comprises a tablet coating.

Solid dosage forms such as tablets, sugared pills, capsules, pills, and granules may be prepared using coatings and shells, such as enteric coatings and other materials known in the art. They may contain opacifiers, and moreover, active compounds or compounds in such compositions may be released in a portion of the digestive tract in a delayed manner. Examples of embedding components that can be employed are polymeric materials and waxy materials. If necessary, the active compounds may also be formed into microcapsules with one or more of the above excipients.

Liquid dosage forms for oral administration include pharmaceutically acceptable emulsions, solutions, suspensions, syrups, or tincture. In addition to active compounds, a liquid dosage form may contain inert diluents conventionally employed in the art, such as water or other solvents, solubilizers, and emulsifiers, like ethanol, isopropanol, ethyl carbonate, ethyl acetate, propylene glycol, 1,3-butanediol, dimethylformamide, and oils, in particular cottonseed oil, peanut oil, corn germ oil, olive oil, castor oil, sesame oil, or a mixture of these substances.

Liquid preparations for oral application may be in the form of syrups, solutions or suspensions. Solutions, for example may contain the compound used in the methods of the invention, the balance being sugar and a mixture of ethanol, water, glycerol and propylene glycol. Optionally such liquid preparations may contain coloring agents, flavoring agents, saccharine and/or carboxymethylcellulose as a thickening agent. Furthermore, other excipients known to those skilled in art may be used when making formulations for oral use.

In addition to these inert diluents, the compositions may also contain adjuvants, such as wetting agents, emulsifiers, suspending agents, sweetening agents, flavoring agents, and spices.

In addition to active compounds, a suspension may contain a suspending agent, such as ethoxylated isostearyl alcohol, polyoxyethylene sorbitol, sorbitan ester, microcrystalline cellulose, aluminum methoxide, agar, or a mixture of these substances.

Compositions for parenteral injection may include a physiologically acceptable sterile aqueous or nonaqueous solution, dispersion, suspension, or emulsion, and sterile powder for re-dissolution into a sterile injectable solution or dispersion. Suitable aqueous and nonaqueous vehicles, diluents, solvents, or excipients include water, ethanol, polyol, and suitable mixtures thereof.

The pharmaceutical compositions used in the methods provided herein, in one embodiment, comprise an effective amount of a CTSC inhibitor and a pharmaceutically acceptable carrier, adjuvant or diluent. A "pharmaceutically acceptable carrier, adjuvant or diluent" refers to one or more compatible solid or liquid fillers or gel substances, which are suitable for use on human body and must have sufficient purity and sufficiently low toxicity. The "compatible" herein refers to that all ingredients in a composition can be mixed with each other and can be mixed with the compounds according to the present disclosure, while the medicinal effect of the compounds is not significantly reduced. Some examples of the pharmaceutically acceptable carrier, adjuvant or diluents include cellulose and derivatives thereof (e.g., sodium carboxymethyl cellulose, sodium ethyl cellulose, and cellulose acetate), gelatin, talc, solid lubricants (e.g., stearic acid and magnesium stearate), calcium sulfate, plant oils (e.g., soybean oil, sesame oil, peanut oil, and olive oil), polyols (e.g., propylene glycol, glycerin, mannitol, and sorbitol), emulsifiers (e.g., Tween), wetting agents (e.g., sodium dodecyl sulfate), coloring agents, flavoring agents, stabilizing agents, antioxidants, preservatives, pyrogen-free water, and the like.

For oral administration the CTSC inhibitor may be admixed with one or more pharmaceutically acceptable adjuvants, diluents or carriers, for example, lactose, saccharose, sorbitol, mannitol; starch, for example, potato starch, corn starch or amylopectin; cellulose derivative; binder, for example, gelatine or polyvinylpyrrolidone; disintegrant, for example cellulose derivative, and/or lubricant, for example, magnesium stearate, calcium stearate, polyethylene glycol, wax, paraffin, and the like, and then compressed into tablets. If coated tablets are required, the cores, prepared as described above, may be coated with a suitable polymer dissolved or dispersed in water or readily volatile organic solvent(s). Alternatively, the tablet may be coated with a concentrated sugar solution which may contain, for example, gum arabic, gelatine, talcum and titanium dioxide.

In one oral administration embodiment, the oral dosage form is a film-coated oral tablet. In a further embodiment, the dosage form is an immediate release dosage form with rapid dissolution characteristics under in vitro test conditions.

For the preparation of soft gelatine capsules, the compound used in the methods of the invention may be admixed with, for example, a vegetable oil or polyethylene glycol. Hard gelatine capsules may contain granules of the compound using pharmaceutical excipients like the above-mentioned excipients for tablets. Also, liquid or semisolid formulations of the compound used in the methods of the invention may be filled into hard gelatine capsules.

In one embodiment, the composition is an oral disintegrating tablet (ODT). ODTs differ from traditional tablets in that they are designed to be dissolved on the tongue rather than swallowed whole.

In one embodiment, the composition is an oral thin film or an oral disintegrating film (ODF). Such formulations, when placed on the tongue, hydrate via interaction with saliva, and releases the active compound from the dosage form. The ODF, in one embodiment, contains a film-forming polymer such as hydroxypropylmethylcellulose (HPMC), hydroxypropyl cellulose (HPC), pullulan, carboxymethyl cellulose (CMC), pectin, starch, polyvinyl acetate (PVA) or sodium alginate.

In one embodiment of the methods provided herein for treating a primary cancer or a metastasis of a cancer, the pharmaceutical composition is one of the compositions described in International Application Publication No. WO 2019/166626, the disclosure of which is incorporated herein by reference in its entirety for all purposes.

In one embodiment, the pharmaceutically acceptable carrier, adjuvant or diluent is sterile saline. In other aspects of the present disclosure, the pharmaceutically acceptable carrier, adjuvant or diluent is phosphate-buffered saline (PBS).

Conventional procedures for the selection and preparation of suitable pharmaceutical formulations, depending on the route of administration, are described in, for example, "Pharmaceuticals—The Science of Dosage Form Designs", M. E. Aulton, Churchill Livingstone, $2^{nd}$ Ed. 2002, incorporated by reference herein in its entirety for all purposes.

In the methods provided herein, the pharmaceutical composition is administered for a treatment period. The treatment period, in one embodiment, is at least one (1) month, at least three (3) months, at least six (6) months, at least twelve (12) months, at least eighteen (18) months, at least twenty four (24) months, at least thirty (30) months or at least thirty six (36) months.

In one embodiment, the treatment period is from about six (6) months to about thirty six (36) months. In a further embodiment, the treatment period is from about six months to about thirty (30) months. In a further embodiment, the treatment period is from about six months to about twenty four (24) months. In even a further embodiment, the treatment period is from about six (6) months to about eighteen (18) months. In yet even a further embodiment, the treatment period is from about six (6) months to about twelve (12) months.

In another embodiment, the treatment period is from about twelve (12) months to about thirty six (36) months. In a further embodiment, the treatment period is from about twelve (12) months to about thirty (30) months. In a further embodiment, the treatment period is from about twelve (12) months to about twenty four (24) months. In even a further embodiment, the treatment period is from about twelve (12) months to about eighteen (18) months.

In one embodiment, during the treatment period, the pharmaceutical composition is administered once daily. In a further embodiment, the pharmaceutical composition is an oral composition. In a further embodiment, the pharmaceutical composition is administered at approximately the same time every day, e.g., prior to breakfast.

In another embodiment, during the treatment period, the pharmaceutical composition is administered two times daily. In yet another embodiment, during the treatment period, the pharmaceutical composition is administered 1×per week, every other day, every third day, 2×per week, 3×per week, 4×per week, or 5×per week.

In some embodiments of the present invention, a pharmaceutical composition is administered to a patient in need thereof once per day throughout a treatment period. In another embodiment, the pharmaceutical composition is administered to a patient in need thereof twice per day throughout a treatment period. In another embodiment, a pharmaceutical composition is administered to a patient in need thereof three times per day throughout a treatment period. In yet another embodiment, a pharmaceutical composition is administered to a patient in need thereof every other day throughout a treatment period. In yet even another embodiment, a pharmaceutical composition is administered to a patient in need thereof every third day throughout a treatment period.

In some embodiments of the methods of the invention, the treatment period is at least at least 1 month, at least 6 weeks, at least 2 months, at least 3 months, at least 4 months, at least 5 months, at least 6 months, at least 7 months, at least 8 months, at least 9 months, at least 10 months, at least 11 months, at least 1 year, at least 13 months, at least 14 months, at least 15 months, at least 16 months, at least 17 months, at least 18 months, at least 19 months, at least 20 months, at least 21 months, at least 22 months, at least 23 months, or at least 2 years in duration.

The present invention relates in part to methods for treating a primary cancer and/or a metastasis of a cancer, comprising administering for a treatment period, to a patient in need of treatment, a pharmaceutical composition comprising an effective amount of a CTSC inhibitor, for example, a compound of Formula (I), or a pharmaceutically acceptable salt thereof. In one embodiment, the CTSC inhibitor is brensocatib. In one embodiment, the CTSC inhibitor is one of the compounds set forth in Table 1, or a pharmaceutically acceptable salt thereof. According to the methods of the invention, treating inhibits, slows, or reverses the progression of the primary cancer and/or the metastasis.

In one embodiment, the method is a method for treating a primary cancer. In a further embodiment, the primary cancer is liver cancer. In another embodiment, the primary cancer is breast cancer. The breast cancer, in a further embodiment, is luminal breast cancer, human epidermal growth factor receptor 2 (HER2) positive breast cancer, or triple-negative breast cancer. In yet another embodiment, the primary cancer is lung cancer. The lung cancer, in one embodiment, is non-small cell lung cancer (NSCLC). In another embodiment, the lung cancer is small cell lung cancer.

In one embodiment, the method is a method for treating a metastasis of a cancer. In a further embodiment, the metastasis is of a breast cancer. The breast cancer, in a further embodiment, is luminal breast cancer, human epidermal growth factor receptor 2 (HER2) positive breast cancer, or triple-negative breast cancer.

In one embodiment, as provided above, the method provided herein is a method for treating a metastasis of a breast cancer. In a further embodiment, the metastasis of a breast cancer is a lung metastasis of a breast cancer, liver metastasis of a breast cancer, bone metastasis of a breast cancer or brain metastasis of a breast cancer. In even a further embodiment, the metastasis of a breast cancer is lung metastasis of a breast cancer.

In another embodiment of the method for treating metastasis of a cancer provided herein, the metastasis is of a lung cancer. The lung cancer, in one embodiment, is non-small cell lung cancer (NSCLC). In another embodiment, the lung cancer is small cell lung cancer.

In yet another embodiment of the method for treating a metastasis of a cancer provided herein, the metastasis is a bone metastasis of lung cancer, a liver metastasis of pancreatic cancer, or a liver metastasis of gastric cancer. In yet another embodiment of the method for treating metastasis of a cancer provided herein, the metastasis is a lung metastasis of breast cancer, a liver metastasis of breast cancer, a bone metastasis of breast cancer, a brain metastasis of breast cancer, a bone metastasis of lung cancer, a liver metastasis of pancreatic cancer, or a liver metastasis of gastric cancer.

In one embodiment of the method for treating a metastasis of a cancer provided herein, the metastasis is of a pancreatic cancer or a gastric cancer. In a further embodiment, the metastasis is of a pancreatic cancer. In another embodiment, the metastasis is of a gastric cancer.

In yet even another embodiment, the metastasis is of a bone cancer, liver cancer, stomach cancer or a colorectal cancer.

In one embodiment of the method, treating further comprises mitigating the weight loss of a patient that arose as a result of the primary cancer. In another embodiment, treating further comprises mitigating the weight loss of a patient that arose as a result of tumor metastasis.

In one embodiment of the method for treating a primary cancer or a metastasis of a cancer, the treating further comprises reducing the serological levels of CTSC in the patient. In one embodiment, the primary tumor or the metastasis comprises elevated serological levels of CTSC protein prior to the treatment period. In one embodiment, during the treatment period or subsequent to the treatment period, treating comprises reducing the patient's serological levels of CTSC protein by at least about 10%, compared to the patient's serological levels of CTSC protein prior to the treatment period. In a further embodiment, treating comprises reducing the patient's serological levels of CTSC protein by at least about 20%, compared to the patient's serological levels of CTSC protein prior to the treatment period. In yet a further embodiment, treating comprises reducing the patient's serological levels of CTSC protein by at least about 30%, compared to the patient's serological levels of CTSC protein prior to the treatment period. In even a further embodiment, treating comprises reducing the patient's serological levels of CTSC protein by at least about 40%, compared to the patient's serological levels of CTSC protein prior to the treatment period. In yet even a further embodiment, treating comprises reducing the patient's serological levels of CTSC protein by at least about 50%, compared to the patient's serological levels of CTSC protein prior to the treatment period. In another embodiment, treating comprises reducing the patient's serological levels of CTSC protein by at least about 60%, compared to the patient's serological levels of CTSC protein prior to the treatment period. In even another embodiment, treating comprises reducing the patient's serological levels of CTSC protein by at least about 70%, compared to the patient's serological levels of CTSC protein prior to the treatment period. In yet another embodiment, treating comprises reducing the patient's serological levels of CTSC protein by at least about 80%, compared to the patient's serological levels of CTSC protein prior to the treatment period.

In one embodiment of a method for treating a primary cancer or a metastasis, the patient's serological levels of CTSC protein are reduced by from about 10% to about 80%, compared to the patient's serological levels of CTSC protein prior to the treatment period. In a further embodiment, the patient's serological levels of CTSC protein are reduced by from about 10% to about 70%, compared to the patient's serological levels of CTSC protein prior to the treatment period. In even a further embodiment, the patient's serological levels of CTSC protein are reduced by from about 10% to about 60%, compared to the patient's serological levels of CTSC protein prior to the treatment period. In yet a further embodiment, the patient's serological levels of CTSC protein are reduced by from about 10% to about 50%, compared to the patient's serological levels of CTSC protein prior to the treatment period. In even yet a further embodiment o, the patient's serological levels of CTSC protein are reduced by from about 10% to about 40%, compared to the patient's serological levels of CTSC protein prior to the treatment period.

In another embodiment, the patient's serological levels of CTSC protein are reduced by from about 40% to about 80%, compared to the patient's serological levels of CTSC protein prior to the treatment period. In a further embodiment, the patient's serological levels of CTSC protein are reduced by from about 50% to about 80%, compared to the patient's serological levels of CTSC protein prior to the treatment period. In even a further embodiment, the patient's serological levels of CTSC protein are reduced by from about 60% to about 80%, compared to the patient's serological levels of CTSC protein prior to the treatment period.

In one embodiment of the treatment methods provided herein, the method further comprises reducing neutrophil extracellular traps (NETs) in the patient during the treatment period or subsequent to the treatment period, compared to the number of NETs prior to the treatment period. In further embodiments, the method comprises reducing NETs in the metastasis during the treatment period or subsequent to the treatment period, compared to the number of NETs in the metastasis prior to the treatment period. In another embodiment, the method comprises reducing NETs in the primary cancer during the treatment period or subsequent to the treatment period, compared to the number of NETs in the primary cancer prior to the treatment period. In one embodiment, the method comprises reducing circulating NETs in the patient during the treatment period or subsequent to the treatment period, compared to the number of circulating NETs prior to the treatment period.

The number of NETs (e.g., circulating or at the site or sites of metastasis), in one embodiment of a method provided herein, during the treatment period or subsequent to the treatment period, is reduced by at least about 10%, compared to the number of NETs prior to the treatment period. In a further embodiment, the number of NETs is reduced by at least about 20%, compared to the number of NETs prior to the treatment period. In yet a further embodiment, the number of NETs is reduced by at least about 30%, compared to the number of NETs prior to the treatment period. In even a further embodiment, the number of NETs is reduced by at least about 40%, compared to the number of NETs prior to the treatment period. In yet even a further embodiment, the number of NETs is reduced by at least about 50%, compared to the number of NETs prior to the treatment period. In another embodiment, the number of NETs is reduced by at least about 60%, compared to the number of NETs prior to the treatment period. In even another embodiment, the number of NETs is reduced by at least about 70%, compared to the number of NETs prior to the treatment period. In yet another embodiment, the number of NETs is reduced by at least about 80%, compared to the number of NETs prior to the treatment period.

In one embodiment of a method provided herein, the number of NETs (e.g., circulating, or present in the primary tumor or in the tumor metastasis), during the treatment period or subsequent to the treatment period, is reduced by from about 10% to about 80%, compared to the number of NETs prior to the treatment period. In a further embodiment, the number of NETs is reduced by from about 10% to about 70%, compared to the number of NETs prior to the treatment period. In even a further embodiment, the number of NETs is reduced by from about 10% to about 60%, compared to the number of NETs prior to the treatment period. In yet a further embodiment, the number of NETs is reduced by from about 10% to about 50%, compared to the number of NETs prior to the treatment period. In even yet a further embodiment, the number of NETs is reduced by from about 10% to about 40%, compared to the number of NETs prior to the treatment period.

In another embodiment of a treatment method provided herein, the number of NETs is reduced by from about 40% to about 80%, compared to the number of NETs prior to the treatment period. In a further embodiment, the number of NETs is reduced by from about 50% to about 80%, compared to the number of NETs prior to the treatment period. In even a further embodiment, the number of NETs is reduced by from about 60% to about 80%, compared to the number of NETs prior to the treatment period.

In one embodiment, NETs are detected by immunofluorescence staining.

In another embodiment of a metastasis treatment method provided herein, the method further comprises reducing neutrophil migration in the metastasis during the treatment period or subsequent to the treatment period, compared to the neutrophil migration prior to the treatment period, or compared to a metastasis patient not treated with the pharmaceutical composition. In a further embodiment, neutrophil migration is reduced by at least about 5%, 10%, 15%, 20%, 25%, 30%, 35%, 40%, 45%, 50%, 55%, 60%, 65%, 70%, 75%, 80%, 85%, or 90% during the treatment period or subsequent to the treatment period, as compared to the neutrophil migration in the metastasis prior to the treatment period. Neutrophil migration in one embodiment, is measured by immunofluorescence staining.

In another embodiment of a primary cancer treatment method provided herein, the method further comprises reducing neutrophil migration in the metastasis during the treatment period or subsequent to the treatment period, compared to the neutrophil migration prior to the treatment period, or compared to a primary cancer patient not treated with the pharmaceutical composition. In a further embodiment, neutrophil migration is reduced by at least about 5%, 10%, 15%, 20%, 25%, 30%, 35%, 40%, 45%, 50%, 55%, 60%, 65%, 70%, 75%, 80%, 85%, or 90% during the treatment period or subsequent to the treatment period, as compared to the neutrophil migration in the primary cancer prior to the treatment period. Neutrophil migration in one embodiment, is measured by immunofluorescence staining.

In one embodiment of a method provided herein, neutrophil migration, during the treatment period or subsequent to the treatment period, is reduced by from about 10% to about 80%, compared to the neutrophil migration prior to the treatment period, or compared to the neutrophil migration in a patient not administered the pharmaceutical composition. In a further embodiment, neutrophil migration, during the treatment period or subsequent to the treatment period, is reduced by from about 10% to about 70%, compared to the neutrophil migration prior to the treatment period, or as compared to the neutrophil migration in a patient not administered the pharmaceutical composition. In even a further embodiment, neutrophil migration, during the treatment period or subsequent to the treatment period, is reduced by from about 10% to about 60%, compared to the neutrophil migration prior to the treatment period, or compared to the neutrophil migration in a patient not administered the pharmaceutical composition. In yet a further embodiment, neutrophil migration, during the treatment period or subsequent to the treatment period, is reduced by from about 10% to about 50%, compared to the neutrophil migration prior to the treatment period, or compared to the neutrophil migration in a patient not administered the pharmaceutical composition. In even yet a further embodiment, neutrophil migration, during the treatment period or subsequent to the treatment period, is reduced by from about 10% to about 40%, compared to the neutrophil migration prior to the treatment period, or compared to the neutrophil migration in a patient not administered the pharmaceutical composition.

Provided herein are methods for treating a primary cancer or a metastasis of a cancer comprising in part, administering to a patient in need of treatment a CTSC inhibitor, for example a compound of Formula (I) (e.g., brensocatib). The treating inhibits, slows, or reverses the progression of the primary cancer or the metastasis.

In one embodiment, the method further comprises decreasing interleukin 1 beta (IL-1β levels in the patient during the treatment period or subsequent to the treatment period, compared to the IL-1β levels prior to the treatment period, or compared to a patient not administered the pharmaceutical composition. In one embodiment, the IL-1β levels in the patient are reduced during the treatment period or subsequent to the treatment period by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 65%, at least about 70%, at least about 75%, at least about 80%, at least about 85%, at least about 90% as compared to the IL-1β levels in the patient prior to the treatment period, or compared to a patient not administered the pharmaceutical composition. In another embodiment, the method comprises decreasing the IL-1β levels in the patient during the treatment period or subsequent to the treatment period by from about 5% and about 25%, from about 25% and about 50%, from about 50% and about 75%, from about 25% and about 75%, or from about 5% and about 75%, compared to the IL-1β levels in the patient prior to the treatment period, or compared to a patient not administered the pharmaceutical composition.

In one embodiment, decreasing the IL-1β levels comprises decreasing the IL-1β levels at the site of the primary cancer or the site of metastasis. In one embodiment, decreasing the IL1β levels comprises decreasing circulating IL1β levels.

The methods of the invention, in one embodiment, further comprise decreasing circulating levels of a chemotactic factor. In a further embodiment, the chemotactic factor is interleukin 6 (IL-6), C—C Motif Chemokine Ligand 3 (CCL3), or RELA (p65). In one embodiment of the metastasis treatment method provided herein, the method further comprises decreasing the level of a chemotactic factor during the treatment period or subsequent to the treatment period, compared to the level of the chemotactic factor prior to the treatment period. In one embodiment, the chemotactic factor level in the patient is reduced during the treatment period or subsequent to the treatment period by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 65%, at least about 70%, at least about 75%, at least about 80%, at least about 85%, at least about 90% as compared to the chemotactic factor level in the patient prior to the treatment period, or compared to a patient not administered the pharmaceutical composition. In another embodiment, the method comprises decreasing the chemotactic factor levels in the patient during the treatment period or subsequent to the treatment period by from about 5% and about 25%, from about 25% and about 50%, from about 50% and about 75%, from about 25% and about 75%, or from about 5% and about 75%, compared to the chemotactic factor level in the patient prior to the treatment period, or compared to a patient not administered the pharmaceutical composition.

In one embodiment of the metastasis treatment method provided herein, the volume of the primary cancer or the metastasis in the patient is reduced during the treatment period or subsequent to the treatment period, compared to the volume of the primary cancer or the metastasis prior to the treatment period. The reduction in volume, in one embodiment, is from about 5% to about 75%. In a further embodiment, the reduction in tumor volume (primary tumor or secondary tumor, is from about 25% to about 50% or from about 50% to about 75% during the treatment period or subsequent to the treatment period, compared to the tumor volume prior to the treatment period. In another embodiment, the reduction in tumor volume, is by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 65%, at least about 70%, at least about 75%, at least about 80%, at least about 85%, at least about 90%, or at least about 95%, during the treatment period or subsequent to the treatment period, compared to the tumor volume prior to the treatment period.

In one embodiment of the method for a primary cancer provided herein, the progression of the primary cancer regresses. In a further embodiment, regression of the primary cancer occurs during the treatment period or subsequent to the treatment period. For example, in one embodiment, metastasis regression is detected at about 1 month, at about 2 months, at about 3 months, at about 4 months, at about 5 months, at about 6 months, at about 7 months, at about 8 months, at about 9 months, at about 10 months, at about 11 months, or at about 1 year subsequent to the treatment period commencing.

In one embodiment of the method for treating metastasis provided herein, the progression of metastasis regresses. In a further embodiment, regression of the metastasis occurs during the treatment period or subsequent to the treatment period. For example, in one embodiment, metastasis regression is detected at about 1 month, at about 2 months, at about 3 months, at about 4 months, at about 5 months, at about 6 months, at about 7 months, at about 8 months, at about 9 months, at about 10 months, at about 11 months, or at about 1 year subsequent to the treatment period commencing.

The methods provided herein, in one embodiment, further comprise improving the survival rate of the patient. The survival rate, in one embodiment, is increased relative to that of a patient (i.e., a primary cancer patient or a metastasis patient) not administered the pharmaceutical composition. In one embodiment, the survival rate of a patient subjected to one of the methods provided herein, is increased by an average of 1, 2, 3, 4, 5, 6, 7, 8, 9, 10, 11, 12, 13, 14, 15, 16, 17, 18, 19, 20, 21, 22, 23, or 24 months relative to that of a metastasis patient not administered the pharmaceutical composition.

In yet another embodiment, the method comprises reducing tumorsphere size in the primary cancer or the metastasis during the treatment period or subsequent to the treatment period, as compared to the tumorsphere size prior to the treatment period. In a further embodiment, the tumorsphere size is reduced by at least about 10%, at least about 20%, at least about 30%, at least about 40%, at least about 50%, at least about 60%, at least about 70%, at least about 80%, or at least about 90% during the treatment period or subsequent to the treatment period, as compared to the tumorsphere size prior to the treatment period. In some embodiments, tumorsphere size is measured by imaging.

Exemplary Embodiments

Embodiment 1. Use of a cathepsin C inhibitor or a composition comprising a cathepsin C inhibitor, for treating or inhibiting a primary tumor or a metastasis in a patient in need thereof.

Embodiment 2. The use of Embodiment 1, wherein the cathepsin C inhibitor is a compound of Formula (I), or a pharmaceutically acceptable salt thereof:

(I)

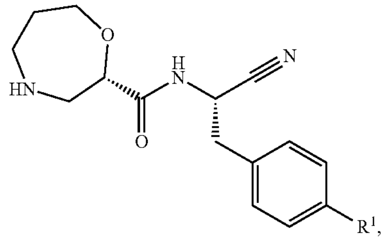

wherein:

$R^1$ is

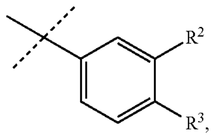

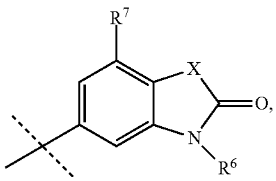

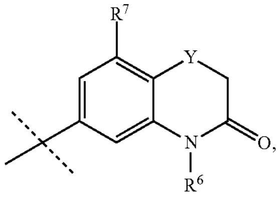

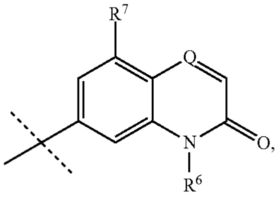

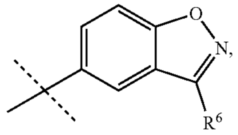

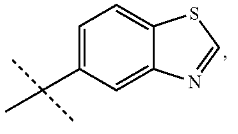

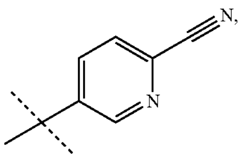

or

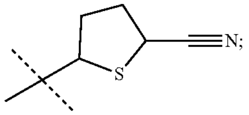

$R^2$ is selected from the group consisting of H, F, Cl, Br, $OSO_2(C_{1-3})$alkyl, and $(C_{1-3})$alkyl;

$R^3$ is hydrogen, F, Cl, Br, CN, $CF_3$, $SO_2CC_{1-3}$alkyl, $CONH_2$ or $SO_2NR^4R^5$, wherein $R^4$ and $R^5$ together with the nitrogen atom to which they are attached form an azetidine, pyrrolidine or piperidine ring;

X is O, S, or $CF_2$;

Y is O or S;

Q is CH or N;

$R^6$ is $(C_{1-3})$alkyl, wherein the $(C_{1-3})$alkyl is optionally substituted with one, two, or three fluorine atoms, and wherein the $(C_{1-3})$alkyl group is optionally substituted with a substituent selected from OH, $O(C_{1-3})$alkyl, $N[(C_{1-3})alkyl]_2$, cyclopropyl, or tetrahydropyranyl; and $R^7$ is H, F, Cl, or $CH_3$.

Embodiment 3. The use of Embodiment 1, wherein the cathepsin C inhibitor is brensocatib.

Embodiment 4. The use of Embodiment 1, wherein the cathepsin C inhibitor is an inhibitor set forth in Table 1, or a pharmaceutically acceptable salt thereof.

Embodiment 5. The use of any one of Embodiments 1-4, for treating or inhibiting a primary tumor.

Embodiment 6. The use of any one of Embodiments 1-4, for treating or inhibiting a metastasis.

Embodiment 7. The use of Embodiment 6, wherein the metastasis is lung metastasis of breast cancer, liver metastasis of breast cancer, bone metastasis of breast cancer, brain metastasis of breast cancer, bone metastasis of lung cancer, liver metastasis of pancreatic cancer, and liver metastasis of gastric cancer.

Embodiment 8. The use of Embodiment 6, wherein the metastasis is lung metastasis of breast cancer, liver metastasis of breast cancer, bone metastasis of breast cancer, or bone metastasis of lung cancer.

Embodiment 9. The use of Embodiment 6, wherein tumor metastasis is of a breast cancer.

Embodiment 10. The use of Embodiment 9, wherein the breast cancer is luminal breast cancer, human epidermal growth factor receptor 2 (HER2) positive breast cancer, or triple-negative breast cancer.

Embodiment 11. The use of Embodiment 6, wherein the metastasis is of a lung cancer.

Embodiment 12. The use of Embodiment 11, wherein the lung cancer is non-small cell lung cancer or small cell lung cancer.

Embodiment 13. The use of Embodiment 5, wherein the primary cancer is a lung cancer.

Embodiment 14. The use of Embodiment 5, wherein the primary cancer is a liver cancer.

Embodiment 15. The use of Embodiment 5, wherein the primary cancer is a breast cancer.

Embodiment 16. The use of any one of Embodiments 1-15, characterized in that the inhibitor or the composition is administered orally.

Embodiment 17. The use of any one of Embodiments 1-15, characterized in that the inhibitor or the composition is administered non-orally.

Embodiment 18. The use of any one of Embodiments 1-17, wherein the patient has elevated serological levels of cathepsin C (CTSC) protein and the treating or inhibiting comprises reducing the elevated serological levels of CTSC protein by at least about 25%.

Embodiment 19. The use of any one of Embodiments 1-17, wherein the patient has elevated serological levels of cathepsin C (CTSC) protein and the treating or inhibiting comprises reducing the elevated serological levels of CTSC protein by from about 25% to about 75%.

Embodiment 20. A method of treating a metastasis of a cancer in a patient in need thereof, comprising, administering to the patient in need of treatment for a treatment period, a pharmaceutical composition comprising an effective amount of a CTSC inhibitor, wherein the treating inhibits, slows, or reverses the progression of the tumor metastasis in the patient.

Embodiment 21. A method of treating a primary cancer in a patient in need thereof, comprising, administering to the patient in need of treatment for a treatment period, a pharmaceutical composition comprising an effective amount of a CTSC inhibitor, wherein the treating inhibits, slows, or reverses the progression of the primary cancer in the patient.

Embodiment 22. The method of Embodiment 20 or 21, wherein the CTSC inhibitor is one of the following compounds.

| Compound | Structural formula |
|---|---|
| BI-9740 | 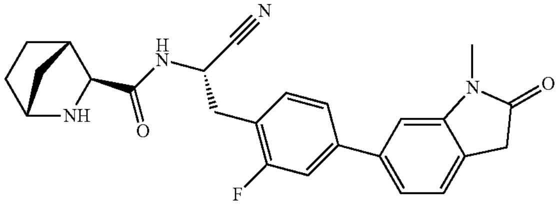 [SMILES: CN1C(=O)Cc2ccc(-c3ccc(C[C@@H](C#N)NC(=O)[C@H]4N[C@@H]5CC[C@H]4C5)c(F)c3)cc21] |
| GSK-2793660 | 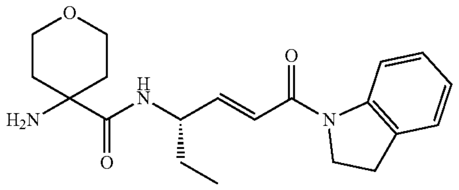 [SMILES: CC[C@@H](/C=C/C(=O)N1CCc2ccccc21)NC(=O)C1(N)CCOCC1] |
| Gly-Phe-CHN2 | 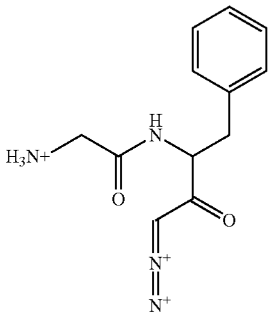 [SMILES: [NH2+]=[N+]=CC(=O)C(Cc1ccccc1)NC(=O)C[NH3+]] |
| IcatC$_{XPZ-01}$ | 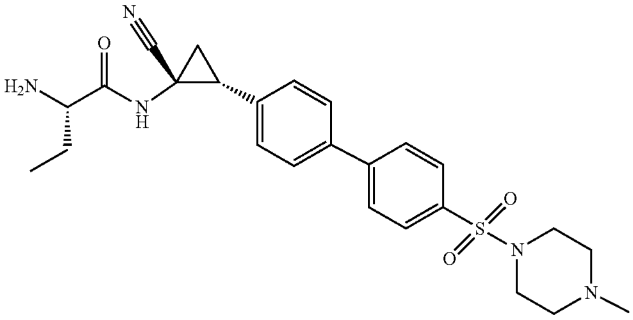 [SMILES: CC[C@H](N)C(=O)N[C@]1(C#N)C[C@@H]1c1ccc(-c2ccc(S(=O)(=O)N3CCN(C)CC3)cc2)cc1] |
| Compound 1, U.S. Pat. No. 8,877,775 | 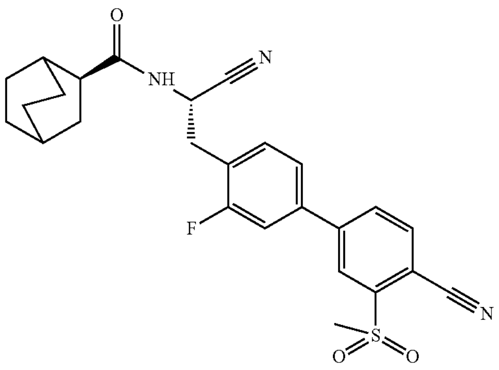 [SMILES: CS(=O)(=O)c1cc(-c2ccc(C[C@@H](C#N)NC(=O)[C@H]3CC4CCC3CC4)c(F)c2)ccc1C#N] |

-continued
| Compound | Structural formula |
|---|---|
| Compound 1, U.S. Pat. No. 9,440,960 B2 | 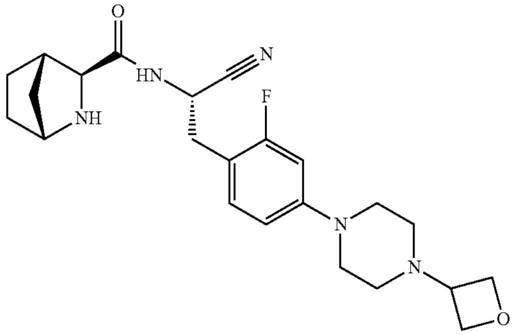 [SMILES: N#C[C@H](Cc1ccc(N2CCN(C3COC3)CC2)cc1F)NC(=O)[C@H]1N[C@@H]2CC[C@H]1C2] |
| Compound 1, U.S. Pat. No. 9,879,026 B2 | 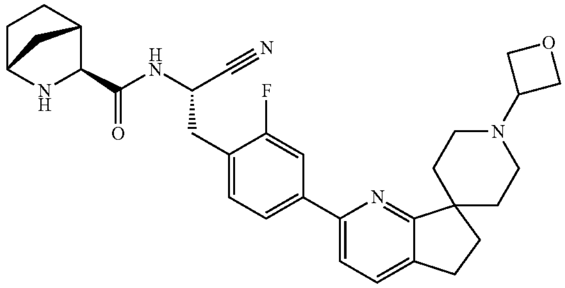 [SMILES: N#C[C@H](Cc1ccc(-c2ccc3c(n2)C2(CC3)CCN(C3COC3)CC2)cc1F)NC(=O)[C@H]1N[C@@H]2CC[C@H]1C2] |
| Compound 25, U.S. Pat. No. 9,879,026 B2 | 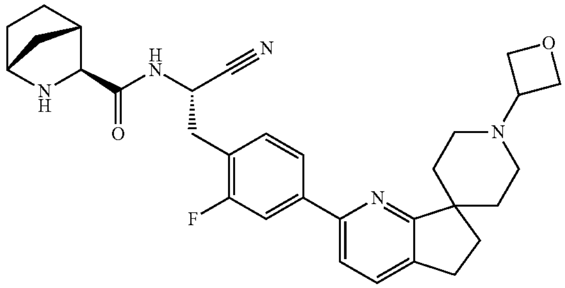 [SMILES: N#C[C@H](Cc1ccc(-c2ccc3c(n2)C2(CC3)CCN(C3COC3)CC2)cc1F)NC(=O)[C@H]1N[C@@H]2CC[C@H]1C2] |
| PZ1018 | 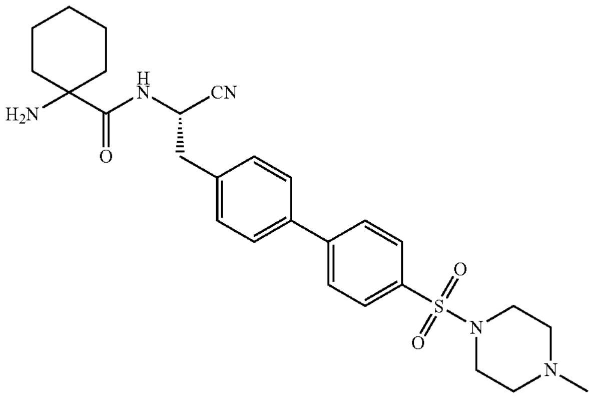 [SMILES: CN1CCN(S(=O)(=O)c2ccc(-c3ccc(C[C@@H](C#N)NC(=O)C4(N)CCCCC4)cc3)cc2)CC1] |

-continued

| Compound | Structural formula |
| --- | --- |
| PZ1025 | 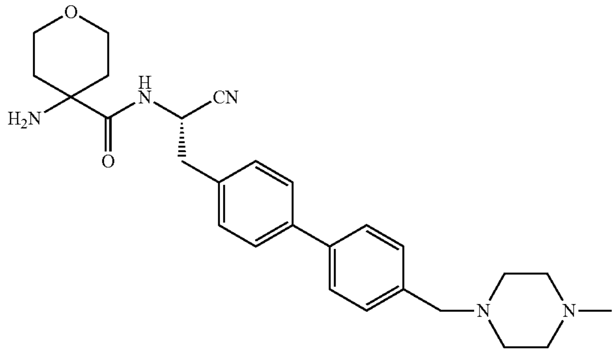 [SMILES: CN1CCN(Cc2ccc(-c3ccc(C[C@@H](C#N)NC(=O)C4(N)CCOCC4)cc3)cc2)CC1] |
| PZ1034 | 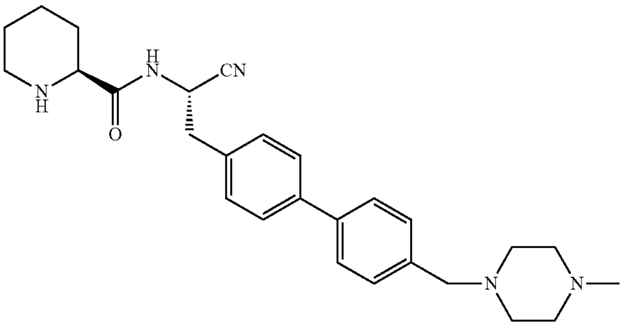 [SMILES: CN1CCN(Cc2ccc(-c3ccc(C[C@@H](C#N)NC(=O)[C@@H]4CCCCN4)cc3)cc2)CC1] |

wherein the treating inhibits, slows, or reverses the progression of the primary cancer in the patient.

Embodiment 23. The method of Embodiment 20 or 21, wherein the CTSC inhibitor is a compound having the structure of Formula (I), or a pharmaceutically acceptable salt thereof:

(I)

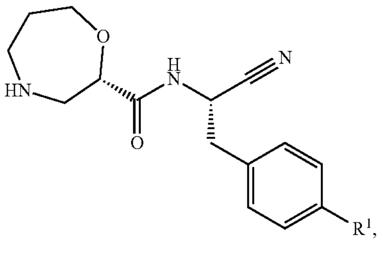

wherein:

$R^1$ is

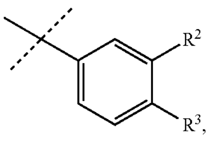

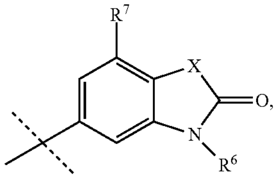

-continued

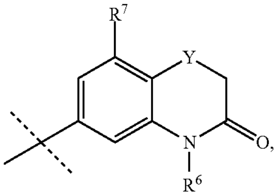

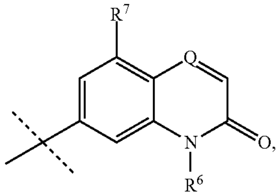

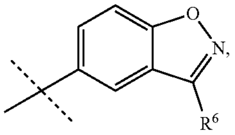

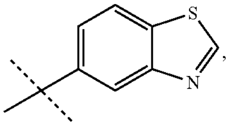

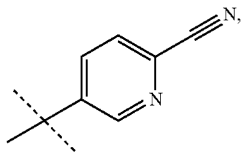

or

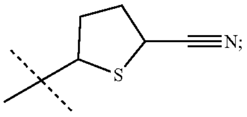

$R^2$ is H, F, Cl, Br, $OSO_2(C_{1-3})$alkyl, or $(C_{1-3})$alkyl;

$R^3$ is hydrogen, F, Cl, Br, CN, $CF_3$, $SO_2C_{1-3}$alkyl, $CONH_2$ or $SO_2NR^4R^5$, wherein $R^4$ and $R^5$ together with the nitrogen atom to which they are attached form an azetidine, pyrrolidine or piperidine ring;

X is O, S, or $CF_2$;

Y is O or S;

Q is CH or N;

$R^6$ is $(C_{1-3})$alkyl, wherein the $(C_{1-3})$alkyl is optionally substituted with one, two, or three fluorine atoms, and wherein the $(C_{1-3})$alkyl group is optionally substituted with a substituent selected from OH, $O(C_{1-3})$alkyl, $N[(C_{1-3})alkyl]_2$, cyclopropyl, or tetrahydropyranyl; and $R^7$ is H, F, Cl, or $CH_3$.

$R^7$ is H, F, Cl, or $CH_3$.

Embodiment 24. The method of Embodiment 23, wherein, $R^1$ is

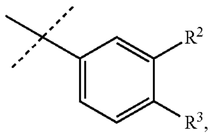

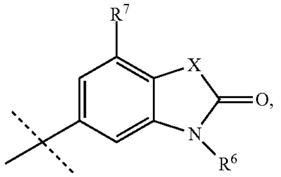

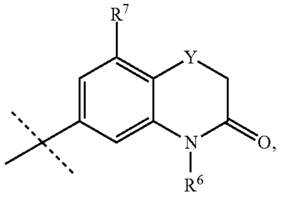

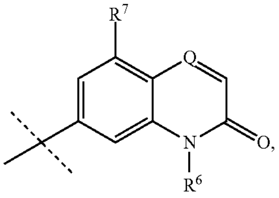

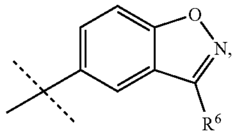

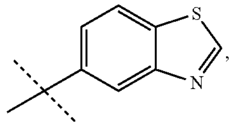

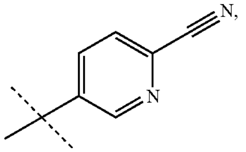

or

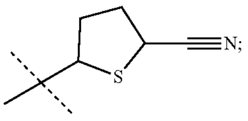

X is O, S or $CF_2$;

Y is O or S;

Q is CH or N;

$R^6$ is $C_{1-3}$alkyl, wherein the $C_{1-3}$alkyl is optionally substituted by 1, 2 or 3 F and optionally by one substituent selected from the group consisting of OH, $OC_{1-3}$alkyl, $N(C_{1-3}alkyl)_2$, cyclopropyl, and tetrahydropyran; and $R^7$ is hydrogen, F, Cl or $CH_3$.

Embodiment 25. The method of Embodiment 23 or 24, wherein, $R^1$ is

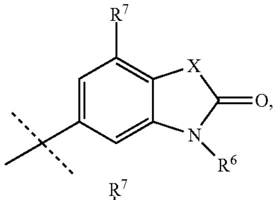

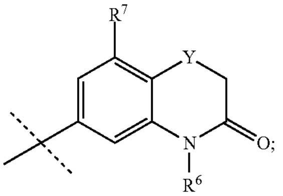

X is O, S or $CF_2$;

Y is O or S;

$R^6$ is $C_{1-3}$alkyl, wherein the $C_{1-3}$alkyl is optionally substituted by 1, 2 or 3 F and optionally by one substituent selected from the group consisting of OH, $OC_{1-3}$alkyl, $N(C_{1-3}alkyl)_2$, cyclopropyl, and tetrahydropyran; and $R^7$ is hydrogen, F, Cl or $CH_3$.

Embodiment 26. The method of any one of Embodiments 23-25, wherein, $R^1$ is

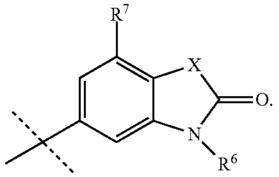

Embodiment 27. The method of Embodiment 26, wherein X is O; $R^6$ is $C_{1-3}$alkyl; and $R^7$ is hydrogen.

Embodiment 28. The method of Embodiment 23, wherein, $R^1$ is

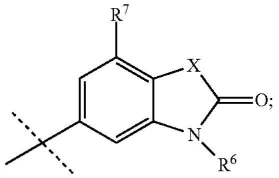

X is O;

$R^6$ is $C_{1-3}$alkyl, wherein the $C_{1-3}$alkyl is optionally substituted by 1, 2 or 3 F; and $R^7$ is hydrogen.

Embodiment 29. The method of Embodiment 23, wherein, $R^1$ is

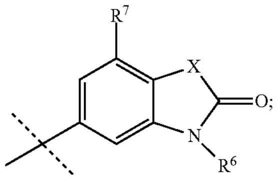

X is O;

$R^6$ is $C_{1-3}$alkyl; and $R^7$ is hydrogen.

Embodiment 30. The method of Embodiment 26, wherein X is O, S, and $CF_2$; $R^6$ is $(C_{1-3})$alkyl, wherein the $C_{1-3}$alkyl is optionally substituted with one, two, or three fluorine atoms; and $R^7$ is H.

Embodiment 31. The method of Embodiment 23, wherein the compound of Formula (I) is brensocatib, or a pharmaceutically acceptable salt thereof.

Embodiment 32. The method of Embodiment 23, wherein the compound of Formula (I) is brensocatib.

Embodiment 33. The method of Embodiment 23, wherein the compound of Formula (I) is (2S)—N-[(1S)-1-Cyano-2-(4'-cyanobiphenyl-4-yl)ethyl]-1,4-oxazepane-2-carboxamide;

(2S)—N-{(1S)-1-Cyano-2-[4-(3-methyl-2-oxo-2,3-dihydro-1,3-benzoxazol-5-yl)phenyl]ethyl}-1,4-oxazepane-2-carboxamide;

(2S)—N-{(1S)-1-Cyano-2-[4-(3,7-dimethyl-2-oxo-2,3-dihydro-1,3-benzoxazol-5-yl)phenyl]ethyl}-1,4-oxazepane-2-carboxamide;

4'-[(2S)-2-Cyano-2-{[(2S)-1,4-oxazepan-2-ylcarbonyl]amino}ethyl]biphenyl-3-yl methanesulfonate;

(2S)—N-{(1S)-1-Cyano-2-[4-(3-methyl-1,2-benzoxazol-5-yl)phenyl]ethyl}-1,4-oxazepane-2-carboxamide;

(2S)—N-{(1S)-1-Cyano-2-[4'-(trifluoromethyl)biphenyl-4-yl]ethyl}-1,4-oxazepane-2-carboxamide;

(2S)—N-[(1S)-1-Cyano-2-(3',4'-difluorobiphenyl-4-ylp-ethyl]-1,4-oxazepane-2-carboxamide;

(2S)—N-{(1S)-1-Cyano-2-[4-(6-cyanopyridin-3-yl)phenyl]ethyl}-1,4-oxazepane-2-carboxamide;

(2S)—N-{(1S)-1-Cyano-2-[4-(4-methyl-3-oxo-3,4-dihydro-2H-1,4-benzothiazin-6-yl)phenyl]ethyl}-1,4-oxazepane-2-carboxamide;

(2S)—N-{(1S)-1-Cyano-2[4-(3-ethyl-7-methyl-2-oxo-2,3-dihydro-1,3-benzoxazol-5-yl)phenyl]ethyl}-1,4-oxazepane-2-carboxamide;

(2S)—N-[(1S)-1-Cyano-2-{4-[3-(2-hydroxy-2-methylpropyl)-2-oxo-2,3-dihydro-1,3-benzoxazol-5-yl]phenyl}ethyl]-1,4-oxazepane-2-carboxamide;

(2S)—N-[(1S)-1-Cyano-2-{4-[3-(2,2-difluoroethyl)-7-fluoro-2-oxo-2,3-dihydro-1,3-benzoxazol-5-yl]phenyl}ethyl]-1,4-oxazepane-2-carboxamide;

(2S)—N-[(1S)-1-Cyano-2-(4-{3-[2-(dimethylamino)ethyl]-2-oxo-2,3-dihydro-1,3-benzoxazol-5-yl}phenyl)ethyl]1,4-oxazepane-2-carboxamide;

(2S)—N-{(1S)-1-Cyano-2-[4-(3,3-difluoro-1-methyl-2-oxo-2,3-dihydro-1H-indol-6-yl)phenyl]ethyl}-1,4-oxazepane-2-carboxamide;

(2S)—N-{(1S)-1-Cyano-2-[4-(7-fluoro-3-methyl-2-oxo-2,3-dihydro-1,3-benzoxazol-5-yl)phenyl]ethyl}-1,4-oxazepane-2-carboxamide;

(2S)—N-{(1S)-1-Cyano-2-[4-(3-ethyl-2-oxo-2,3-dihydro-1,3-benzoxazol-5-yl)phenyl]ethyl}-1,4-oxazepane-2-carboxamide;

(2S)—N-[(1S)-1-Cyano-2-{4-[3-(cyclopropylmethyl)-2-oxo-2,3-dihydro-1,3-benzoxazol-5-yl]phenyl}ethyl]-1,4-oxazepane-2-carboxamide;

(2S)—N-[(1S)-1-Cyano-2-{4-[3-(2-methoxyethyl)-2-oxo-2,3-dihydro-1,3-benzothiazol-5-yl]phenyl}ethyl]-1,4-oxazepane-2-carboxamide;

(2S)—N-[(1S)-1-Cyano-2-{4-[2-oxo-3-(propan-2-yl)-2,3-dihydro-1,3-benzoxazol-5-yl]phenyl}ethyl]-1,4-oxazepane-2-carboxamide;

(2S)—N-{(1S)-1-Cyano-2-[4-(4-methyl-3-oxo-3,4-dihydro-2H-1,4-benzoxazin-6-yl)phenyl]ethyl}-1,4-oxazepane-2-carboxamide;

(2S)—N-[(1S)-1-Cyano-2-{4-[3-(2-methoxyethyl)-2-oxo-2,3-dihydro-1,3-benzoxazol-5-yl]phenyl}ethyl]-1,4-oxazepane-2-carboxamide;

(2S)—N-{(1S)-1-Cyano-2[4-(5-cyanothiophen-2-yl)phenyl]ethyl}-1,4-oxazepane-2-carboxamide;

(2S)—N-[(1S)-2-(4'-Carbamoyl-3'-fluorobiphenyl-4-yl)-1-cyanoethyl]1,4-oxazepane-2-carboxamide;

(2S)—N {(1S)-1-Cyano-2-[4-(1-methyl-2-oxo-1,2-dihydroquinolin-7-yl)phenyl]ethyl}-1,4-oxazepane-2-carboxamide;

(2S)—N-[(1S)-1-Cyano-2-{4-[2-oxo-3-(tetrahydro-2H-pyran-4-ylmethyl)-2,3-dihydro-1,3-benzoxazol-5-yl]phenyl}ethyl]-1,4-oxazepane-2-carboxamide;

(2S)—N-{(1S)-2-[4-(7-Chloro-3-methyl-2-oxo-2,3-dihydro-1,3-benzoxazol-5-yl)phenyl]-1-cyanoethyl}-1,4-oxazepane-2-carboxamide;

(2S)—N-[(1S)-1-Cyano-2-{4-[3-(2,2-difluoroethyl)-2-oxo-2,3-dihydro-1,3-benzoxazol-5-yl]phenyl}ethyl]-1,4-oxazepane-2-carboxamide;

(2S)—N-[(1S)-1-Cyano-2-{4-[2-oxo-3-(2,2,2-trifluoroethyl)-2,3-dihydro-1,3-benzoxazol-5-yl]phenyl}ethyl]-1,4-oxazepane-2-carboxamide;

(2S)—N-{(1S)-1-Cyano-2-[4-(3-methyl-2-oxo-2,3-dihydro-1,3-benzothiazol-5-yl)phenyl]ethyl}-1,4-oxazepane-2-carboxamide;

(2S)—N-{(1S)-1-Cyano-2-[4'-(methylsulfonyl)biphenyl-4-yl]ethyl}-1,4-oxazepane-2-carboxamide;

(2S)—N-{(1S)-2-[4'-(Azetidin-1-ylsulfonyl)biphenyl-4-yl]-1-cyanoethyl}-1,4-oxazepane-2-carboxamide;

(2S)—N-[(1S)-1-Cyano-2-(4'-fluorobiphenyl-4-yl)ethyl]-1,4-oxazepane-2-carboxamide;

(2S)—N-{(1S)-2-[4-(1,3-Benzothiazol-5-yl)phenyl]-1-cyanoethyl}-1,4-oxazepane-2-carboxamide;

(2S))—N-[(1S)-1-Cyano-2-(4'-cyanobiphenyl-4-yl)ethyl]-1,4-oxazepane-2-carboxamide; or a pharmaceutically acceptable salt thereof.

Embodiment 34. The method of any one of Embodiments 20-33, wherein the administering of the pharmaceutical composition is by oral administration.

Embodiment 35. The method of any one of Embodiments 20-33, wherein the administering of the pharmaceutical composition is by parenteral administration.

Embodiment 36. The method of any one of Embodiments 20-33, wherein the administering of the pharmaceutical composition is by intravenous administration.

Embodiment 37. The method of any one of Embodiments 20-33, wherein the administering of the pharmaceutical composition is by infusion.

Embodiment 38. The method of any one of Embodiments 20-33, wherein the pharmaceutical composition is in tablet form.

Embodiment 39. The method of any one of Embodiments 20-34, wherein the pharmaceutical composition further comprises a tablet coating.

Embodiment 40. The method of any one of Embodiments 20-39, wherein the compound of Formula (I) is present from about 5 milligrams (mg) to about 70 mg in the pharmaceutical composition.

Embodiment 41. The method of any one of Embodiments 20-39, wherein the compound of Formula (I) is present from about 10 milligrams (mg) to about 60 mg in the pharmaceutical composition.

Embodiment 42. The method of any one of Embodiments 20-39, wherein the compound of Formula (I) is present from about 10 milligrams (mg) to about 40 mg in the pharmaceutical composition.

Embodiment 43. The method of any one of Embodiments 20-39, wherein the compound of Formula (I) is present at about 10 milligrams (mg) in the pharmaceutical composition.

Embodiment 44. The method of any one of Embodiments 20-39, wherein the compound of Formula (I) is present at about 25 milligrams (mg) in the pharmaceutical composition.

Embodiment 45. The method of any one of Embodiments 20-39, wherein the compound of Formula (I) is present at about 40 milligrams (mg) in the pharmaceutical composition.

Embodiment 46. The method of any one of Embodiments 20-39, wherein the compound of Formula (I) is present at about 60 milligrams (mg) in the pharmaceutical composition.

Embodiment 47. The method of any one of Embodiments 20-46, wherein the administering is carried out once per day throughout the treatment period.

Embodiment 48. The method of any one of Embodiments 20-46, wherein the administering is carried out twice per day throughout the treatment period.

Embodiment 49. The method of any one of Embodiments 20-46, wherein the administering is carried out every other day throughout the treatment period.

Embodiment 50. The method of any one of Embodiments 20-46, wherein the administering is carried out every third day throughout the treatment period.

Embodiment 51. The method of any one of Embodiments 20-50, wherein the treatment period is at least one month.

Embodiment 52. The method of any one of Embodiments 20-50, wherein the treatment period is at least two months.

Embodiment 53. The method of any one of Embodiments 20-50, wherein the treatment period is at least three months.

Embodiment 54. The method of any one of Embodiments 20-50, wherein the treatment period is at least six months.

Embodiment 55. The method of any one of Embodiments 20-50, wherein the treatment period is from about six months to about 24 months.

Embodiment 56. The method of Embodiment 55, wherein the treatment period is from about six months to about 18 months.

Embodiment 57. The method of Embodiment 55, wherein the treatment period is from about six months to about 12 months.

Embodiment 58. The method of Embodiment 55, wherein the treatment period is from about 12 months to about 24 months.

Embodiment 59. The method of Embodiment 55, wherein the treatment period is from about 12 months to about 18 months.

Embodiment 60. The method of any one of Embodiments 20-59, wherein the patient presents with elevated serological levels of cathepsin C (CTSC) protein prior to the treatment period.

Embodiment 61. The method of Embodiment 60, wherein the elevated serological levels of CTSC protein are reduced by at least about 25% after during or subsequent to the treatment period.

Embodiment 62. The method of Embodiment 60, wherein the elevated serological levels of CTSC protein are reduced by at least about 50% after during or subsequent to the treatment period.

Embodiment 63. The method of Embodiment 60, wherein the elevated serological levels of CTSC protein are reduced by at least about 75% after during or subsequent to the treatment period.

Embodiment 64. The method of Embodiment 60, wherein the elevated serological levels of CTSC protein are reduced by from about 25% to about 75%, during or subsequent to the treatment period.

Embodiment 65. The method of any one of Embodiments 20-64, wherein the patient is a human.

Embodiment 66. The method of any one Embodiments 20 and 22-65, wherein the patient experiences regression of the metastasis after the treatment period or during the treatment period.

Embodiment 67. The method of any one Embodiments 21-65, wherein the patient experiences regression of the primary cancer after the treatment period or during the treatment period.

Embodiment 68. The method of Embodiment 66 or 67, wherein the regression of the occurs about two months or about three months into the treatment period.

Embodiment 69. The method of Embodiment 66 or 67, wherein the regression occurs about six months into the treatment period.

Embodiment 69. The method of any one of Embodiments 20, 22-66 and 68-69, wherein the metastasis is of a breast cancer.

Embodiment 70. The method of Embodiment 69, wherein the metastasis of a breast cancer is a lung metastasis of a breast cancer, liver metastasis of a breast cancer, bone metastasis of a breast cancer or brain metastasis of a breast cancer.

Embodiment 71. The method of Embodiment 70, wherein the metastasis of a breast cancer is lung metastasis of a breast cancer.

Embodiment 72. The method of any one of Embodiments 69-71, wherein the breast cancer is luminal breast cancer, human epidermal growth factor receptor 2 (HER2) positive breast cancer, or triple-negative breast cancer.

Embodiment 73. The method of any one of Embodiments 20, 22-66 and 68-69, wherein the metastasis is a bone metastasis of lung cancer, a liver metastasis of pancreatic cancer, or a liver metastasis of gastric cancer.

Embodiment 74. The method of any one of Embodiments 20, 22-66 and 68-69, wherein the metastasis is a lung metastasis of breast cancer, a liver metastasis of breast cancer, a bone metastasis of breast cancer, a brain metastasis of breast cancer, a bone metastasis of lung cancer, a liver metastasis of colon cancer, a liver metastasis of pancreatic cancer, or a liver metastasis of gastric cancer.

Embodiment 75. The method of any one of Embodiments 20, 22-66 and 68-69, wherein the metastasis is of a lung cancer.

Embodiment 76. The method of Embodiment 75, wherein the lung cancer is non-small cell lung cancer.

Embodiment 77. The method of Embodiment 75, wherein the lung cancer is small cell lung cancer.

Embodiment 78. The method of any one of Embodiments 20, 22-66 and 68-69, wherein the metastasis is a metastasis of a pancreatic cancer or a gastric cancer.

Embodiment 79. The method of any one of Embodiments 20, 22-66 and 68-69, wherein the metastasis is a metastasis of a bone cancer, liver cancer, stomach cancer, colon cancer, rectal cancer or a colorectal cancer.

Embodiment 80. The method of any one Embodiments 21-65 and 67-69, wherein the primary cancer is a lung cancer.

Embodiment 81. The method of any one Embodiments 21-65 and 67-69, wherein the primary cancer is a breast cancer.

Embodiment 82. The method of any one Embodiments 21-65 and 67-69, wherein the primary cancer is a liver cancer.

Embodiment 83. The method of Embodiment 80, wherein the lung cancer is small cell lung cancer.

Embodiment 84. The method of Embodiment 80, wherein the lung cancer is non-small cell lung cancer.

Embodiment 85. The method of Embodiment 81, wherein the breast cancer is luminal breast cancer, human epidermal growth factor receptor 2 (HER2) positive breast cancer, or triple-negative breast cancer.

Embodiment 86. The method of any one of Embodiments 20-85, wherein treating further comprises reducing circulating levels of interleukin 1 beta (IL-1β) in the patient during the treatment period or subsequent to the treatment period, compared to the circulating levels of IL-1β of the patient prior to the treatment period.

Embodiment 88. The method of any one of Embodiments 20, 22-66, 68-79 and 86, wherein the volume of the metastasis is reduced by from about 5% to about 25% during the treatment period or subsequent to the treatment period, compared to the volume of the metastasis prior to the treatment period.

Embodiment 89. The method of any one of Embodiments 20, 22, 24-66, 68-79 and 86, wherein the volume of the metastasis is reduced by from about 25% to about 50% during the treatment period or subsequent to the treatment period, compared to the volume of the metastasis prior to the treatment period.

Embodiment 90. The method of any one of Embodiments 20, 22, 24-66, 68-79 and 86, wherein the volume of the metastasis is reduced by from about 50% to about 75% during the treatment period or subsequent to the treatment period, compared to the volume of the metastasis prior to the treatment period.

Embodiment 91. The method of any one of Embodiments 21-65, 67-69 and 80-86, wherein the volume of the primary cancer is reduced by from about 5% to about 25% during the treatment period or subsequent to the treatment period, compared to the volume of the primary cancer prior to the treatment period.

Embodiment 92. The method of any one of Embodiments 21-65, 67-69 and 80-86, wherein the volume of the primary cancer is reduced by from about 25% to about 50% during the treatment period or subsequent to the treatment period, compared to the volume of the primary cancer prior to the treatment period.

Embodiment 93. The method of any one of Embodiments 21-65, 67-69 and 80-86, wherein the volume of the primary cancer is reduced by from about 50% to about 75% during the treatment period or subsequent to the treatment period, compared to the volume of the primary cancer prior to the treatment period.

Embodiment 94. The method of any one of Embodiments 20-93, wherein the survival rate of the patient is increased relative to that of a patient not administered the pharmaceutical composition.

Embodiment 95. The method of any one of Embodiments 20-94, wherein the treating further comprises reducing circulating neutrophil extracellular traps (NETs) in in the patient during the treatment period or subsequent to the treatment period, compared to the number of circulating NETs in the patient prior to the treatment period.

Embodiment 96. The method of any one of Embodiments 20-95, wherein the treating further comprises reducing neutrophil migration during the treatment period or subsequent to the treatment period, as compared to the neutrophil migration in the metastasis prior to the treatment period.

Embodiment 97. The method of Embodiment 96, wherein reducing neutrophil migration comprises reducing neutrophil migration by from about 25% to about 75%, as compared to the neutrophil migration in a second patient not administered the pharmaceutical composition.

Embodiment 98. The method of Embodiment 96, wherein reducing neutrophil migration comprises reducing neutrophil migration by from about 25% to about 50%, as compared to the neutrophil migration in a second patient but not administered the pharmaceutical composition.

Embodiment 99. The method of Embodiment 96, wherein reducing neutrophil migration comprises reducing neutrophil migration by at least about 25%, as compared to the neutrophil migration in a second patient but not administered the pharmaceutical composition.

Embodiment 100. The method of Embodiment 96, wherein reducing neutrophil migration comprises reducing neutrophil migration by at least about 50%, as compared to the neutrophil migration in a second patient but not administered the pharmaceutical composition.

Embodiment 101. The method of any one of Embodiments 96-100, wherein the neutrophil migration is measured by immunofluorescence staining.

Embodiment 102. The method of any one of Embodiments 20-101, wherein the treating further comprises reducing neutrophil extracellular traps (NETs) in the patient during the treatment period or subsequent to the treatment period, compared to the number of NETs in the patient prior to the treatment period.

Embodiment 103. The method of Embodiment 102, wherein the number of NETs in the metastasis is reduced by at least 50% compared to the number of NETs in the metastasis prior to the treatment period.

Embodiment 104. The method of Embodiment 102 or 103, wherein the NETs are detected by immunofluorescence staining.

Embodiment 105. The method of any one of Embodiments 20-104, wherein the treating further comprises reducing the expression levels of one or more proteins in the patient, wherein the one or more proteins is cathepsin C (CTSC), interleukin 6 (IL-6), C—C Motif Chemokine Ligand 3 (CCL3), or RELA (p65).

Embodiment 106. The method of any one of Embodiments 20-105, wherein the treating further comprises reducing tumorsphere size in the primary cancer or the metastasis.

Embodiment 107. The method of Embodiment 106, wherein the tumorsphere size is measured by imaging.

EXAMPLES

The present invention is further illustrated by reference to the following Examples. However, it should be noted that the Examples, like the embodiments described above, are illustrative and are not to be construed as restricting the scope of the invention in any way.

Materials and Methods

Unless indicated otherwise, the following materials and methods were used in carrying out the following examples.

Oligonucleotide Sequences and Data

Oligonucleotide sequences used in this study are provided in Table S2. Part of the secretomic profiling data (MDA-MB-231 and its sublines) were published in a previous study (Zhuang et al., "Differential effects on lung and bone metastasis of breast cancer by Wnt signalling inhibitor DKK1," *Nat. Cell Biol.* 19:1274-1285 (2017)). The rest of the data (MCF10CA1h vs. MCF10CA1a; 4T1 series) are provided in this study as Tables S3 and S4 of Xiao et al., "Cathepsin C promotes breast cancer lung metastasis by modulating neutrophil infiltration and neutrophil extracellular trap formation," *Cancer Cell* 29:1-15 (2021), incorporated by reference herein in its entirety for all purposes. The original data in this study have been deposited in Mendeley Data at www(dot)doi(dot)org/10.17632/sb8h3hw84k.1.

Cell Lines

The cell lines generated in this study and their parental cell lines (MDA-MB-231 and its sublines, 4T1 series, AT3) were grown in DMEM with 10% v/v FBS and 100 μg/ml penicillin/streptomycin. MCF10 series cell lines were grown in DMEM/F12 media supplemented with 10 μg/ml insulin, 20 ng/ml EFG, 0.5 μg/ml hydrocortisone, 100 μg/ml penicillin/streptomycin and 20% v/v horse serum. Cell cultures at passages 5-8 were used and tested for mycoplasma contamination every week.

Human Breast Cancer Tissues and Blood Samples

Frozen primary tumor specimens (n=48, 30, 10 for luminal, $HER2^+$, triple negative tumors, respectively) and patient sera (n=46) with following-up information of metastatic status, were obtained from Qilu Hospital of Shandong University with informed patient consent and the approval from Qilu Institutional Review Boards. Among these 88 primary tumor specimens, 58 were also with overall survival information. Paraffin-embedded primary tumors (n=42, 12, 20 for luminal, $HER2^+$, triple negative tumors, respectively) and lung metastases (n=29) were obtained from Shanghai General Hospital with informed consent from all subjects and approval from the Hospital Institutional Research Ethics Committee. Among these 74 primary tumors of Shanghai cohort, 58 samples (30, 9, 19 for luminal, $HER2^+$, triple negative tumors, respectively) were with the follow-up information of metastasis status. The samples with follow-up information were used for Kaplan-Meier analysis of metastasis (n=146) and overall survival (n=58). Whole blood samples for neutrophil isolation were collected from Shanghai Jiao Tong University Affiliated Sixth People's Hospital and Zhongshan Hospital and under exemption-approval of the Center's Institutional Review Board.

Mouse Experiments

Female BALB/c and athymic mice aged 6-10 weeks were used in all animal experiments. Orthotropic and intravenous injection were performed as previously described (Zhuang et al., "Differential effects on lung and bone metastasis of breast cancer by Wnt signalling inhibitor DKK1," *Nat. Cell Biol.* 19:1274-1285 (2017)). For EdU labeling assays, nude mice were intravenously injected with $2\times10^5$ cancer cells, followed by intraperitoneal (i.p.) injection of 100 ng/mouse EdU (ThermoFisher, C10640) 24 h before lung harvest. For neutrophil depletion assays, mice received 2 initial i.p. injection (200 μg/mouse) of 1A8 Ly6G antibody (BE0075-1, BioXCel) or rat IgG control (14131, Sigma) every 3 days before cancer cell injection and then maintenance injection twice a week after cancer cell injection. For Sivelestat or DNase I treatment, mice were i.p. injected with Sivelestat (50 mg/kg) or DNase I (5 mg/kg) 2 h before cancer cell injection, followed by daily injection of the reagents for 9 days, and then maintenance shots twice a week. For GSK484 treatment, mice were treated with GSK484 (20 mg/kg, i.p. daily shots for 20 days from day 7, and then maintenance shots every two days) following orthotopic injection of AT3 or 4T07 cells. For IL-1b blocking or IL6R/CCR1 inhibition assays, mice were orthotopically inoculated with $5\times10^4$ AT3 and treated with i.p. administration of IgG or the IL-1β blocking antibody (100 μg per mouse), or the IL6R blocking antibody (100 μg per mouse) and the CCR1 inhibitor BX471 (20 mg/kg), every two days from day 7 until the mice were sacrificed. For brensocatib treatment, BALB/c mice were orthotopically inoculated with $1\times10^5$ 4T1 cells, and C57/BL6 mice were orthotopically inoculated with $2\times10^5$ AT3. Vehicle controls (0.5% HPMC, 0.1% Tween 80 in 0.1 M citrate buffer, pH 3) and brensocatib (5 mg/kg) were administered orally twice daily until the mice were sacrificed. Orthotopic tumors were surgically removed at the size of about 1 $cm^3$. Recombinant human active PR3 treatment (1.5 mg/kg) was administrated intravenously daily after intravenous inoculation of $1\times^5$ LM2 cells. For TSP-1 degradation assays, mice were i.p. injected with GSK484 (20 mg/kg) 2 h before cancer cell injection and followed by daily treatment. Then, the lungs were perfused with 50 ml of pre-chilled PBS through the right ventricle until they were cleared of blood at 72 h post injection of $3\times10^6$ AT3 or 4T07 cells. BLI was acquired with NightOWL II LB983 Imaging System (Bert-hold) and IVIS Spectrum CT (PerkinElmer). All animal studies were conducted according to the guidelines for the care and use of laboratory animals and were approved by the Institutional Animal Care and Use Committee of Shanghai Institute of Nutrition and Health.

Western Blot

Cultured cells were collected by scraper or trypsinized and then lysed with lysis buffer (50 mM Tris-HCl, 150 mM NaCl, 1% NP-40 detergent, 0.5% sodium deoxycholate, 0.1% SDS with phosphatase and protease inhibitors), and dispersed tissue were homogenized in RIPA buffer on ice for 15 min, followed by centrifugation at 17,000 g for 15 min. The protein concentration was measured with a BCA Protein Assay Kit. Proteins of 10 μg, 80 μg, 30 μg were loaded for membrane proteins, IL-1β processing, p65 phosphorylation and the other assays, respectively, and separated on 8-12% SDS-polyacrylamide gel. For cancer cell conditioned medium (CM) collection, cells were grown to ~80% confluence in 10 cm culture dishes. After three times washing with serum-free medium at 37° C., the cells were incubated in serum-free medium at 37° C. for 24 h. The CM were collected, centrifuged at 2,000 g for 10 min, filtrated by 0.22 μm filters, stored at −80° C. until used. The secreted proteins in CM were collected by TCA precipitation. Briefly, 25% v/v TCA was added into 1 ml CM with phosphatase and protease inhibitors, incubated overnight at 4° C., and then centrifuged at 20,000 g for 60 min, after which the supernatant was discarded and the pellet was washed twice with 1 ml pre-chilled acetone, centrifuged again at 20,000 g for 5 min at 4° C. Dry protein pellet was lysed with the lysis buffer, and separated on 12% SDS-poly-acrylamide gel.

FACS Analysis of Stromal Components in Lung Metastases and Metastatic Niches

The procedure of the stromal content analysis was previously described Zhuang et al., "Differential effects on lung and bone metastasis of breast cancer by Wnt signalling inhibitor DKK1," *Nat. Cell Biol.* 19:1274-1285 (2017)). Briefly, lung metastases were picked, minced, further digested by 5 mg/ml Collagenase Type III (LS004182, Worthington), 0.001% (WN) DNase I (D-4527, Sigma) and 1% (w/w) Dispase (17105-041, Invitrogen) at 37° C. for 1 h. For analysis of immunocytes in the early metastatic niches, the lungs were perfused with 50 ml of PBS through the right ventricle until they were cleared of blood. The single-cell suspension of lung tissues was prepared as above. Then, red blood cells were lysed with RBC lysis reagent (555899, BD Pharmingen). Cells were incubated for 10 min at 4° C. with CD16/CD32 antibody (2.4G2, BD Life Sciences) to block FcR before antibody staining. Flow cytometry was performed by Gallious (Beckman) FACS system and quantified by the FlowJo V10 software.

Neutrophil Isolation

To isolate neutrophil from bone marrow, bone marrow cells from 8 to 12-weeks-old BALB/c mice were harvested in sterile Hank's buffered salt solution (HBSS) without $Ca^{2+}/Mg^{2+}$ (14185052, Invitrogen), and laid on top of a 2-layer Percoll (17089102, GE Healthcare) gradient (72% and 63.5% in HBSS), followed by centrifugation at 1,200 g for 30 min at 25° C. Neutrophils enriched in the interface of 63.5%-72% fractions were confirmed to be of >95% purity by flow cytometry analysis. To isolate neutrophils from peripheral blood of mice, whole blood was collected via cardiac puncture (1 ml per animal) and suspended in HBSS (2 ml per animal) with 15 mM EDTA. After centrifugation (400 g, 10 min, 4° C.), white cells were resuspended in 2 ml HBSS with 2 mM EDTA. Then, the cells were centrifuged (1500 g, 30 min, room temperature) in a three-layer Percoll gradient (78%, 69%, and 52%) without braking. Neutrophils enriched in the interface of 69% and 78% layers were confirmed to be of >95% purity by flow cytometric analysis. Human neutrophils were isolated from peripheral blood of healthy female volunteers and breast cancer patients by density gradient separation using Polymorphprep (1114683, Axis-Shield) and centrifuging at 500 g for 30 min at room temperature. The purity of the isolated neutrophils was determined by May-Grunwald-Giemsa staining (40751ES02, Yea-sen). Unless noted otherwise, neutrophils were cultured in RPMI 1640 medium containing 0.2% BSA.

In Vitro NET Analysis

To assess NET formation, neutrophils ($2.5\times10^5$ cells) were seeded on coverslips coated with poly-L-lysine (P4707, Sigma) in 24-well plates for 30 min before adding 10% cancer cell CM, Sivelestat (10 μM), PMA (20 nM, Sigma), Cl-amidine (100 μM, Selleck) and/or DNase I (1 μg/ml). After 12 to 16 h at 37° C., neutrophils were fixed with 4% paraformaldehyde (PFA) for 10 min at room temperature, washed twice with PBS and permeabilized in 0.1% Triton X-100 for 5 min. Cells were blocked in PBS containing 5% BSA for 30 min, then incubated with anti-histone H3 (1:50, 3680, CST) and anti-NE (1:100, ab68672, ABCAM), or anti-MPO (1:400, AF3667, R&D) and Ci-H3 (1:200, ab5103, ABCAM) in blocking buffer overnight at 4° C. After three washes in PBS, cells were incubated with fluoro-chrome-conjugated secondary antibodies (1:500, Invitrogen) for 1 h, and then counterstained with DAPI (Roche, 10236276001) before mounting (Dako, S3023). Observation and photographing were performed with the confocal microscopy Cell Observer (ZEISS, Germany), and image processing and analysis were performed with Zen blue edition software (ZEISS, Germany). NET area quantification was performed using the DANA method (Rebernick et al., "DNA area and NETosis analysis (DANA): a high-throughput method to quantify neutrophil extracellular traps in fluorescent microscope images," *Biol. Proced. Online* 20:7 (2018)). Briefly, the areas of structures depicting NET morphology and positive for Ci-H3 or total H3 were counted as NETotic cell areas, and the NET area percentages were analyzed as NETotic cell areas divided by total DNA areas. The percentages of NETotic cells were analyzed as previously described (Valk et al., "Prognostically useful gene-expression profiles in acute myeloid leukemia," *N. Engl. J. Med.* 350:1617-1628 (2004)). Cells were incubated and simultaneously stained with both cell-permeable SYTO Red (1 μM) and cell-impermeable SY-TOX Green (1 μM) for 3 h. Then, the supernatant was discarded and the cells were fixed by 4% PFA at 4° C. Images were taken by the confocal microscopy Cell Observer (ZEISS, Germany). The percentage of NETotic cells was counted as the numbers of NETotic cells divided by the total cell numbers.

Detection of Circulating NETs

To analyze circulating NETs, MPO-DNA complexes in human sera or NE-DNA complexes in murine sera were assayed using previously described capture ELISA methods (Kessenbrock et al., "Netting neutro-phils in autoimmune small-vessel vasculitis," *Nat. Med* 15:623-625 (2009); Teijeira et al., "CXCR1 and CXCR2 chemokine receptor agonists produced by tumors induce neutrophil extracellular traps that interfere with immune cytotoxicity," *Immunity* 52:856-871 e858 (2020)) with slight modifications. To analyze human serological MPO-DNA, 96-well MaxiSorp ELISA Plates (44-2404, ThermoFisher) were coated with 5 μg/ml anti-MPO (0400-0002, Bio-Rad) capture antibody overnight at 4° C. After three washes in PBS, the wells were blocked with 5% BSA in PBS for 45 min at room temperature. Then, 50 μl of patient sera together with peroxidase-labeled anti-DNA monoclonal antibody (component No. 2 of the Cell Death Detection ELISA Kit, Roche, 11774425001) were added and incubated for 2 hat room temperature, and the plates were washed three times with washing buffer (1% BSA, 0.05% Tween-20 in PBS). To analyze mouse serological NETs, NE-DNA complexes were captured using a mouse NE ELISA kit (ab252356, ABCAM) in combination with the above-mentioned peroxidase-labeled anti-DNA monoclonal antibody according to the manufacturer's instructions. After three times of PBS washing, the peroxidase substrate (Roche, 11774425001) was added. After incubation at 37° C. for 1 h, the signals were measured at 405 nm.

Two-Chamber Neutrophil Migration Assays

The procedure of two-chamber migration assays was previously described (Zhuang et al., "Differential effects on lung and bone metastasis of breast cancer by Wnt signalling inhibitor DKK1," *Nat. Cell Biol.* 19:1274-1285 (2017)). Briefly, $5\times10^5$ freshly isolated neutrophils in RPMI 1640 were added to the upper chamber (363096, BD), and a 1:1 mixture of RPMI 1640 and cancer cell CM, or medium from neutrophils cultured in cancer cell CM, was added to the lower chamber as the chemoattractant. The migrated cells in the lower chamber were counted after 3 h.

Isolation of Neutrophil Plasma Membrane Proteins

Plasma membrane proteins of HL-60-derived neutrophils was purified following a previously reported protocol (Suski et al., "Isolation of plasma membrane-associated membranes from rat liver," *Nat. Protoc.* 9:312-322 (2014); Zhang et aL, "Neutrophil membrane-coated nanoparticles inhibit synovial inflammation and alleviate joint damage in inflammatory arthritis," *Nat. Nanotechnol* 13:1182-1190 (2018)). Neutrophils induced from HL-60 cells were cultured in differentiating medium (IMDM, 10% FBS, 1.25% DMSO) for 8 days. To harvest membrane proteins, frozen cells were thawed and suspended in hypotonic lysing buffer (225 mM D-mannitol, 30 mM pH 7.5 Tris-HCl, 0.2 mM EGTA, 75 mM sucrose) containing proteases inhibitor cocktail (539134, Merck) or cysteine protease inhibitor E64d (HY-100229, MCE) at a density of $1\times10^8$ cells/ml. Cells were homogenized in an ice-cold Dounce homogenizer (20 passes), and then centrifuged at 20,000 g for 20 min at 4° C., after which the pellet was discarded and the supernatant was centrifuged again at 100,000 g for 30 min at 4° C. The supernatant was cytosol fraction. The pellet containing the plasma membrane proteins was washed once in hypotonic lysing buffer. Plasma membrane proteins were isolated from human peripheral blood-derived neutrophils with the Pierce Cell Surface Protein Isolation Kit (Thermo Scientific, 89881) as previously described (Tei-jeira et al. "CXCR1 and CXCR2 chemokine receptor agonists produced by tumors induce neutrophil extracellular traps that interfere with immune cytotoxicity," *Immunity* 52: 856-871 e858 (2020)). Briefly, the cells were labeled with Thermo Scientific EZ-Link Sulfo-NHS—SS-Biotin, which is a non-cell-permeable and thiol-cleavable amine-reactive biotinylation reagent. Then, the whole cell lysate was obtained by lysing with Pierce IP Lysis Buffer (25 mM Tris-HCl pH 7.4, 150 mM NaCl, 1 mM EDTA, 1% NP-40 and 5% glycerol) and sonicating on ice using five 1-second bursts. The biotinylated cell membrane proteins were purified by NeutrAvidin-agarose resin and released by incubation with Pierce IP Lysis Buffer containing 5 mM dithiothreitol.

Enzymatic Activity Assays

The procedure of enzyme activity assays were conducted as previously reported (Korkmaz et aL, "Neutrophil proteinase 3 and dipeptidyl peptidase I (cathepsin C) as pharmacological targets in granulomatosis with polyangiitis (Wegener granulomatosis)," *Semin. Immunopathol.* 35:411-421 (2008)). The PR3 or NE enzymatic activity was quantified by detecting the rate of hydrolysis of the PR3-specific substrate (Abz)-VADnorVADRQ-(EDDnp) or NE specific substrate (Abz)-APEEIMRRQ-(EDDnp) by cell suspension or free enzymes. To analyze membrane-bound PR3 activity, neutrophils were cultured in cancer cell CM or non-conditioned medium, and treated with DMSO or various inhibitors, including Sivelestat (10 μM), Alvelestat (10 μM) and CTSGi (20 μM) for 30-45 min at 37° C. Then, cells were suspended in activity buffer ($5\times10^6$ per ml, PBS, 4 mM EGTA, pH 7.4) with 15 μM of the PR3-specific substrate, and the kinetic of hydrolysis was followed by measuring the fluorescence at $\lambda_{ex}$=320 nm and $\lambda_{em}$=420 nm. For activation of PR3 in isolated plasma membrane fraction, recombinant human CTSC (1071-CY, R&D) was activated according to the manufacturer's instruction. Then, plasma membrane proteins were diluted to 250 μg per ml and incubated with active human CTSC in activation buffer (25 mM MES, 50 mM NaCl, 5 mM DTT, pH 6.0) for 1 h. The activity of free PR3 and NE were measured in the assay buffer (50 mM Tris, 750 mM NaCl, pH 7.4) with 15 μM specific substrates by recording the fluorescence at $\lambda_{ex}$=320 nm and $\lambda_{em}$=420 nm.

Cytokine Antibody Array

Cytokines were detected in media of neutrophils cultured with CM from 4T07 cells by using the Mouse Cytokine Antibody Array (ab133994, ABCAM) according to the manufacturer's instruction. Briefly, membranes were blocked with the blocking buffer for 45 min, then incubated with 1 ml of samples containing protease inhibitor cocktail (539134, Merck) overnight at 4° C. After biotin-conjugated antibody and HRP-streptavidin incubation, chemiluminescence detection was performed. The cytokines included in the array are listed in Table S5 of Xiao et al., "Cathepsin C promotes breast cancer lung metastasis by modulating neutrophil infiltration and neutrophil extracellular trap formation," *Cancer Cell* 29:1-15 (2021).

ELISA

ELISA kits were used to assay the levels of human IL-1β (88-7621-88, ThermoFisher), mouse IL-1β (432604, Biolegend), mouse IL6 (88-7064-88, ThermoFisher), mouse CCL3 (88-56013-88, ThermoFisher) in cell culture supernatants or sera according to the manufacturer's instruction. Briefly, 96-well MaxiSorp™ ELISA Plates (44-2404, ThermoFisher) was coated with capture antibody overnight at 4° C. in coating buffer (15 mM of $Na_2CO_3$, 35 mM of $NaHCO_3$, at pH 9.6). After three washes in PBS, the wells were blocked with 5% BSA in PBS for 45 min at room temperature. Then, 100 μl of cell culture supernatants or sera and standard samples were added into the wells and incubated for 2 h at room temperature, and the plates were washed three times with washing buffer (1% BSA, 0.05% Tween-20 in PBS). Next, biotin-conjugated detection antibody in 2.5% BSA was added into the wells and incubated for 2 h at room temperature. After three washes with washing buffer, HRP-streptavidin was incubated for 45 min at room temperature. Then, signals were detected using TMB solution and read at 450 nm.

Immunofluorescence (IF) Staining

For murine lung tissues, the lungs were perfused with 50 ml of PBS through the right ventricle until they were cleared of blood. Then, the tissues were rinsed with pre-chilled PBS and fixed in 4% PFA for 2 h at 4° C. on a shaker, dehydrated by 30% sucrose in PBS overnight, embedded in OCT (Sakura, 4583) for 1 hat 4° C., followed by freezing at −80° C. Tissues were sectioned to 10 μm thickness, and were washed twice with PBS, permeabilized in 0.2% Triton X-100 for 15 min, blocked in PBS containing 5% BSA for 45 min. For EdU staining, CLICK PLUS EdU 647 Imaging Kit (ThermoFisher, C10640) was used.

Three-Dimensional Spheroid Culture

The procedure of 3D spheroids culture assay was previously reported (Taylor et al., "Lysyl oxidase contributes to mechanotransduction-mediated regulation of transforming growth factor-beta signaling in breast cancer cells," *Neoplasia* 13:406-418 (2011)). Briefly, 4T07 cells (200 per well) were cultured in 48-well plates on 100% growth-factor-reduced Matrigel (356231, BD) cushions in spheroid medium (a 1:1 mixture of 1% FBS DMEM and medium from neutrophils cultured in the cancer cell CM, 50% Matrigel supplemented with 50 μg/ml mTSP-1 (7859-TH-050). Upon completed gelation, 250 μl of culture medium (a 1:1 mixture of 1% FBS DMEM and medium from neutrophils cultured in the cancer cell CM) with 10 μg/ml mTSP-1 (7859-TH-050) was added to each well and the culture medium was changed every three days. On day 7-10, the numbers of the spheroids were analyzed.

Reactive Oxygen Species (ROS) Analysis

To measure the ROS levels, neutrophils were cultured in cancer cell CM or non-conditioned medium, and treated with DMSO or various inhibitors, including Sivelestat (10 μM), BAY11-7082 (10 μM) and SB203580 (10 μM) for 1 h at 37° C. Cells were then harvested and resuspended in assay buffer (PBS, 4 mM EGTA, pH 7.4, containing 10 μM CM-H2DCFDA, Invitrogen), incubated for 15 min at 37° C. in dark, washed with pre-chilled PBS, followed by FACS analysis within 30 min.

Clinical Analysis

All the formalin-fixed human breast cancer tissues were embedded in paraffin, and the samples were sectioned to 6 μm thickness. Paraffin-embedded sections were deparaffinized and rehydrated. Antigen retrieval was performed by citrate solution (pH 6.0) or Tris-EDTA (pH 9.0) at 95° C. Then, the sections were washed twice with PBS, permeabilized in 0.2% Triton X-100 for 15 min, blocked in PBS containing 5% BSA for 45 min. Next, the IF staining was performed as described above. The relative staining intensities of CTSC, Ci-H3 and MPO were calculated by normalization to DAPI staining intensities. IF levels were scored as negative, low, medium, or high for each sample. Samples were classified to CTSC-high or low expression groups with the median staining intensity of all the stained primary tumors as the cut-off for Kaplan-Meier survival analysis. Serum samples were analyzed with the CTSC ELISA kit (ELH-Cathepsin C, RayBiotech) after blood pretreatment according to the manufacturer's instructions.

Statistical Analysis

Data analyses were performed using GraphPad Prism 7.0 (GraphPad Software, La Jolla, USA). The data presentation and statistical analyses are described in the figure legends. p values <0.05 were considered as statistically significant. The experiments in vitro were repeated independently multiple times with similar results, as indicated in the figure legends.

Example 1: CTSC Expression in Breast Cancer Cells with High Potential of Lung Metastasis 74 primary lesions and 29 lung metastatic lesions are obtained from breast cancer patients. These include paired primary tumors and lung metastases from seven breast cancer patients. CTSC protein expression levels of the samples are analyzed by immunofluorescence staining, as shown in FIGS. 1A-C.

To verify that CTSC is clinically associated with lung metastasis in breast cancer, the level of CTSC in the serum of patients with breast cancer is measured with an enzyme-linked immunosorbent assay (ELISA). The patients are then divided into two groups according to the expression level of CTSC protein in tumor samples, the first group corresponding to high CTSC expression and the second group corresponding to low CTSC expression. Finally, the prognoses (metastasis-free and total survival) of the two groups of patients are compared using Kaplan-Meier survival analysis.

Figure 1B:
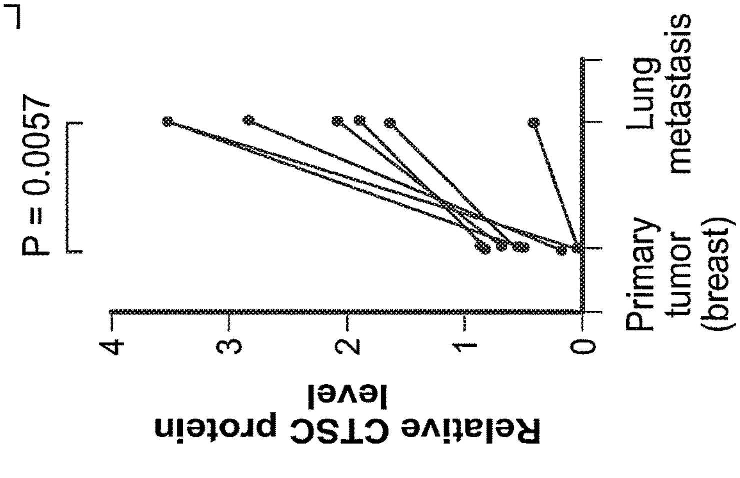
Figure 1C:
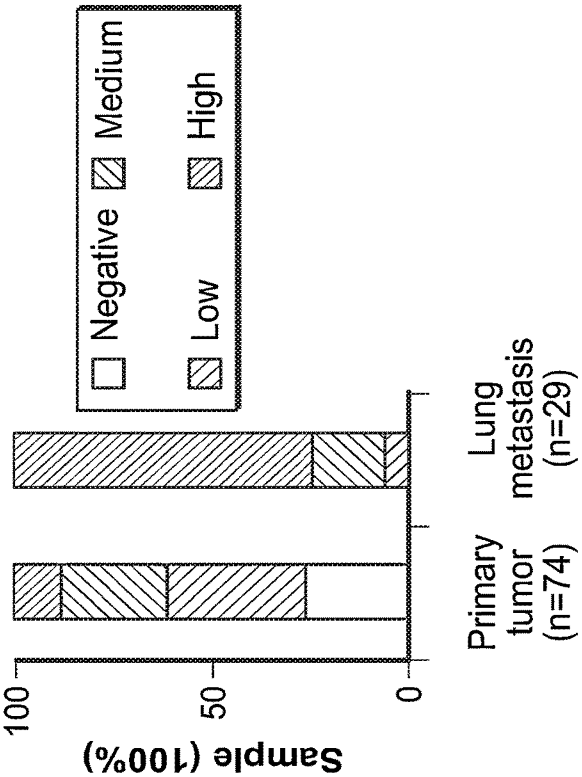
FIG. 1C compares CTSC protein expression levels in 103 tumor samples consisting of primary tumors (74 cases) and lung metastasis lesions (29 cases) of breast cancer patients.

Analysis of CTSC protein expression levels by immunofluorescence (IF) staining shows that CTSC protein levels are significantly upregulated in lung metastases compared to primary tumors from breast cancer patients (FIG. 1A). From the immunofluorescence images of FIG. 1A, the relative CTSC protein levels in paired primary tumors and lung metastases are calculated by normalization to 4',6-diamidino-2-phenylindole (DAPI) stain (FIG. 1B). As shown in FIG. 1B, CTSC expression is elevated in lung metastases compared to paired primary tumors. Further, as shown in FIG. 1C, when all 103 tumor samples are considered together, there is low or no CTSC expression in more than half of the primary tumors, while, in general, CTSC is highly expressed in lung metastases.

Figure 1E:
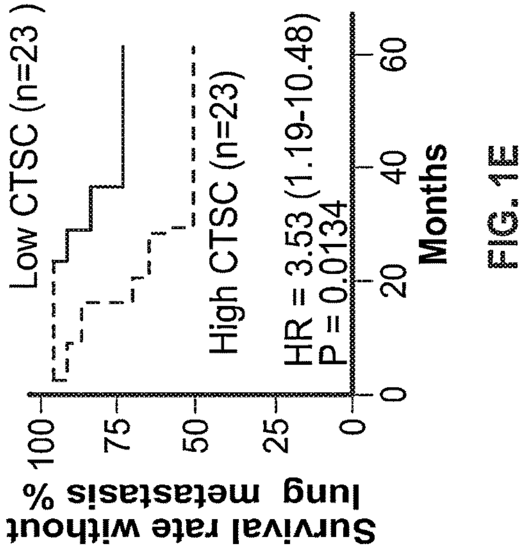
FIG. 1E compares the survival rates of breast cancer patients without lung metastasis having either low and high serum CTSC levels.
Figure 1F:
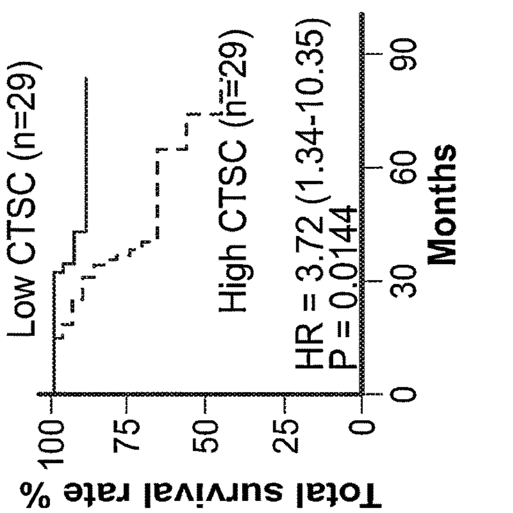
FIG. 1F shows a survival curve analysis of breast cancer patients when grouped by low and high CTSC tissue levels.
Figure 1D:
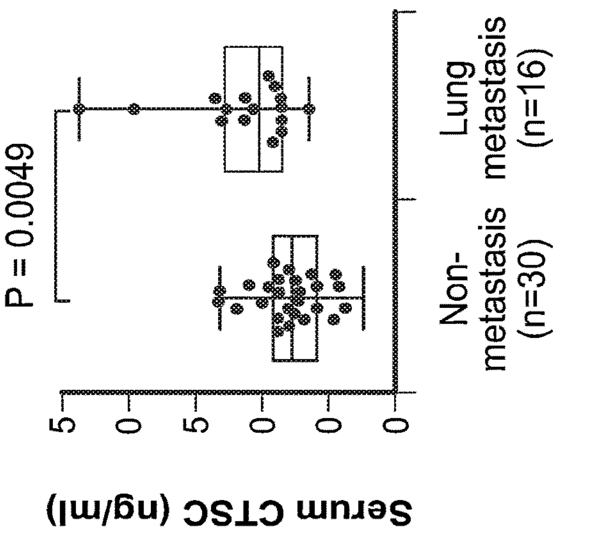
FIG. 1D compares serum CTSC levels of breast cancer patients with or without metastasis in the lungs.

Higher serological CTSC concentration correlates with recurrence of lung metastases in breast cancer patients (FIG. 1D). As shown in FIG. 1D, breast cancer patients who experience recurrence of lung metastasis have significantly higher CTSC levels in serum as compared to breast cancer patients without recurrence of metastasis. Such elevated serum CTSC levels are shown to correspond to shorter metastasis-free and overall patient survival times (FIGS. 1E-F). As shown in FIG. 1E, the lung metastasis-free survival period of patients with high CTSC expression level in serum is significantly shorter than patients with low CTSC serum expression according to Kaplan-Meier analysis. Further, as shown in FIG. IF, patients in the high CTSC expression group have significantly shorter overall survival periods than patients in the low CTSC expression group according to Kaplan-Meier analysis.

The data provided in FIGS. 1A-F demonstrates that CTSC secretion level has a significant positive correlation with the potential of lung metastasis in breast cancer patients, indicating that CTSC may be used as a marker gene to predict the risk of lung metastasis in breast cancer patients.

Example 2: Impacts of CTSC Overexpression on Lung Metastasis of Breast Cancer To verify that CTSC functionally promotes lung metastasis of breast cancer, CTSC is over-expressed in SCP28, a sub-line of MDA-MB-231, which displays median endogenous CTSC levels and a low potential for lung metastasis. To assay the consequence of CTSC overexpression on lung metastasis, luciferase-tagged SCP28 control cells or CTSC overexpressing luciferase-tagged SCP28 cells are introduced into mice via tail vein injection. In vivo imaging is performed to detect the extent of lung metastasis via quantitation of luciferase signal.

Luciferase-tagged SCP28 control cells (1) or luciferase-tagged SCP28 cells overexpressing CTSC (2) are introduced into mice via tail-vein injection. Luciferase signals of lung tissues of the two groups of mice (i.e., mice injected with control cells or mice injected with CTSC overexpressing cells) are assessed, the numbers of pulmonary surface metastatic nodules of the two groups are determined, and the overall survival rates of the two groups are calculated to determine the consequence of CTSC overexpression on lung metastasis. The results are shown in FIGS. 2A-D.

Figure 2B:
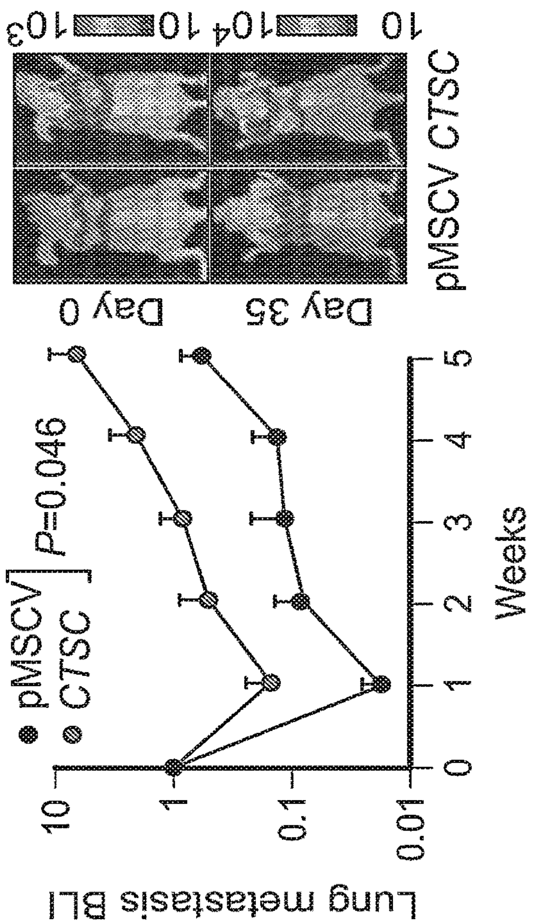
FIG. 2 demonstrates that CTSC overexpression promotes lung metastasis of breast cancer.
FIG. 2A shows mRNA and protein level verifications of CTSC overexpression in SCP28 cells by Western blot.
Figure 2A:
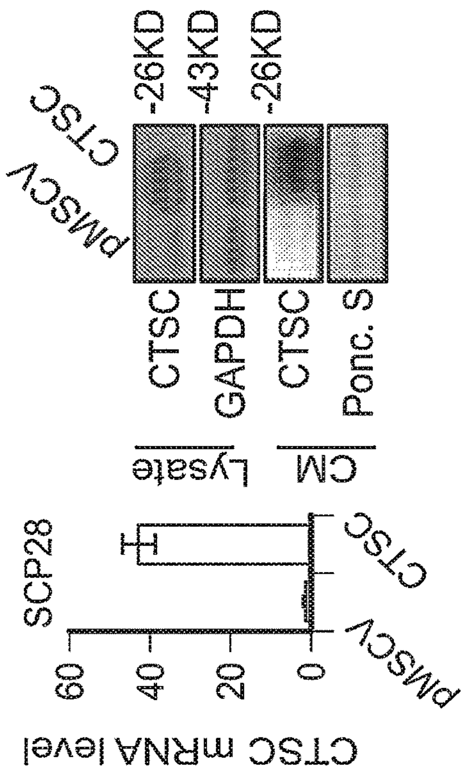

The left panel of FIG. 2A confirms that CTSC mRNA levels are higher in CTSC-overexpressed SCP28 cells as compared to control SCP28 cells ("pMSCV group"). The right panel of FIG. 2A depicts Western blot images showing that CTSC protein levels are indeed upregulated in the CTSC-overexpressed group as compared to the control group. "CM" is conditioned medium.

As shown graphically in the left panel of FIG. 2B, mice injected with SCP28 cells overexpressing CTSC exhibit significantly more lung metastases as compared to control mice, as indicated by higher overall levels of bioluminescence in the CTSC overexpression group throughout the five-week time period. As shown in the right panel of FIG. 2B, mice transplanted with SCP28 cells overexpressing CTSC exhibit significantly more lung metastases than mice injected with control SCP28 cells at 35 days post-injection.

Figure 2C:
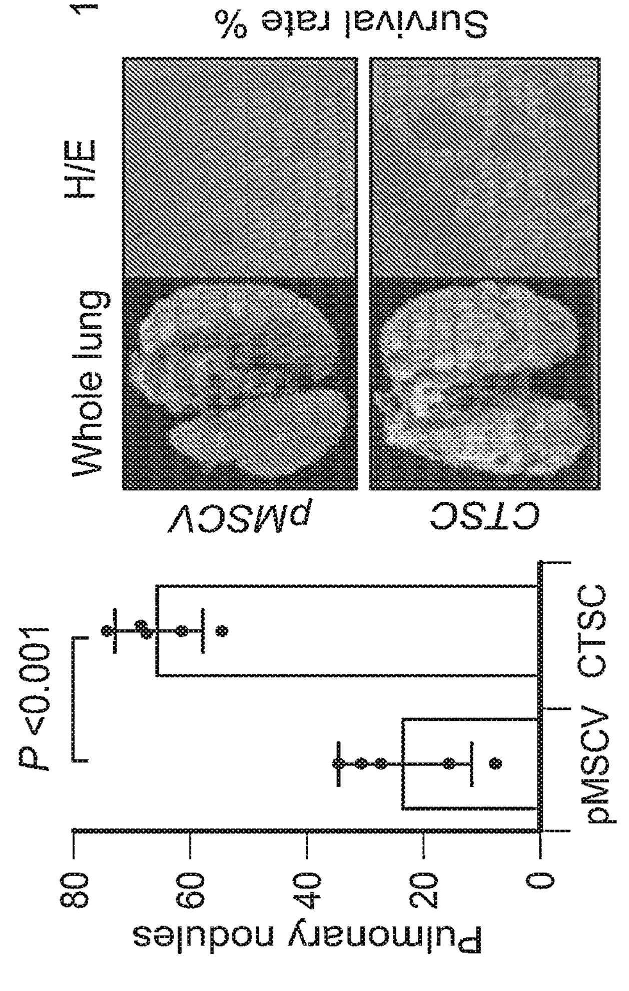

As shown graphically in the left panel of FIG. 2C, the lungs of mice transplanted with SCP28 cell overexpressing CTSC have a larger average number of pulmonary surface metastatic nodules as compared to mice injected with control SCP28 cells. The center panel of FIG. 2C shows whole lung images for a mouse injected with control SCP28 cells and a mouse injected with SCP28 cells overexpressing CTSC. It is observed that the whole lung of the mouse injected with SCP28 cells overexpressing CTSC contains a larger number of visible pulmonary surface metastatic nodules. The right panel of FIG. 2B compares HE-stained lung tissue from a mouse injected with control SCP28 cells and a mouse injected with SCP28 cells overexpressing CTSC. It is observed that the nodule density in the lung tissue of the mouse injected with SCP28 cells overexpressing CTSC is significantly higher than that of the mouse injected with SCP28 control cells.

Figure 2D:
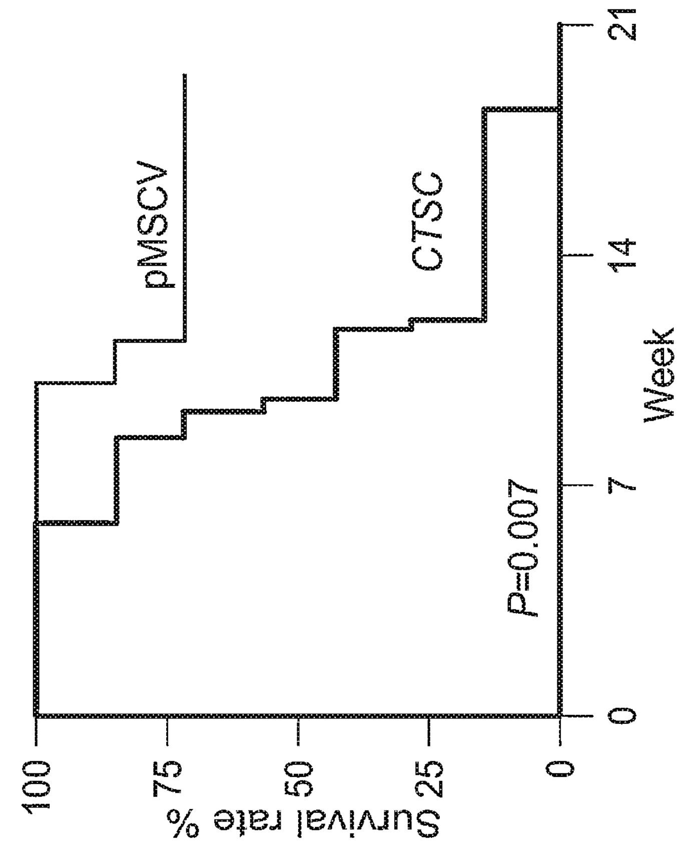

Survival rate is impacted by CTSC overexpression. Compared with the group injected with control SCP28 cells, the survival rate of mice injected with SCP28 cells overexpressing CTSC is significantly reduced (FIG. 2D).

The data provided in FIGS. 2A-D demonstrate that overexpression of CTSC can functionally promote lung metastasis of breast cancer cells as assayed by mouse tail-vein injection.

Example 3: Impacts of CTSC Knockdown on Lung Metastasis of Breast Cancer

To assess the functional impact of CTSC loss on lung metastasis of breast cancer cells, LM2-4175, a sub-line of MDA-MB-231 with a known high potential of lung metastasis is used. Lung metastasis following mouse tail vein injection of control luciferase-tagged LM2-4175 or luciferase-tagged LM2-4175 with reduced levels of CTSC (shCTSC#1 and shCTSC#2) is assessed as in Example 2. Fluorescence signals of lung tissues and the numbers of pulmonary surface metastatic nodules of mice injected with control luciferase-tagged LM2-4175 and mice injected with luciferase-tagged, CTSC reduced LM2-4175 and their respective survival rates are calculated. The results are shown in FIGS. 3A-D.

Figure 3A:
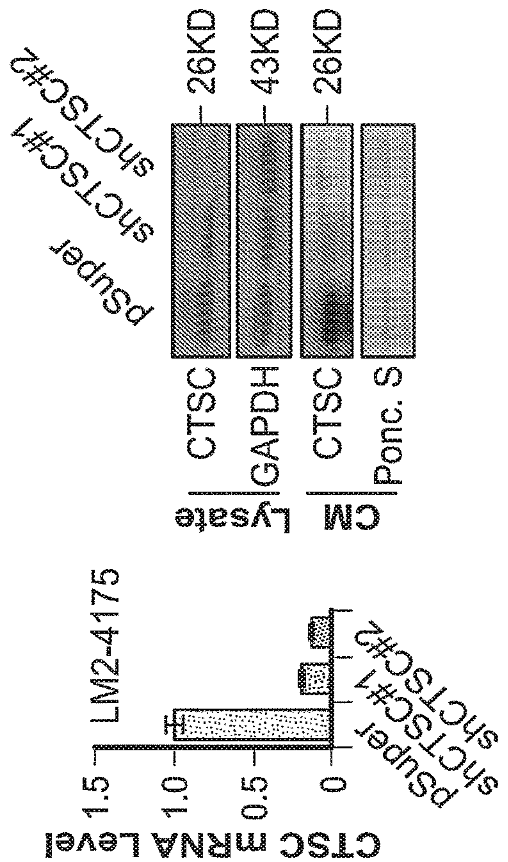
FIG. 3A shows mRNA and protein level verifications of CTSC knockdown in LM2-4175 cells by Western blot.
Figure 3B:
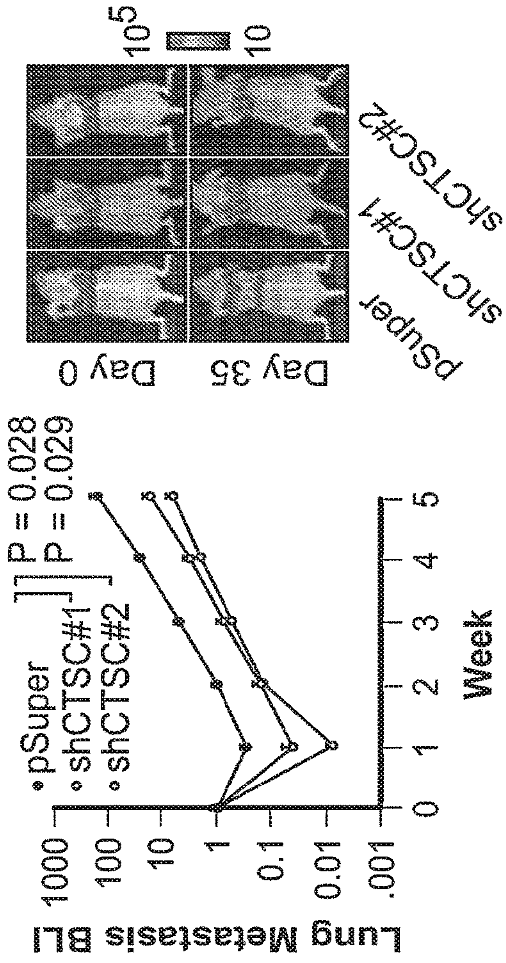
FIGS. 3B-D show fluorescence signals of the lungs after tail vein injection of CTSC reduced LM2-4175 cells in mice (B), the number of pulmonary surface metastatic nodules after tail vein injection of CTSC reduced LM2-4175 in mice (C), and a survival analysis of mice injected with CTSC reduced LM2-4175 compared to a control group of mice injected with LM2-4175 cells (n=10 for each group) (D).
Figure 3D:
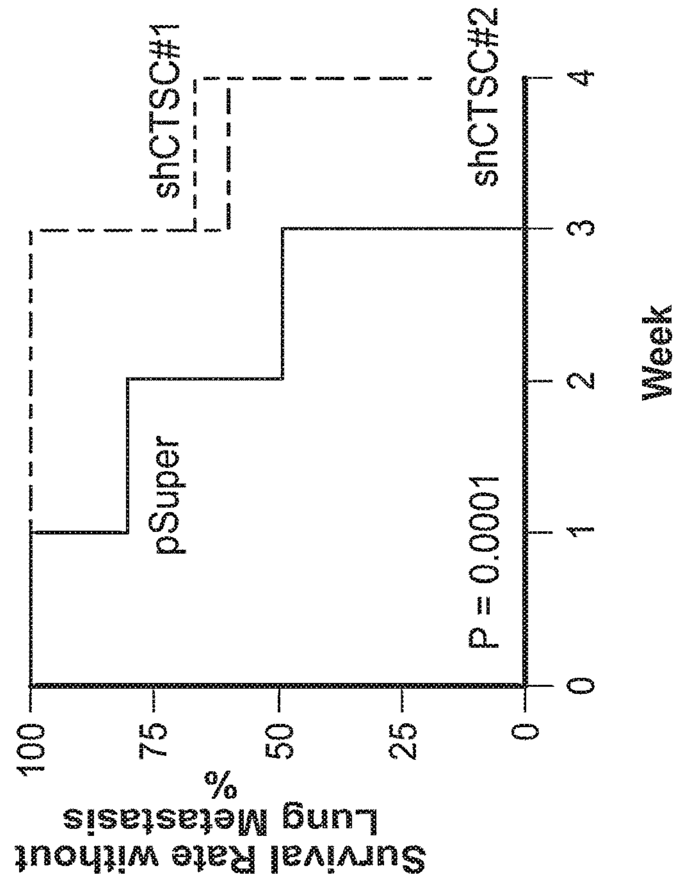
Figure 3C:
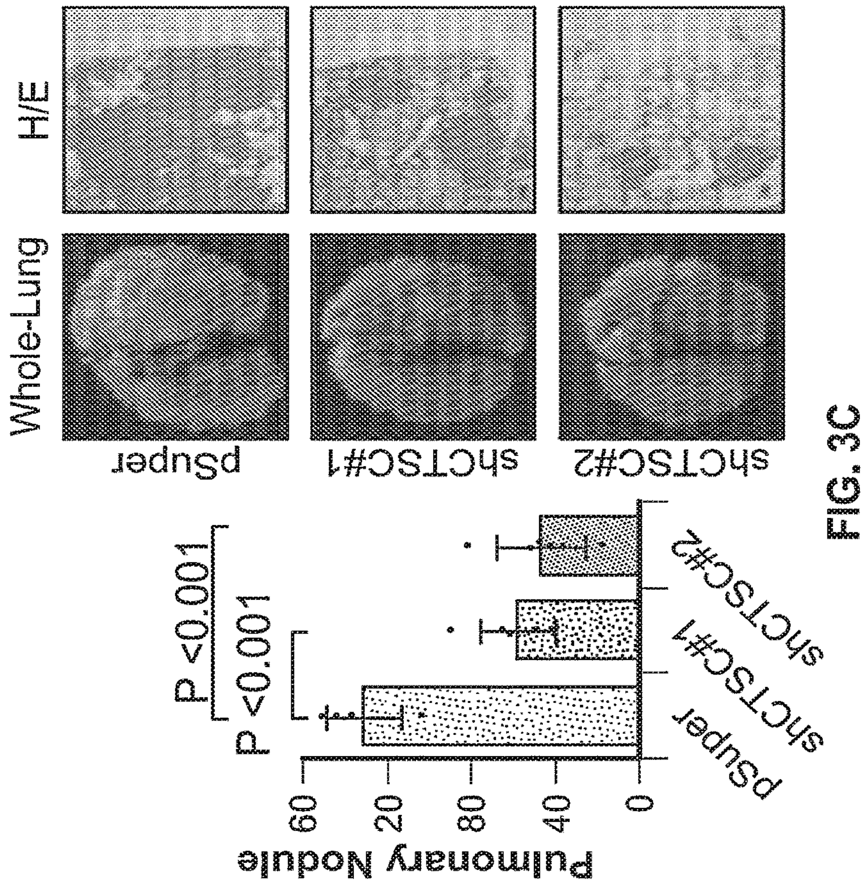

The left panel of FIG. 3A confirms that CTSC mRNA levels are lower in LM2-4175 cells bearing shRNA targeting CTSC ("shCTSC#1" and "shCTSC#2") as compared to control LM2-4175 cells ("pSuper" group). The right panel of FIG. 3A depicts Western blot images confirming the reduction of CTSC protein following shRNA knockdown of CTSC in LM2-4175 cells ("shCTSC#1" and "shCTSC#2") compared to control LM2-4175 cells ("pSuper" group). "CM" is conditioned medium.

Following tail-vein injection of mice with CTSC-reduced LM2-4175 cells, lung metastasis and pulmonary surface metastatic nodule formation are reduced (FIGS. 3B and 3C, respectively), and metastasis-free survival is increased (FIG. 3D) compared to mice injected with LM2-4175 control cells.

The data provided in FIGS. 3A-D demonstrate that CTSC knockdown can attenuate lung metastasis of breast cancer cells in extend survival as assayed by mouse tail-vein injection.

Example 4: Impacts of CTSC Expression on Lung Metastasis of Breast Cancer in Immune-Complete Mice In order to verify the Effects of CTSC expression on lung metastasis of breast cancer, the impact of the immune system of the mice on lung metastasis is examined. A BALB/c mouse model with an intact immune system is used, and two types of experiments are conducted.

In the first type of experiment, a 4T07 control cell line and a 4T07 mouse breast cancer cell line with overexpressed CTSC, both tagged with luciferase, are injected into the tail veins of immune-competent BALB/c mice to generate control and CTSC-overexpressed groups of mice. Then, fluorescence signals of lung tissues and the numbers of pulmonary surface metastatic nodules of the two groups of mice are obtained. The results are shown in FIGS. 4B-C.

In the second type of experiment, a 4T1 control cell line and a 4T1 cell line with reduced CTSC are injected into the mammary fat pads of immune-competent BALB/c mice to generate control and CTSC knockdown groups of mice. Then, tumor growth volumes and the numbers of pulmonary nodules of the two groups of mice are obtained. The results are shown in FIGS. 4D-E.

Figure 4A:
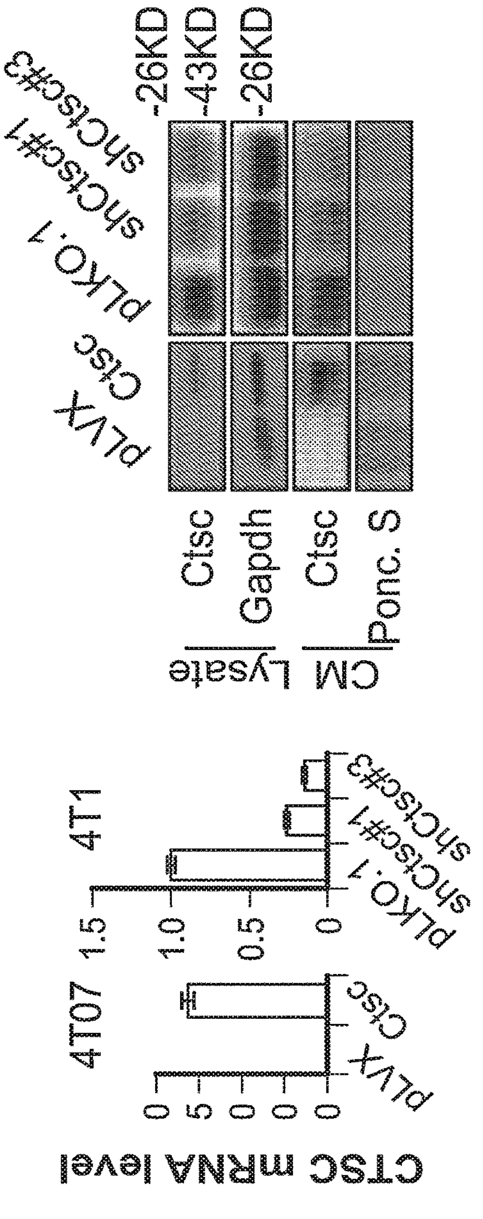
FIG. 4A shows mRNA and protein level verifications of CTSC overexpression in 4T07 cells and CTSC reduction in 4T1 cells by Western blot.

The left panel of FIG. 4A confirms that CTSC mRNA levels are higher in 4T07 cells compared to the control cell line. The center panel of FIG. 4A confirms that CTSC mRNA levels are lower in 4T1 cells with CTSC knocked down ("shCTSC#1" and "shCTSC#2") as compared to control cells ("pVLX" group). The right panel of FIG. 4A depicts Western blot images showing that CTSC protein levels are upregulated in the CTSC-overexpressed cells and downregulated in the two CTSC-knockdown groups, as compared to the corresponding control groups. "CM" is conditioned medium.

Figure 4B:
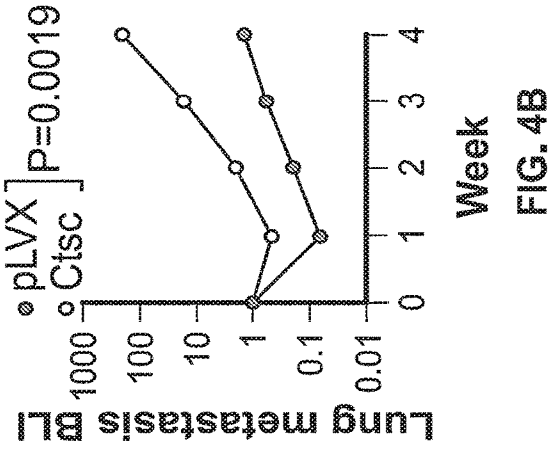
FIG. 4B shows fluorescence signals of the lungs after tail vein injection of CTSC overexpressing 4T07 cells in mice, or after mammary fat pad injection of CTSC reduced 4T1 cells.
Figure 4E:
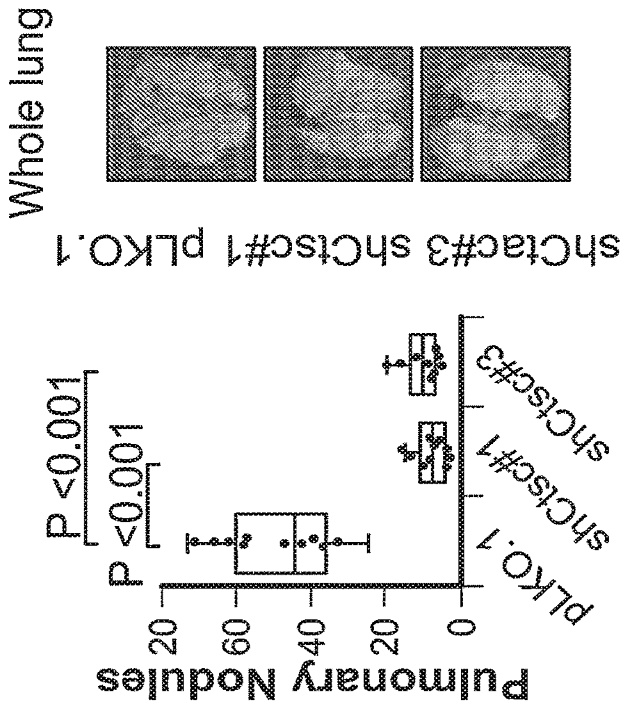
FIGS. 4D-E show changes in tumor volume (D) and the number of pulmonary metastatic nodules (E) for mice injected with CTSC reduced 4T1 cells versus mice injected with 4T1 control cells (n=10 for each group).
Figure 4D:
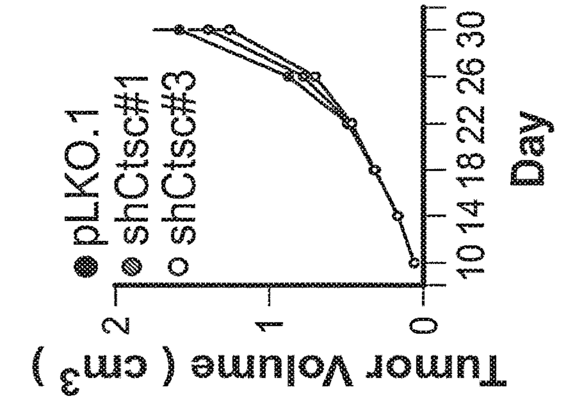
Figure 4C:
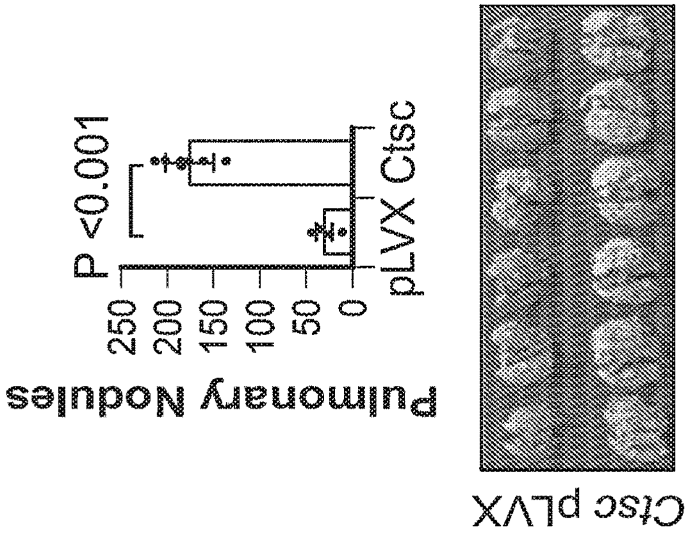
FIG. 4C shows the number of surface metastatic nodules for mice injected with CTSC overexpressing 4T07 cells versus control 4T07 cells (n=10 for each group).

FIG. 4B shows that following intravenous injection of immune-complete mice with 4T07 cells with overexpressed CTSC, tumor metastasis to the lung is upregulated, thereby indicating that CTSC overexpression significantly promotes the growth of the tumor cells in the lungs and that this effect is not affected by the intact, competent immune system of BALB/c mice.

FIG. 4C shows that following intravenous injection of immune-competent mice with 4T07 cells with overexpressed CTSC, the number of pulmonary nodules in the mice in the CTSC-overexpressed group is significantly higher than that of the blank control group. This indicates that CTSC overexpression significantly increases the number of pulmonary surface metastatic lesions in mice and that this promoting effect is not affected by the intact, competent immune system of BALB/c mice.

On the other hand, following orthotopic injection of 4T1 cells with CTSC knocked down in immune-competent mice, both tumor volumes and tumor growth rates are lower in the CTSC-knockdown group compared to the control group (FIG. 4D). Moreover, in immune-competent mice, CTSC reduction does not affect the in-situ growth of 4T1 cells at the site of transplant, but significantly decreases the formation of pulmonary surface metastatic nodules as compared to the control group (FIG. 4E).

In summary, the data provided in FIGS. 2A-4E establishes that CTSC promotes lung metastasis of breast cancer cells in mice that are immunodeficient and immune competent.

Example 5: CTSC Promotes Early-Stage Seeding and Sustained Proliferation of Breast Cancer Cells During Lung Metastasis CTSC plays a role in early stage metastatic colonization of breast cancer cells in the lungs. Bioluminescent imaging (BLI) of mice injected with SCP28 with overexpressed CTSC shows significant lung metastasis during the first week following injection (FIG. 5A). Meanwhile, lung metastasis declines or remains steady in mice injected with control cells, not overexpressing CTSC (pMSCV), throughout the first week following injection, as evidenced by decreases in BLI signal.

Figure 5B:
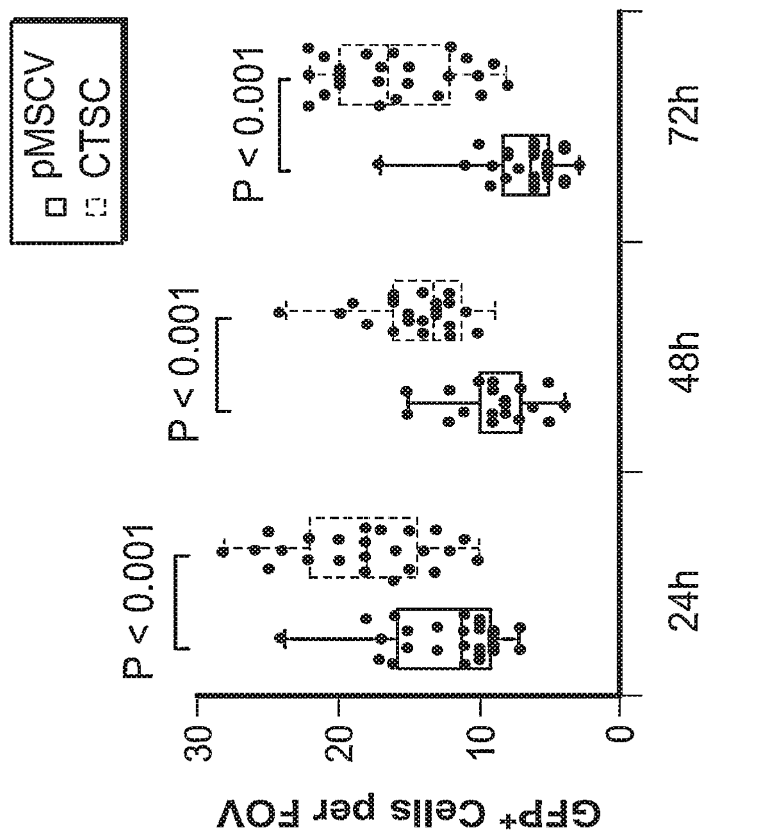
FIG. 5B shows increased seeding of cancer cells in mice injected with CTSC overexpressing SCP28 cells over time, as detected by immunofluorescent staining of lung sections.
Figure 5A:
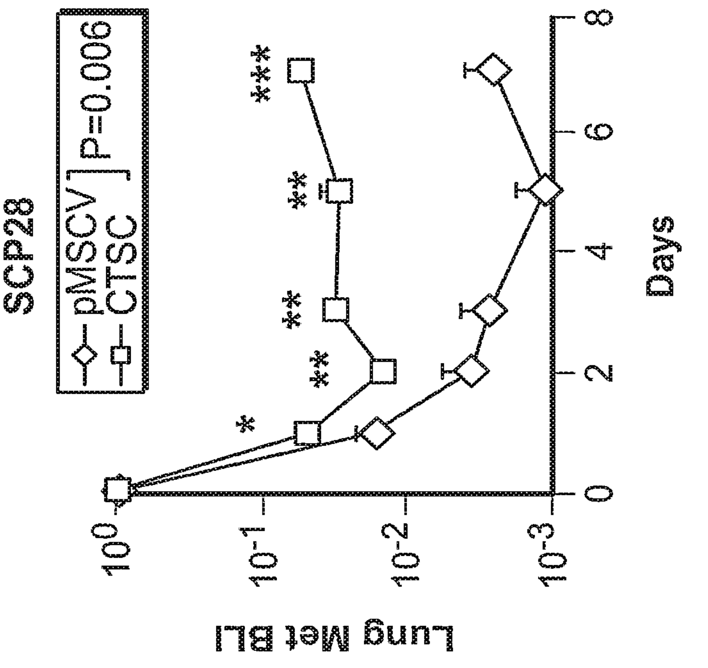
FIG. 5A shows the results of bioluminescent imaging (BLI) of lung metastases in mice injected with CTSC overexpressing SCP28 cells as compared to SCP28 control cells, showing increased lung metathesis in CTSC overexpressed mice.

As shown in FIG. 5B, immunofluorescent staining of lung sections of mice treated with SCP28 cells with CTSC overexpressed reveals increased seeding of cancer cells overexpressing CTSC in the lung parenchyma at 24 h, 48 h, and 72 h post-injection. The proliferation of cancer cells seeded in the lungs of mice transplanted with CTSC overexpressing SCP28 cells is assessed by 5-ethynyl-2'-deoxyuridine (EdU) labeling at 24 h prior to lung harvest. As shown in FIG. 5C, CTSC-overexpressed cells are more proliferative than control cells, following lung seeding at 24 h, 48 h, and 72 h timepoints post-injection.

Reduction of CTSC is shown to have opposite effects on early stage metastatic colonization of breast cancer cells in the lungs. BLI of mice injected with LM2 cells with CTSC knocked down shows significantly decreased lung metastasis throughout the first week post-injection as compared to mice injected with control cells (FIG. 5D).

Figure 5E:
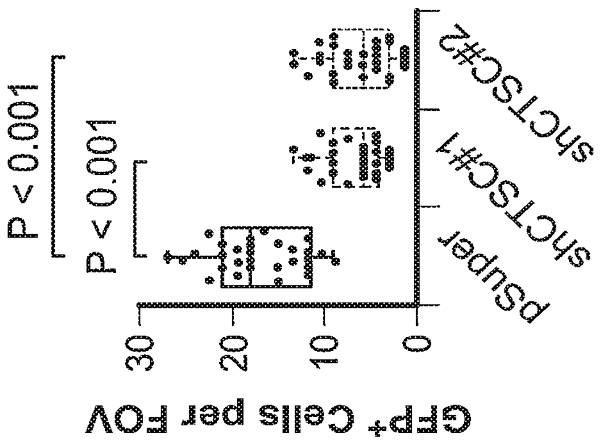
FIGS. 5E-F show reductions in cancer cell seeding (E) and proliferation (F) for CTSC reduced cells in mice.
Figure 5D:
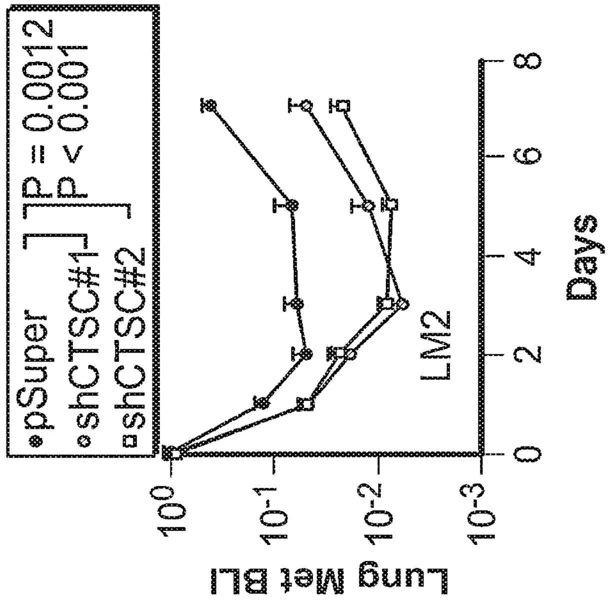
Figure 5C:
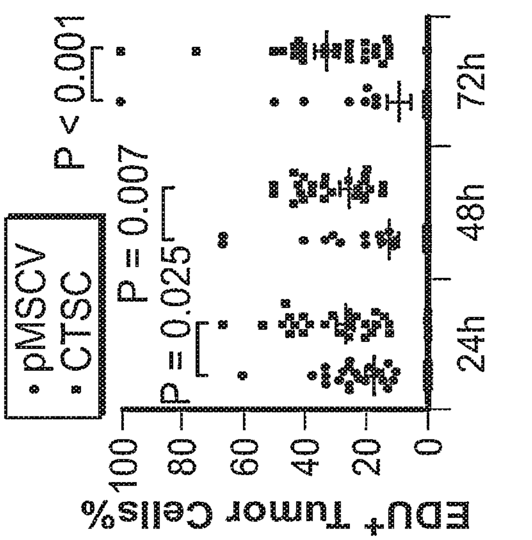
FIG. 5C shows that CTSC overexpressed cells in mice are more proliferative than control cells in mice. On the other hand.

As shown in FIG. 5E, immunofluorescent staining of lung sections of mice treated with LM2 with CTSC knocked down reveals decreased seeding of $GFP^+$ cancer cells in the lung parenchyma at 72 h post-injection. As shown in the right panel of FIG. 5F, Edu-labeling indicates that fewer seeded CTSC-overexpressed cells have proliferated as compared to control cells at 72 h after injection.

Figure 5G:
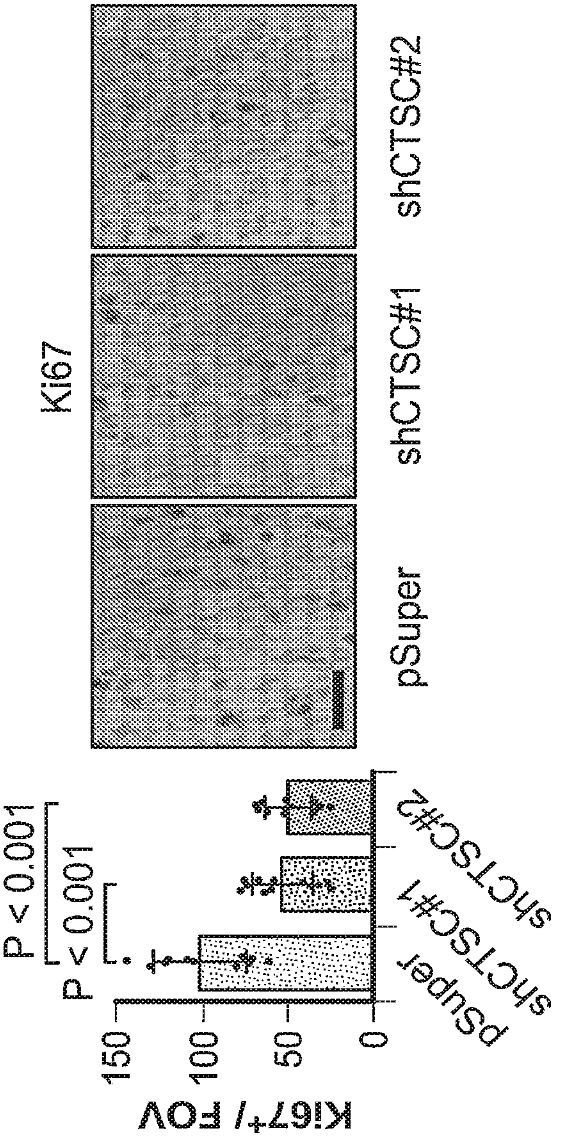
FIG. 5G visually compares the lung metastases in mice by Ki67 staining at six weeks following injection with LM2 cells with CTSC knocked down.
Figure 5F:
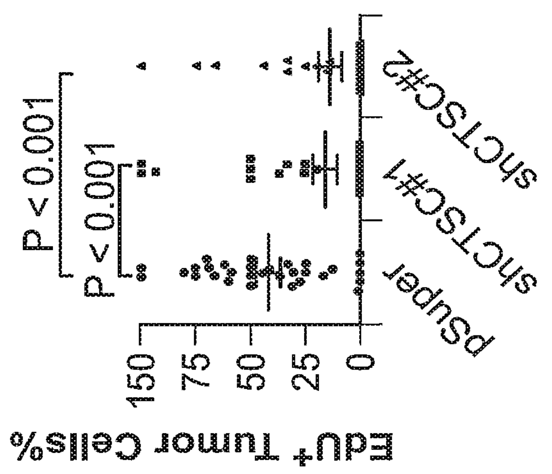

CTSC reduction is also shown to inhibit the metastatic growth of cancer cells in later stage metastasis. As shown in FIG. 5G, Ki67 staining of the lungs of mice injected with CTSC-knockdown cells six weeks after injection reveals decreased lung metastases as compared to the lungs of mice injected with control cells.

The data provided in FIGS. 5A-G demonstrate that CTSC expression levels impact the proliferation of tumor cells during the seeding stage of metastasis.

Example 6: CTSC Promotes Recruitment of Neutrophils in Lung Metastasis

Figure 6A:
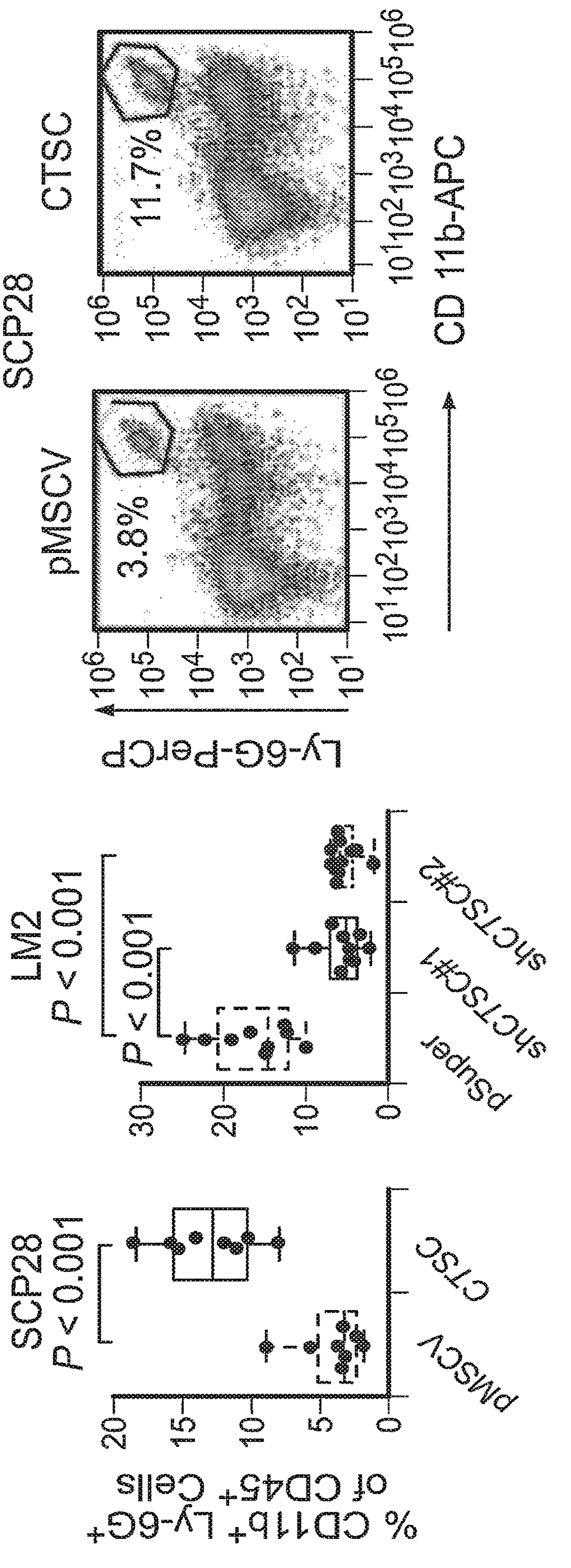
FIG. 6A provides flow cytometry results quantifying, as a percentage, the amounts of $CD11b^+Ly6G^+$ neutrophils in $CD45^+$ immunocytes of lung metastases in mice injected with SCP28 cells with overexpressed CTSC, and mice injected with LM2 cells with reduced CTSC.

CTSC plays a role in regulating neutrophil recruitment in lung metastasis. Percentages of $CD11b^+Ly6G^+$ neutrophils in $CD45^+$ immunocytes of lung metastases in treated mice are determined by flow cytometry at 7 weeks post-injection. As shown in the left panel of FIG. 6A, SCP28 cells with overexpressed CTSC contain larger percentages of $CD11b^+Ly6G^+$ neutrophils as compared to control cells. Conversely, as shown in the center panel of FIG. 6A, LM2 cells with reduced CTSC contain smaller percentages $CD11b^+Ly6G^+$ neutrophils relative to control cells. The rightmost panel of FIG. 6A presents flow cytometry analysis indicating that CTSC overexpressing cells have a higher percentage (11.7%) of neutrophils compared to control cells (3.8%), circled in both graphs.

The percentages of $CD11b^+Ly6G^+$ neutrophils in $CD45^+$ immunocytes in the lung parenchyma in treated mice are also determined by flow cytometry at 72 h after injection. As shown in the left panel of FIG. 6B, SCP28 cells with overexpressed CTSC contain larger percentages of $CD11b^+Ly6G^+$ neutrophils than control cells. As shown in the right panel of FIG. 6B, LM2 cells with reduced CTSC contain smaller percentages of $CD11b^+Ly6G^+$ neutrophils relative to control cells.

Figure 6C:
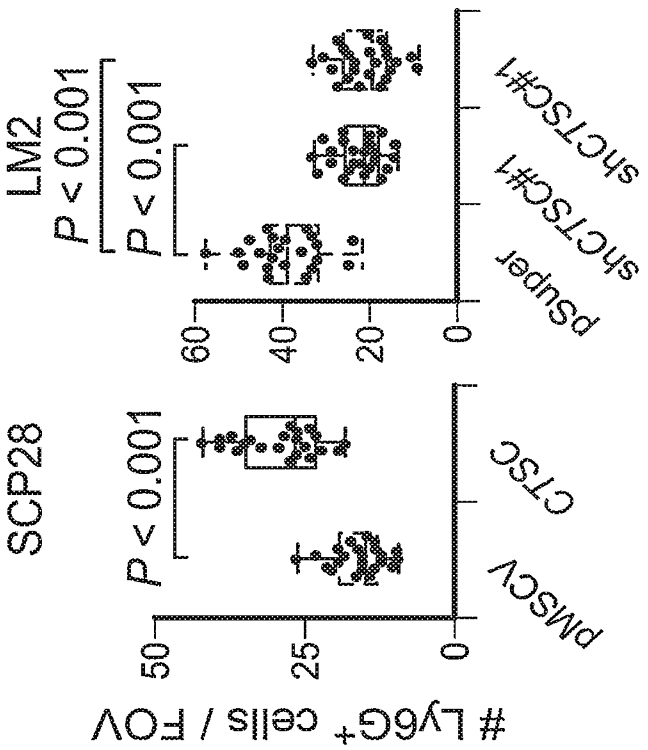
FIG. 6C shows increased clustering of $CD11b^+Ly6G^+$ neutrophils in proximity to cancer cells in mice injected with CTSC-overexpressed SCP28 cells, and decreased clustering in mice injected with LM2 cells with reduced CTSC.
Figure 6B:
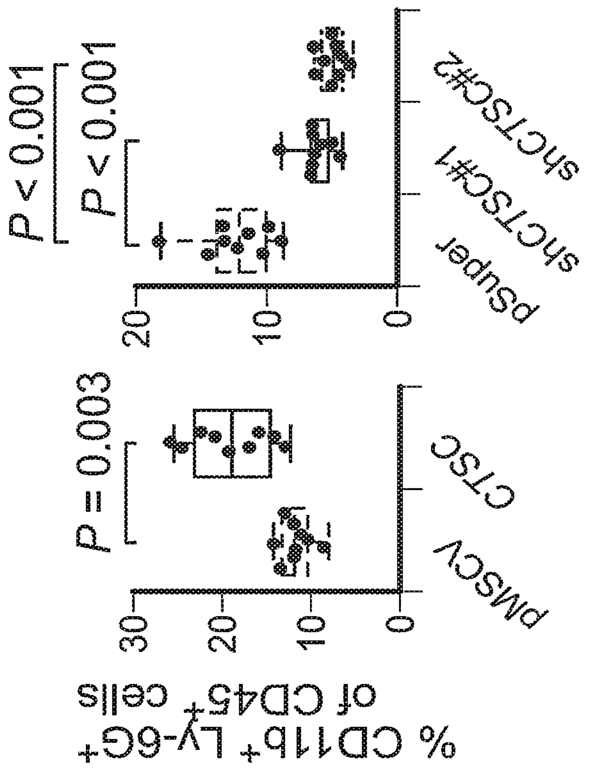
FIG. 6B provides comparable flow cytometry results for $CD11b^+Ly6G^+$ neutrophils in $CD45^+$ immunocytes in the lung parenchyma of similarly-treated groups of mice.

Immunostaining of mouse lung tissue shows that $CD11b^+Ly6G^+$ neutrophils cluster in closer proximity to cancer cells in mice injected with CTSC-overexpressed SCP28 cells (FIG. 6C, left panel) compared to control pMSCV cells. Less aggregation of $CD11b^+Ly6G^+$ neutrophils with cancer cells is observed in mice injected with LM2 cells with reduced CTSC compared with control cells (FIG. 6C).

Figure 6D:
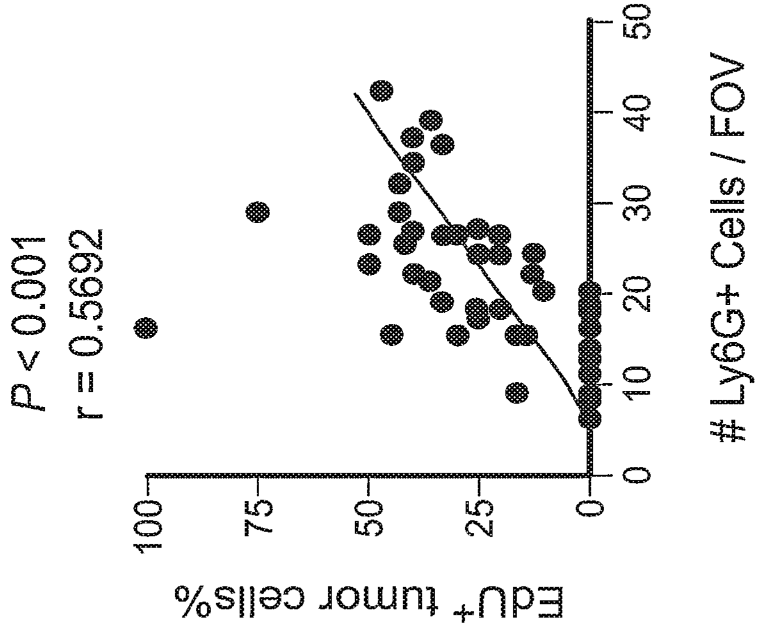
FIG. 6D correlates $CD11b^+Ly6G^+$ neutrophil aggregation to $EdU^+$-labeled seeded tumor cell proliferation.

A correlation between the proliferation of $EdU^+$-labeled seeded tumor cells and aggregation of $CD11b^+Ly6G^+$ neutrophils around them is shown in FIG. 6D.

Figure 6E:
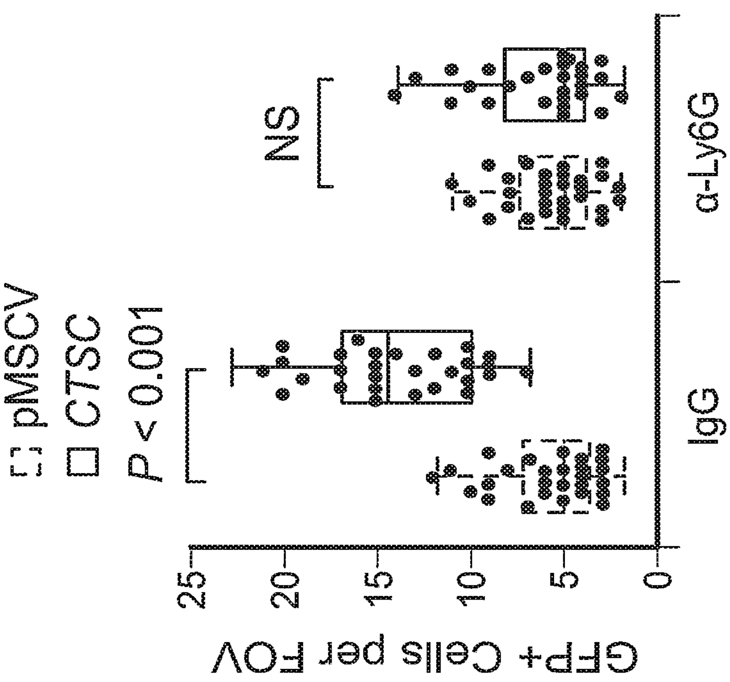
FIGS. 6E-G show that treatment of mice with an Ly6G clearance antibody prior to injection of SCP28 cells with overexpressed CTSC results in reduced neutrophil aggregation (E), proliferation (F), and lung nodule formation (G).
Figure 6G:
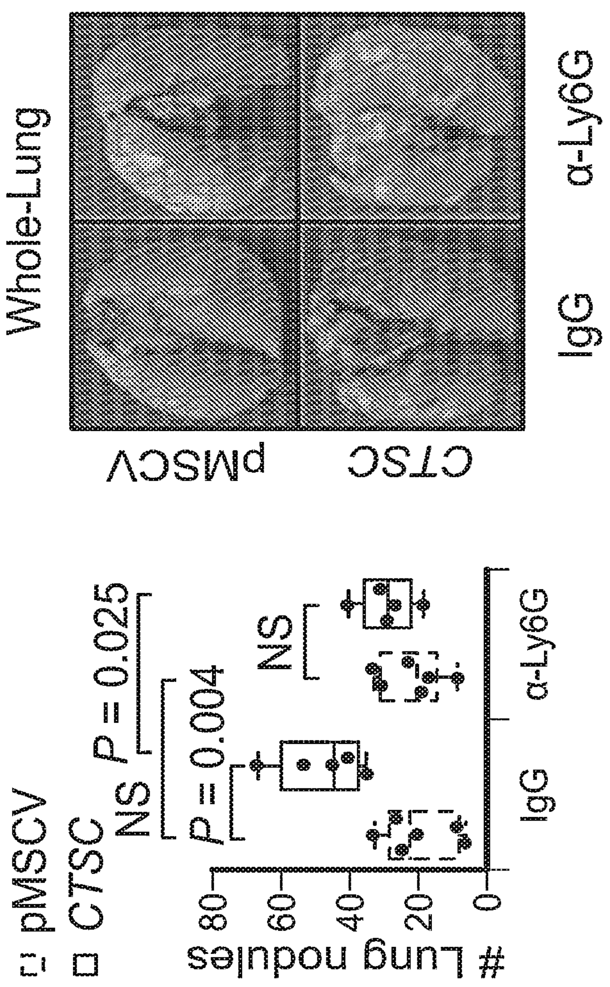
Figure 6F:
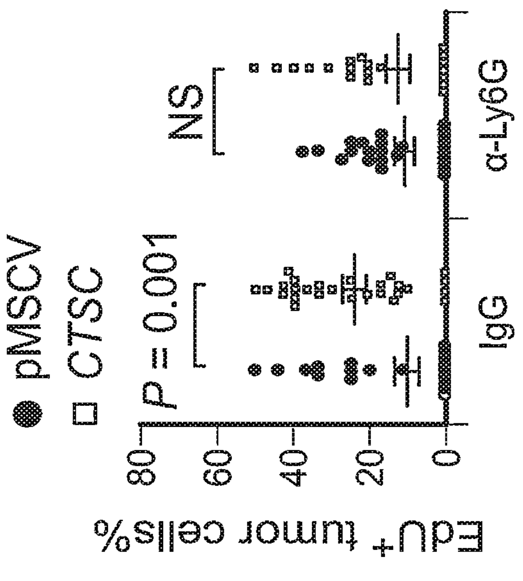

The early stage seeding and proliferation of cancer cells is lost when the neutrophils in subject mice are depleted by treatment with an Ly6G clearance antibody prior to injection of SCP28 cancer cells, as compared to pre-treatment with IgG (FIG. 6E). The same is true for the early stage seeding and proliferation of $EdU^+$-labeled tumor cells (FIG. 6F). In addition, the formation of pulmonary surface metastatic nodules at 8 weeks post-injection is suppressed in SCP28 mice pre-treated with α-Ly6G relative to SCP28 mice pre-treated with IgG (FIG. 6G).

The data provided in FIGS. 6A-G demonstrate that CTSC overexpression in lung metastases promotes increased neutrophil recruitment.

Figures 7A, 7B:
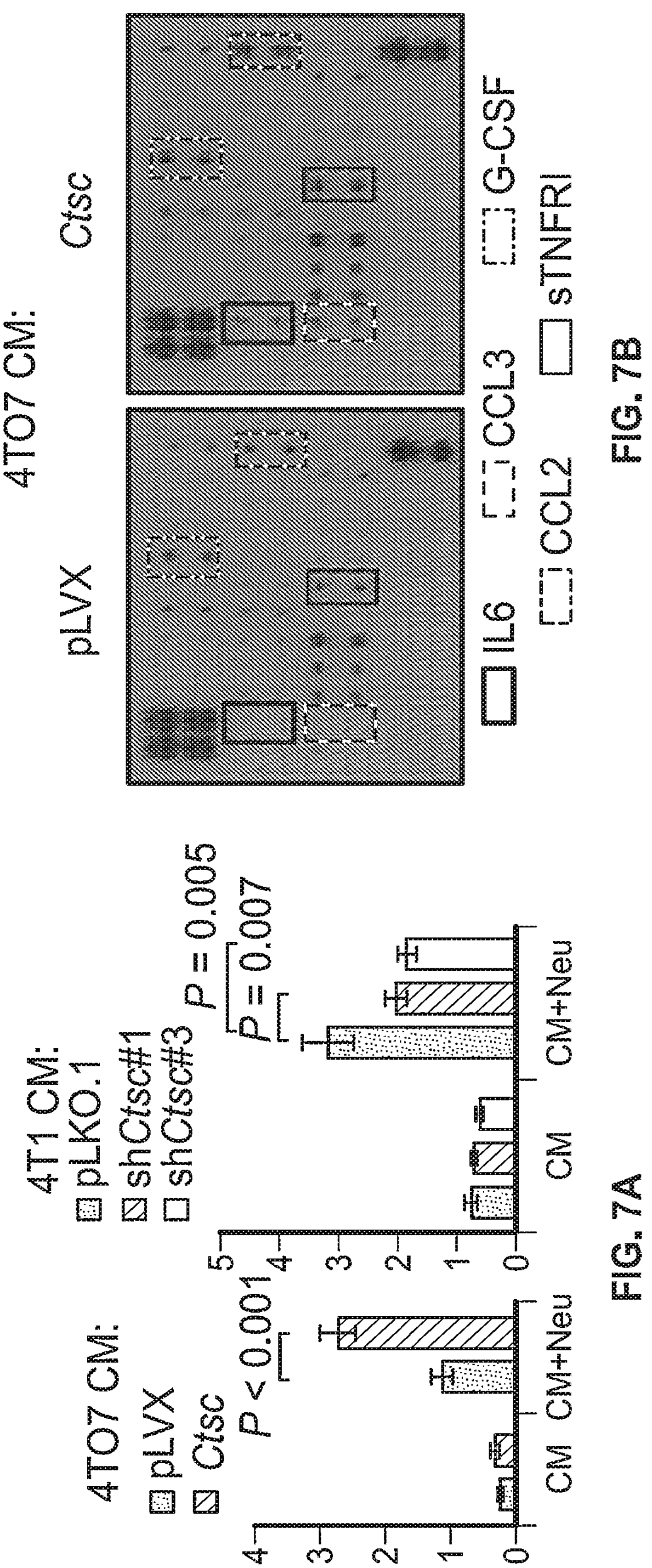
FIGS. 7A-B show the effects of overexpression or reduction of CTSC on neutrophil recruitment in controlled medium. The images of FIG. 7B show that each of IL-6, CCL2, CCL3, G-CSF, and TNFR1 are upregulated in neutrophils that are pre-treated with CTSC overexpressing 4T07 cancer cells. The Western blot image of FIG. 7C shows that, of a set of six neutrophil-derived serine proteases, only PR3 is expressed on the neutrophil cytoplasmic membrane.

Example 7: CTSC Enhances Recruitment of Neutrophils by Regulating the PR3-IL-1β-NF-κB Axis The mechanism of neutrophil recruitment by CTSC is investigated. Both CTSC overexpression (4T07 cells) and CTSC reduction (4T1 cells) have no effect on the recruitment of neutrophils by cancer cells in the conditioned medium (CM) (FIG. 7A). However, when neutrophils are pre-treated with the 4T07 CTSC-containing cancer cell conditioned medium, the neutrophil culture medium is able to attract more neutrophils relative to control 4T07 conditioned medium without CTSC overexpressed (FIG. 7A, left panel).

Cytokine array analysis of neutrophil media pre-treated with CTSC overexpressed 4T07 reveals that, after 12 h incubation, chemotactic factors interlukin-6 (IL-6), C—C motif chemokine ligands 2 and 3 (CCL2 and CCL3), granulocyte colony-stimulating factor (G-CSF), and soluble tumor necrosis factor receptor I (TNFRI) are all upregulated when compared to pre-treatment with control 4T07 (FIG. 7B). As shown FIG. 7B, upregulation of IL-6 and CCL3 is most pronounced.

Figure 7E:
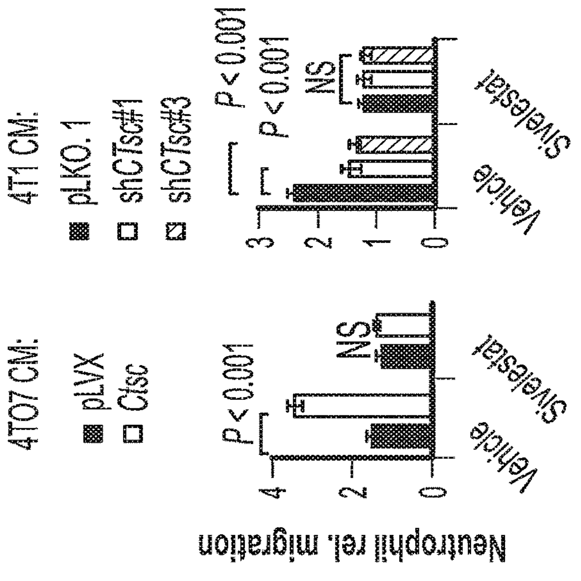
FIG. 7E-G show that Silvelestat reduces the migration of murine neutrophils pre-treated with the conditioned medium of 4T07 cells overexpressing CTSC (E), and decreases neutrophil aggregation around SCP28 cancer cells overexpressing CTSC (F-G).
Figure 7D:
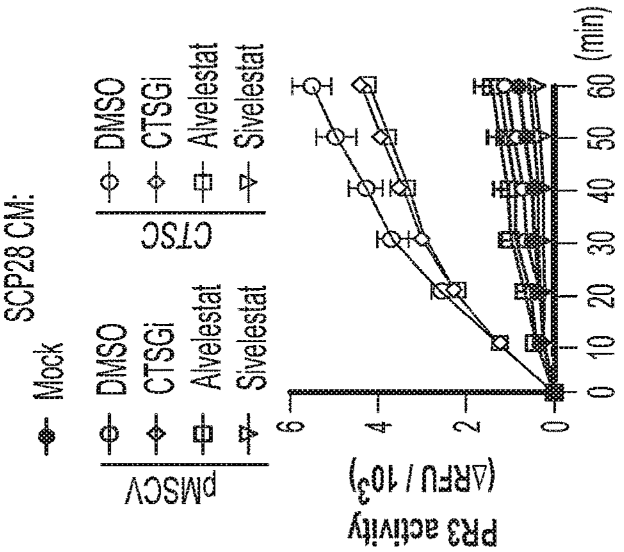
FIG. 7D shows that PR3 activity of human neutrophils cultured with the CM of SCP28 cancer cells overexpressing CTSC is reduced upon treatment with an inhibitor of PR3 (Silvelestat).
Figure 7C:
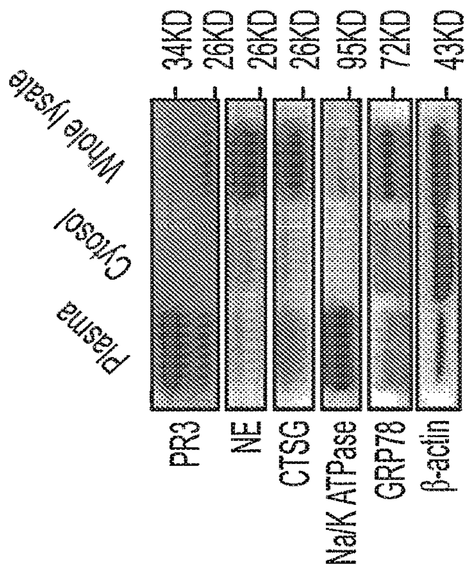
FIG. 7 demonstrates that neutrophil recruitment by CTSC is enhanced via PR3-IL-1b-NF-kB pathway regulation.
FIG. 7H shows that Silvelestat reduces IL-1b levels of neutrophils pre-treated with the conditioned medium of SCP28 cancer cells with CTSC, while an NF-κB inhibitor (BAY 11-7082) does not.
As seen in FIG. 7I-J, when mice transplanted with CTSC-overexpressing AT3 cancer cells are treated with an IL-1b-blocking antibody, lung metastasis (I) and pulmonary surface nodule formation (J) are reduced as compared to IgG treatment.

FIG. 7C depicts the expression levels of neutrophil-derived serine proteases, PR3, NE, and CTSG, all of which are known substrates of CTSC, in various cell fractions of HL-60 derived neutrophils. Fraction markers used in this experiment are Na/K ATPase, GRP78, and β-actin. As shown in FIG. 7C, only PR3 is expressed on the cytoplasmic membrane of the HL-60 derived neutrophils, indicating that CTSC may directly regulate membrane-bound PR3 on the neutrophil cell surface.

Membrane-bound PR3 activity of human neutrophils cultured with the conditioned medium of SCP28 cancer cells overexpressing CTSC is then examined (FIG. 7D). As shown in FIG. 7D, treatment with either CTSGi, a CTSG inhibitor, or Alvelestat, a NE inhibitor, has no effect on upregulated PR3 activity resulting from CTSC overexpression. However, treatment with Silvelestat, a PR3 inhibitor, significantly reduces upregulated PR3 activity.

As shown in the left panel of FIG. 7E, the migration of murine neutrophils recruited by media of neutrophils pre-treated with the conditioned medium of 4T07 (with CTSC overexpressed) cancer cell is significantly reduced following treatment with Silvelestat.

Figure 7F:
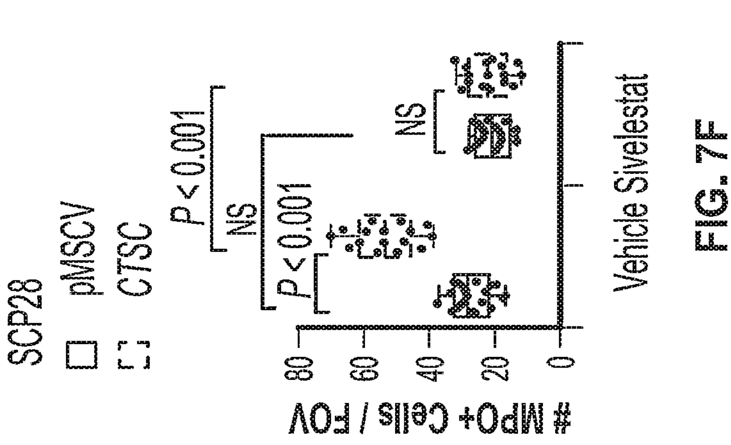
Figure 7G:
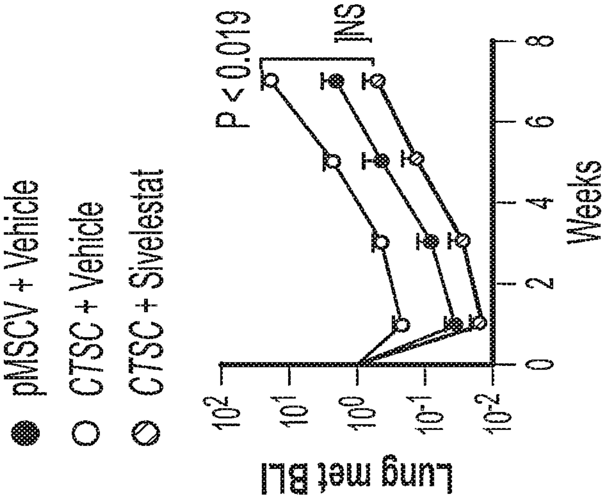

The number of myeloperoxidase-positive neutrophils around $GFP^+$ cancer cells in the lungs of mice 72 h after injection with CTSC-overexpressed SCP28 is quantified by immunostaining of the lung tissue. While neutrophil aggregation around cancer cells is increased relative to control, further treatment with Silvelestat decreases the amount of neutrophil aggregation (FIG. 7F). These effects are shown to persist through 7 weeks post-injection (FIG. 7G). The data provided in FIGS. 7D-G suggest that CTSC regulates neutrophils through PR3, and not CTSG or NE.

Figure 7H:
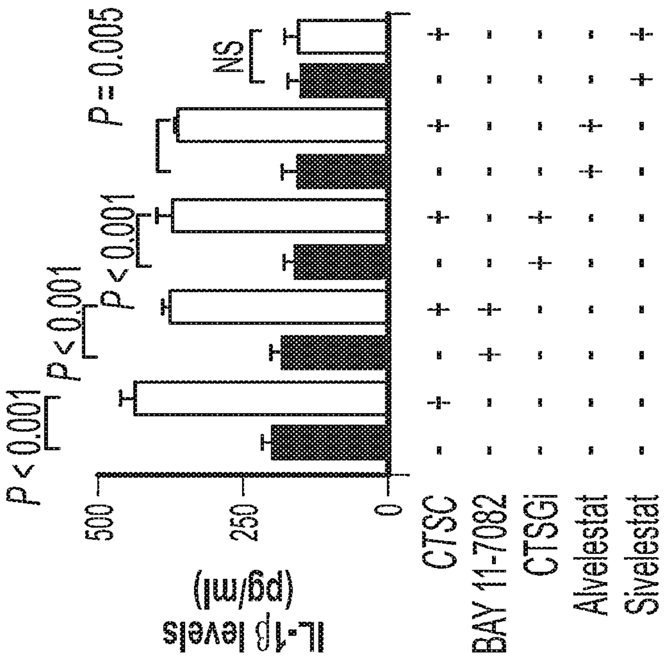

FIG. 7H shows the IL-1β secretion of human neutrophils that are pre-treated with the conditioned medium of SCP28 cancer cells with and without CTSC overexpression in combination with Silvelestat, Alvelestat, CTSGi, or BAY 11-7082, an NF-κB inhibitor. Of the four inhibitors, only PR3 inhibitor Silvelestat reduces IL-1β levels of neutrophils pre-treated with the conditioned medium of SCP28 cancer cells with CTSC overexpressed (CTSC+, Silvestat+). That treatment with BAY 11-7082 does not reduce IL-1β levels suggests that the regulation of IL-1β by CTSC in neutrophils is independent of the inflammasome pathway.

Figure 7J:
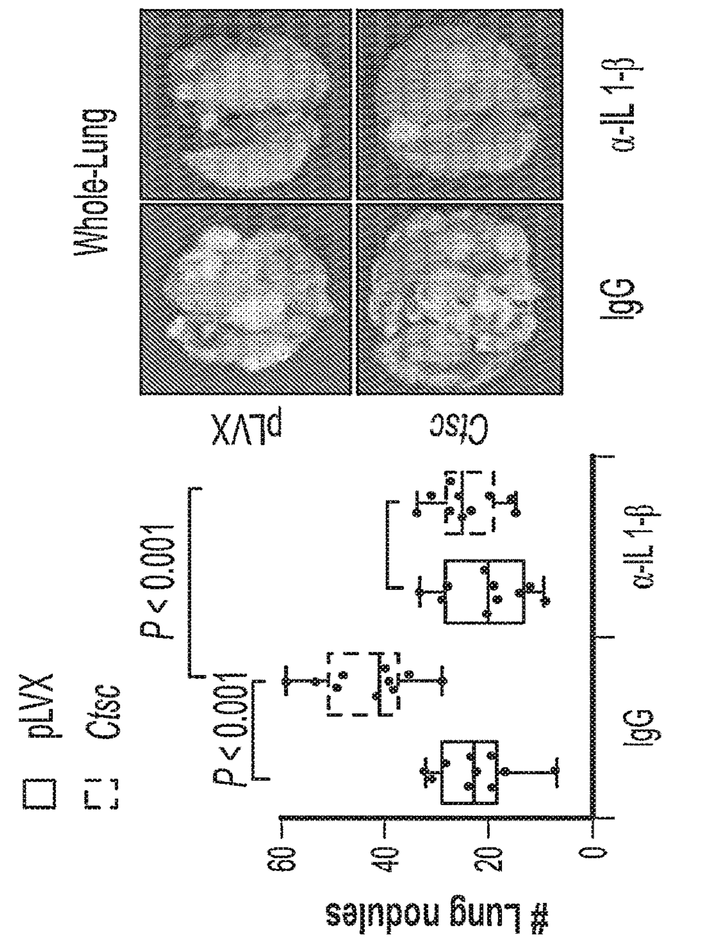
Figure 7I:
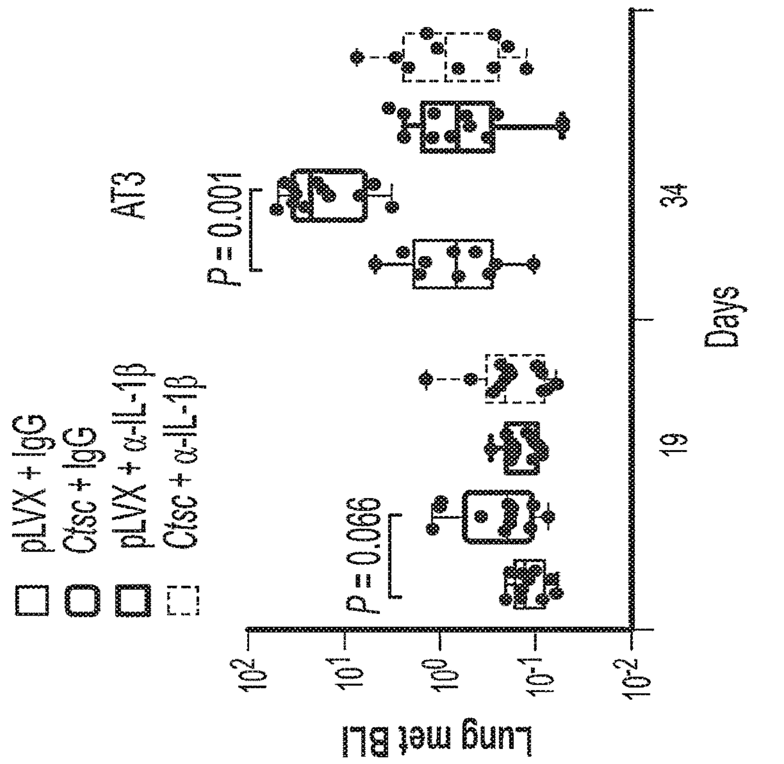

The role of IL-1β in CTSC-mediated lung metastasis is further validated by experiments in mice having undergone orthotopic transplantation of CTSC-overexpressing AT3 cancer cells. Further treatment of such mice with an IL-1β-blocking antibody reduces lung metastasis at 34 days post-transplantation relative to mice treated with IgG, as evidenced by lung BLI data (FIG. 7I). Further treatment with α-IL-1β reduces the numbers of pulmonary surface nodules in the lungs of mice transplanted of CTSC-overexpressing AT3 cancer cells as compared to mice further treated with IgG (FIG. 7J).

The data provided in FIGS. 7A-J indicates that CTSC enhances neutrophil recruitment by activating neutrophil PR3 and promoting signaling by the PR3-IL-1β-NF-κB pathway.

Example 8: CTSC in Tumors Induces Neutrophils to Form Metastasis-Supporting NETs The mechanism of metastasis regulation by neutrophils recruited to metastatic niches is investigated. Immunofluorescence staining of neutrophils cultured in the conditioned medium of CTSC-overexpressed SCP28 cancer cells form extensive extracellular trap (NET) structures in the lungs, in numbers similar to those induced with phorbol-12-myristate-13-acetate (PMA) (FIG. 8A). Conversely, neutrophils cultured in the conditioned medium of CTSC knockdown LM2 cancer cells exhibit reduced NET formation.

Figure 8B:
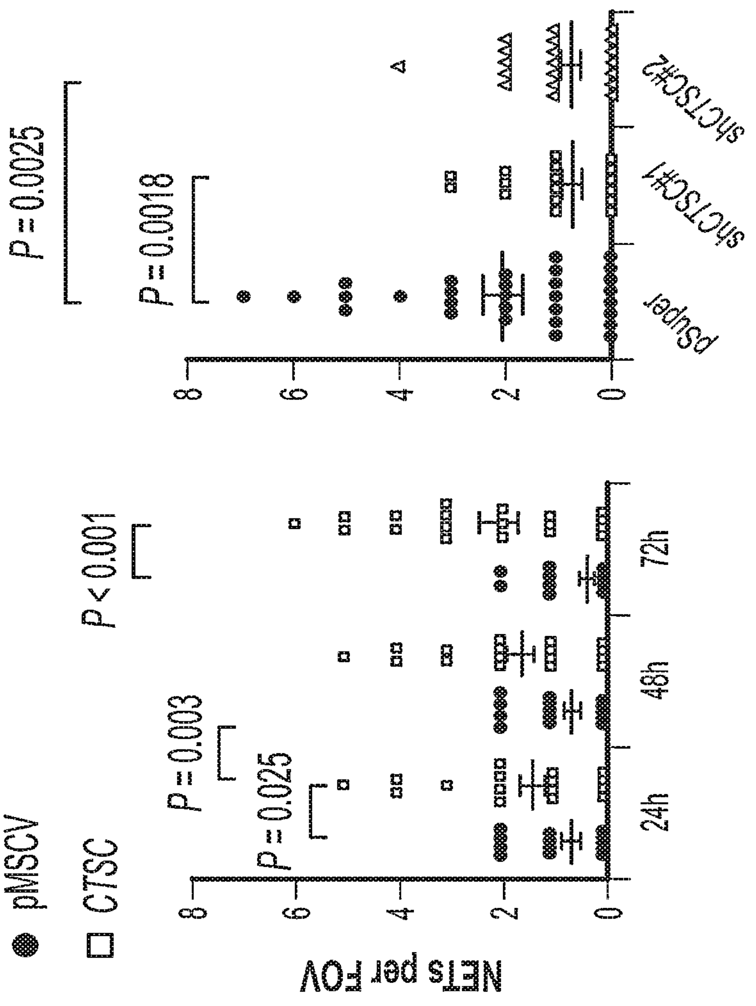
FIG. 8 suggests that tumor CTSC recruits neutrophils to induce NETosis. The IF results of FIG. 8A shows that neutrophils cultured in the conditioned medium of SCP28 cancer cells overexpressing CTSC form extensive NETs. The IF results of harvested lungs of mice show significant NET formation near to CTSC overexpressing cancer cells (SCP28) has occurred in treated mice, while there is little NET formation in proximity to cancer cells with reduced CTSC expression (LM2) (FIG. 8B).
FIG. 8C compares ROS levels in murine neutrophils pre-treated with the conditioned medium of 4T07 cancer cells with and without added Silvelestat.
FIG. 8D shows increased p38 phosphorylation in murine neutrophils pre-treated with 4T1 conditioned medium and/or recombinant human active PR3 with added rhPR3, regardless of CTSC expression level. ROS production is increased in murine neutrophils pre-treated with 4T07 cells overexpressing CTSC, while addition of a p38 inhibitor (SB203580) reverses this effect (FIG. 8E). Treatment of murine neutrophils cultured in 4T07 or 4T1 conditioned media with either Silvelestat (to inhibit PR3) or DNase I (to digest NETs) blocks NET formation induced by CTSC (FIG. 8F), and the same effect is seen in mice injected with SCP28 cells overexpressing CTSC which are further treated with Silvelestat or DNase I (FIG. 8G).
FIG. 8H shows that rmTSP-1 fails to block spheroid growth of 4T07 cancer cells cultured in neutrophil medium, while further addition of a-IL6 and/or DNase I do suppress spheroid growth to varying degrees.
Figure 8A:
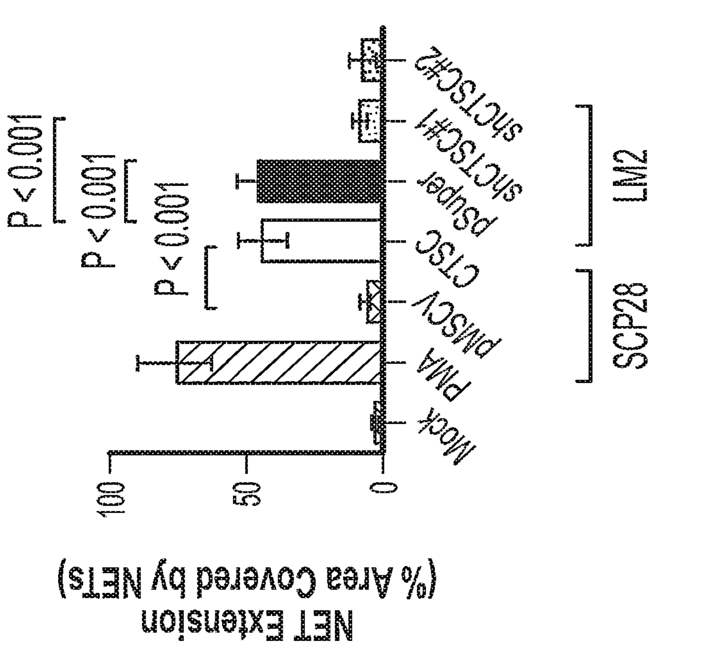

IF analysis of harvested lungs show increased NETs in proximity $GFP^+$ SCP28 cancer cells overexpressing CTSC as compared to control, when harvesting is conducted at 24 h, 48 h, and 72 h post-injection, while the opposite effect is observed in CTSC knocked-down LM2 cancer cells in the lungs (FIG. 8B).

Figure 8E:
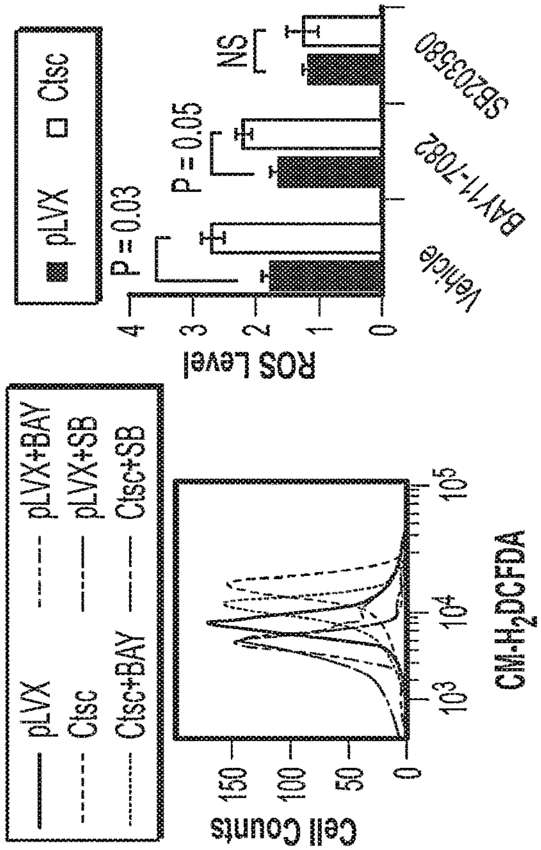

The release of reactive oxygen species (ROS) by neutrophils is known to induce NET formation. See Kolackzkowska et al., "Molecular Mechanisms of NET formation and degradation revealed by intravital imaging in the liver vasculature," *Nat. Commum.* 6, 6673 (2015). ROS analysis of murine neutrophils pre-treated with the conditioned medium of 4T07 cancer cells shows increased ROS production resulting from CTSC overexpression, while the addition of Silvelestat blocks ROS production when CTSC is overexpressed (FIG. 8C).

Figure 8D:
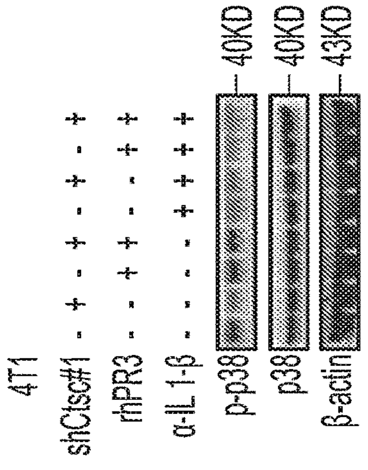
Figure 8C:
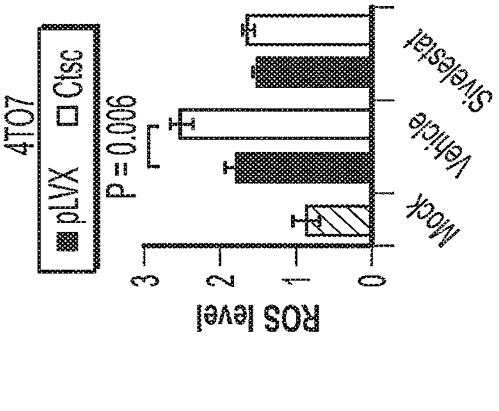

As shown in FIG. 8D, murine neutrophils pre-treated with 4T1 conditioned medium and/or recombinant human active PR3 show increased p38 phosphorylation in the presence of rhPR3, regardless of whether CTSC had been knocked down in the 4T1 cells. However, this effect is blocked by adding an IL-1β-blocking antibody.

ROS analysis of murine neutrophils pre-treated with 4T07 conditioned medium show increased ROS production results from CTSC overexpression (FIG. 8E). The addition of NF-κB inhibitor BAY 11-7082 has no effect on ROS levels, suggesting that NF-κB signaling is not involved in ROS production of neutrophils. On the other hand, the addition of p38 inhibitor SB203580 significantly reduces ROS levels, indicating that the p38 mitogen-activated protein kinase (MAPK) pathway is involved in neutrophil ROS production and NETosis.

Figure 8G:
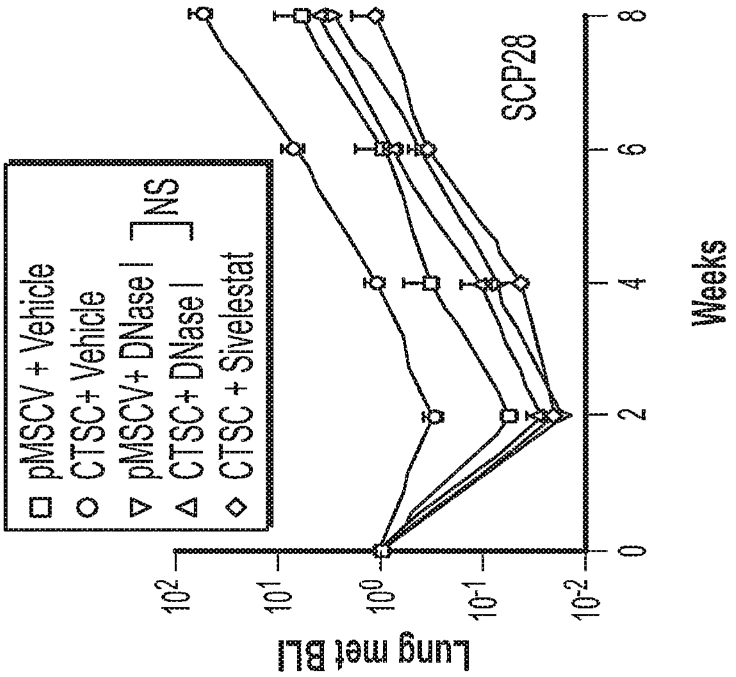
Figure 8F:
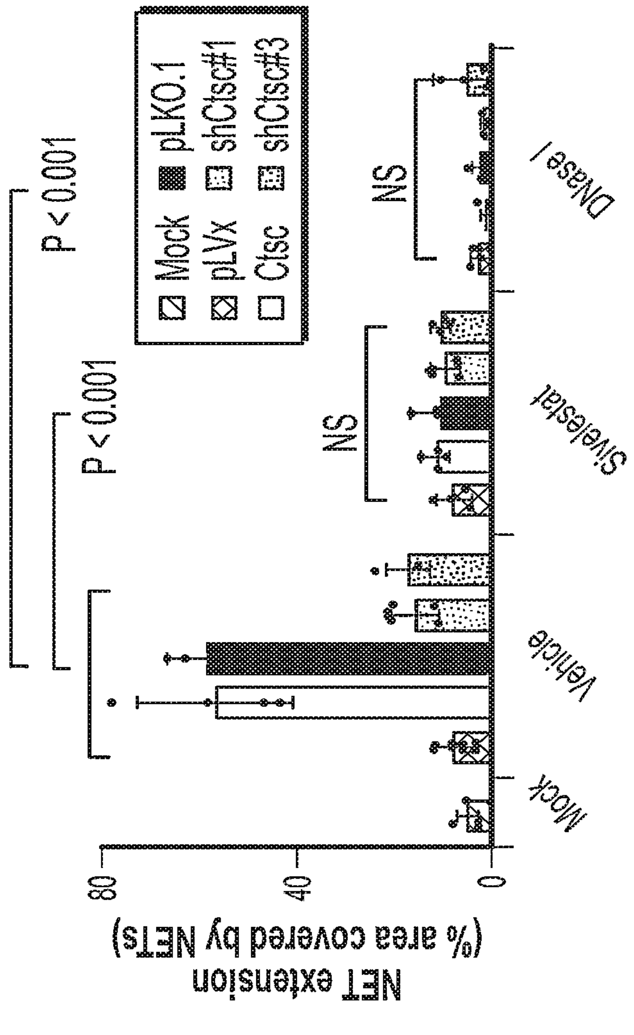

As shown in FIG. 8F, treating murine neutrophils cultured in 4T07 or 4T1 conditioned media with either Silvelestat (to inhibit PR3) or DNase I (to digest NETs) blocks the ability of CTSC to induce NET formation, as evidenced by the low percentage area covered by NETs. Moreover, lung metastasis in mice having been injected with SCP28 cells overexpressing CTSC is suppressed by further treatment of either Silvelestat or DNase I for up to 8 weeks post-injection, as evidenced by the BLI results provided in FIG. 8G.

Figure 8I:
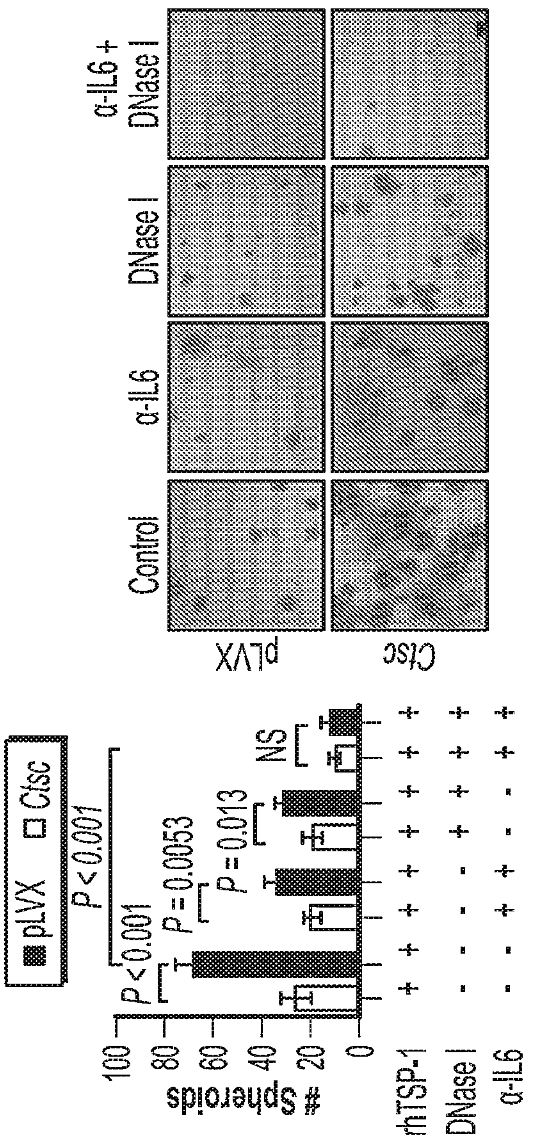
Figure 8H:
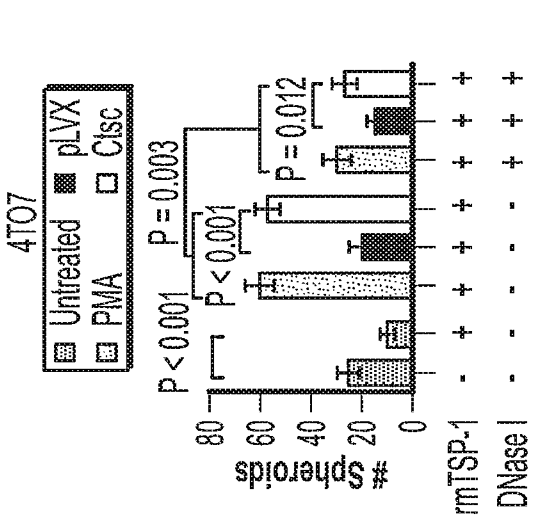

Addition of recombinant murine TSP-1 (rmTSP-1), a metastasis-suppressive ECM protein, is unable to block spheroid growth of 4T07 cancer cells cultured in neutrophil medium pre-treated with PMA (FIG. 8H). Similarly, addition of rmTSP-1 does not block spheroid growth in CTSC overexpressing 4T07 conditioned medium. However, further treatment with DNase I curtails, but does not abolish, spheroid growth in each case.

When both rmTSP-1 and an IL6-blocking antibody are added to CTSC overexpressing 4T07 conditioned medium, spheroid growth is inhibited (FIG. 8I, left panel). Spheroid growth is further inhibited the addition of DNase I (FIG. 8I, left panel). The inhibitory effects of α-IL6, DNase I, and a combination thereof, on spheroid formation can be seen in the images provided in FIG. 8I.

Viewed as a whole, the data provided in FIGS. 8A-I demonstrates that CTSC induces NETosis in tumors by activating p38 and increasing ROS in neutrophils, and the resultant NETs support metastatic growth in tumor cells.

Example 9: Analysis of Human Breast Tumor Samples for Neutrophil Infiltration and NETs The clinical relevance of NET formation to lung metastasis of human breast cancer is investigated.

Figure 9A:
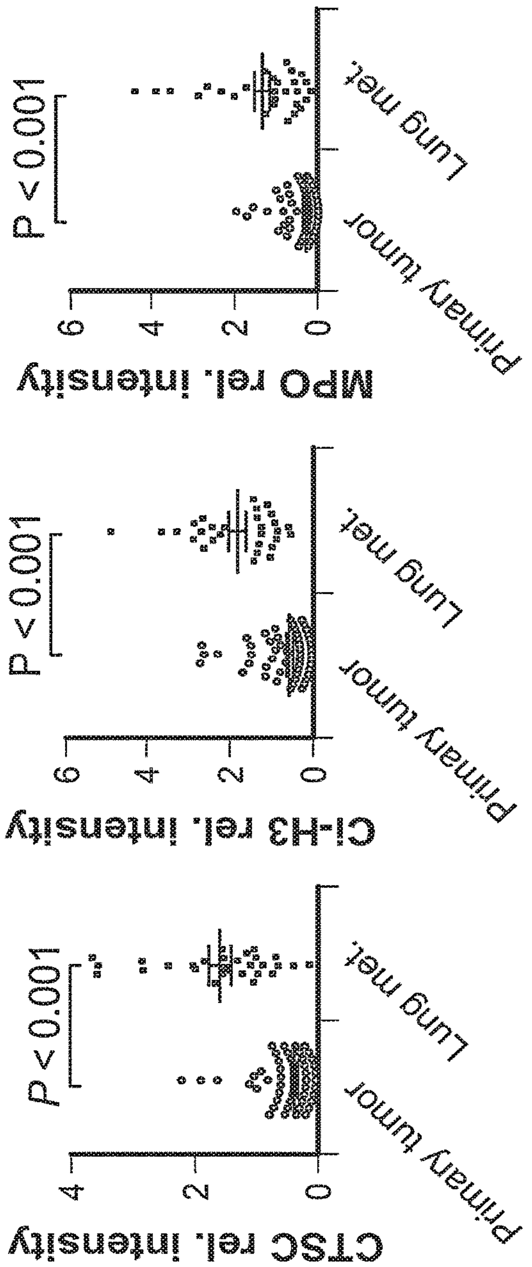
FIG. 9A demonstrates that CTSC expression, numbers of NETs, and neutrophil infiltration are higher in lung metastasis samples versus the primary tumor samples.
Figure 9B:
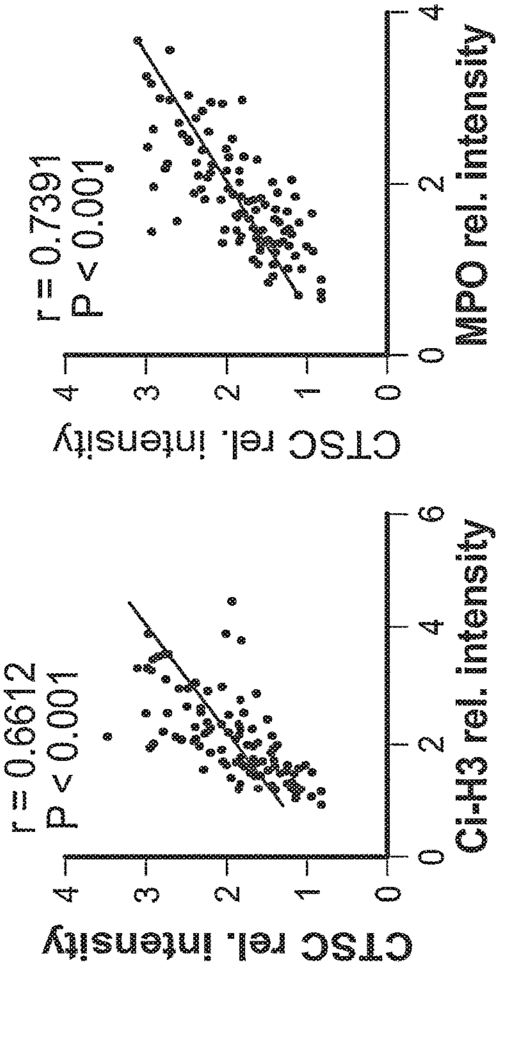
FIG. 9B shows that CTSC expression level strongly correlates to NET formation and neutrophil infiltration in both primary tumors and lung metastases.

IF analyses of a set of 74 human primary breast tumors and a set of 29 lung metastases show that expression of CTSC, formation of NETs, and neutrophil infiltration is significantly higher in lung metastasis samples relative to the primary tumor samples (FIG. 9A). Further, CTSC expression level strongly correlates to NET formation (FIG. 9B, left panel) and neutrophil infiltration (FIG. 9B, right panel) in both primary tumors and lung metastases.

Figure 9D:
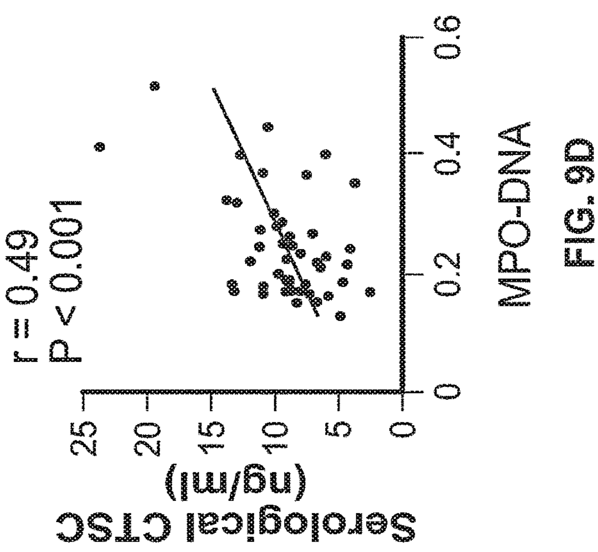
FIG. 9D shows that serological CTSC expression level strongly correlates with the circulating NET level in serum when primary tumors and lung metastases are considered together.
Figure 9C:
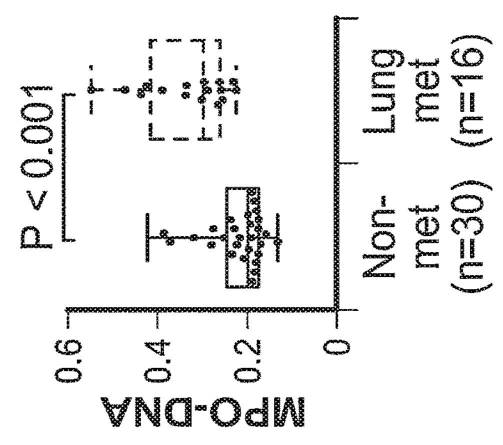
FIG. 9C shows that circulating NET levels are higher in lung metastatic tumors than in non-metastatic tumors.

FIG. 9C shows that circulating NET levels are higher in lung metastatic tumors than in non-metastatic tumors, and FIG. 9D shows that serological CTSC expression level strongly correlates with the circulating NET level in serum when both primary tumors and lung metastases are considered together.

Figure 9E:
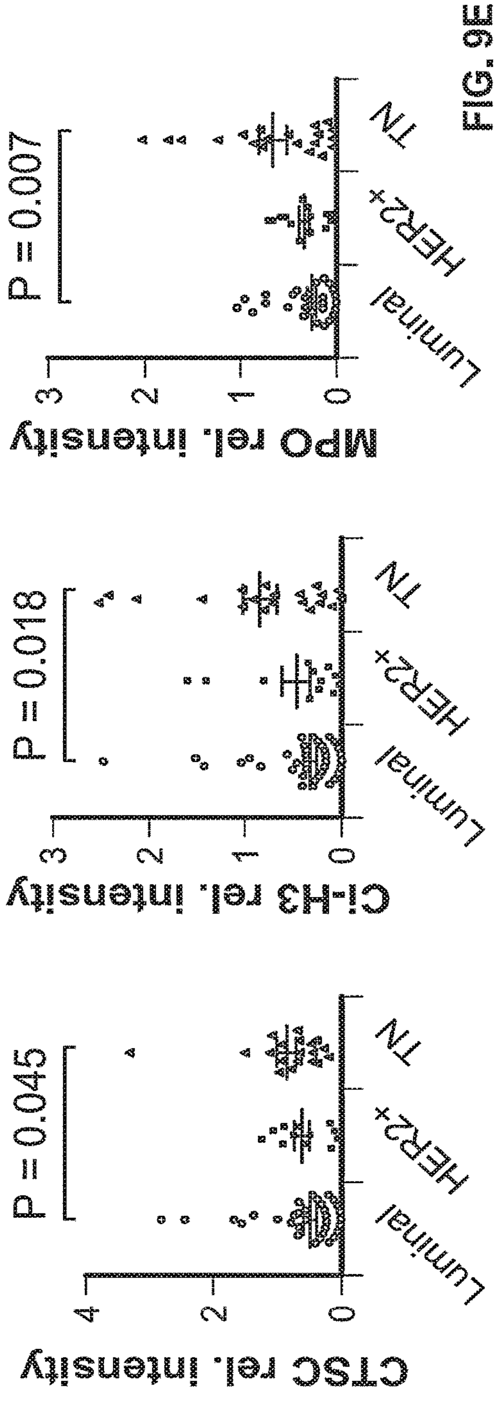
FIG. 9E shows that higher levels of CTSC, NETosis, and neutrophil migration are observed in three different clinical breast cancer subtypes.

Higher levels of CTSC expression, NET formation, and neutrophil migration is also observed in IF analyses of three different breast cancer subtypes (FIG. 9E).

The data provided in FIGS. 9A-E shows that in clinical samples, CTSC expression is linked to neutrophil infiltration and NET formation in lung metastasis of breast cancer.

Figure 10C:
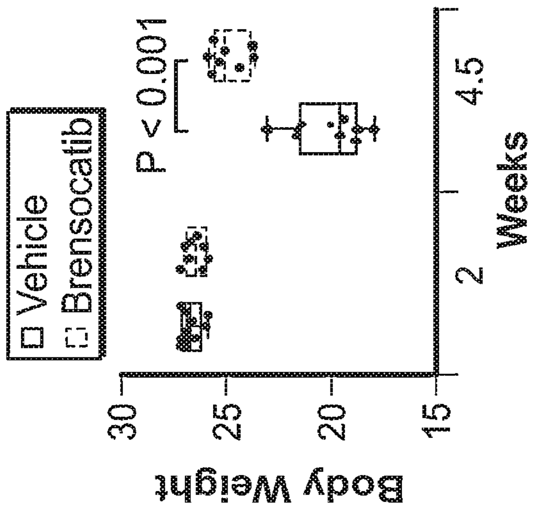
FIG. 10 shows that CTSC inhibitor brensocatib inhibits lung metastasis of breast cancer.
FIG. 10A shows tumor volume vs. time obtained by observing tumor cell growth after the administration of brensocatib seven days after injecting CTSC-reduced 4T1 cells in mice.
FIG. 10F shows tumor sphere formation of 4T1 breast cancer cells cultured in medium of neutrophils pre-treated with CM of 4T1 (CM), or brensocatib. Similar effects are observed in mice orthotopically injected with CTSC-overexpressing AT3 cancer cells and then treated with brensocatib (FIGS. 10G-J). Brensocatib treatment also results in reduced circulating levels of IL-1b (FIG. 10K).
Figure 10B:
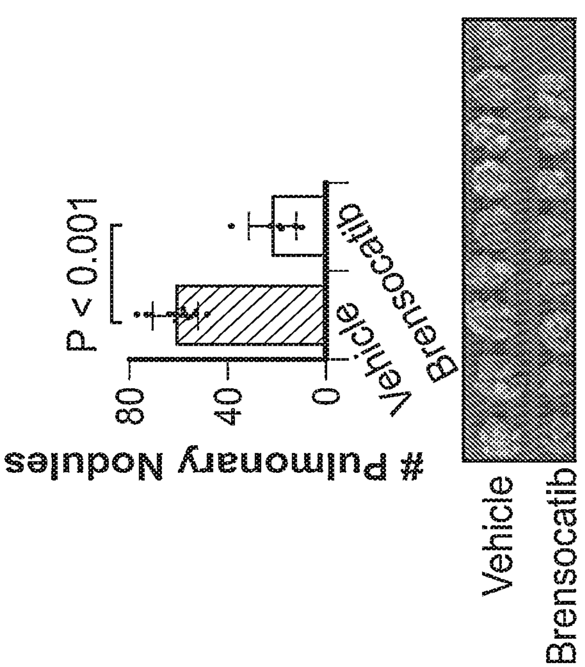

Example 10: CTSC Inhibitor Brensocatib Inhibits Metastasis of Breast Cancer in the Lung The use of CTSC inhibitors to treat lung metastasis of breast cancer is investigated. Brensocatib (also known as AZD7986 or INS1007) is a CTSC-specific inhibitor used for treating Non-Cystic Fibrosis Bronchiectasis, and has currently entered Phase II clinical trials. See Doyle et aL, "Discovery of second generation reversible covalent DPP1 inhibitors leading to an oxazepane amidoacetonitrile based clinical candidate (AZD7986)," *J. Med. Chem.* 59:9457-9472 (2016). Brensocatib is administered to mice 7 days after the introduction of 4T1 cells via fat pad injection. A vehicle control group is also provided. Graphical data for change in tumor volume over time, numbers of pulmonary nodules formed, changes in mouse weight over time, and mouse survival rates, as well as the statistical diagram of the number of NETs in the lesions, are shown in FIGS. 10A-E. CTSC inhibitor brensocatib also suppresses the NETs-promoted tumor sphere formation of 4T1 cells (FIG. 10F).

Figure 10A:
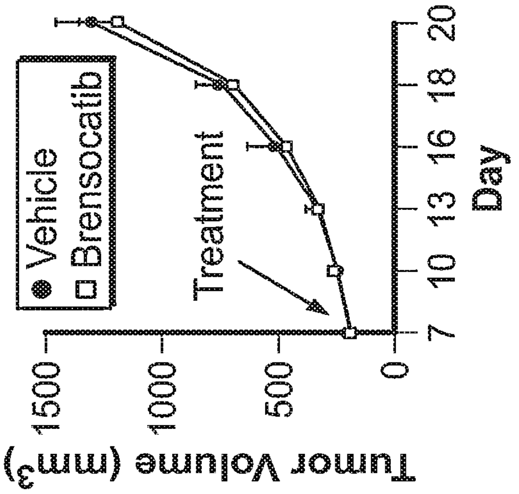

Consistent with the 4T1 CTSC-reduced phenotype, the changes of in situ tumor volume vs. time are consistent between the brensocatib administration group and the untreated control group, indicating that the administration of brensocatib does not affect primary tumor growth (FIG. 10A).

When compared to untreated mice, mice treated with brensocatib exhibit significantly reduced pulmonary nodule formation, indicating that brensocatib administration can inhibit the formation of metastatic lesions by tumor cells on the lung surface (FIG. 10B).

The body weight decrease of mice treated with brensocatib is lower than untreated mice, indicating that the brensocatib administration can mitigate weight loss resulting from lung metastasis (FIG. 10C).

Figure 10D:
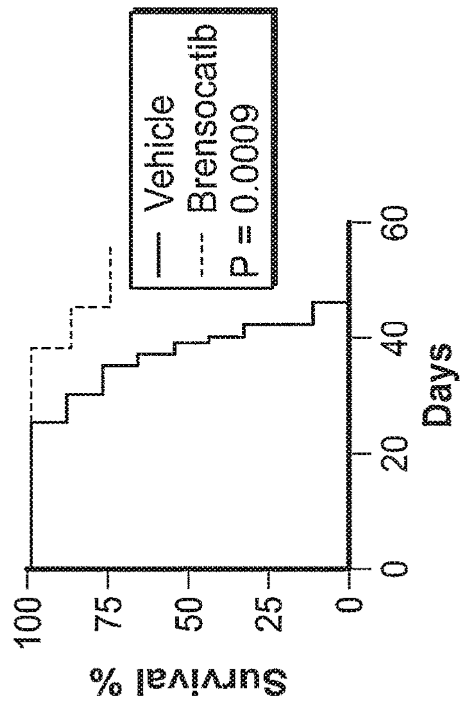

Treatment with brensocatib significantly improves the survival rate of the mice as compared to untreated mice, indicating that brensocatib administration significantly extends the survival period of the mice (FIG. 10D).

Figure 10E:
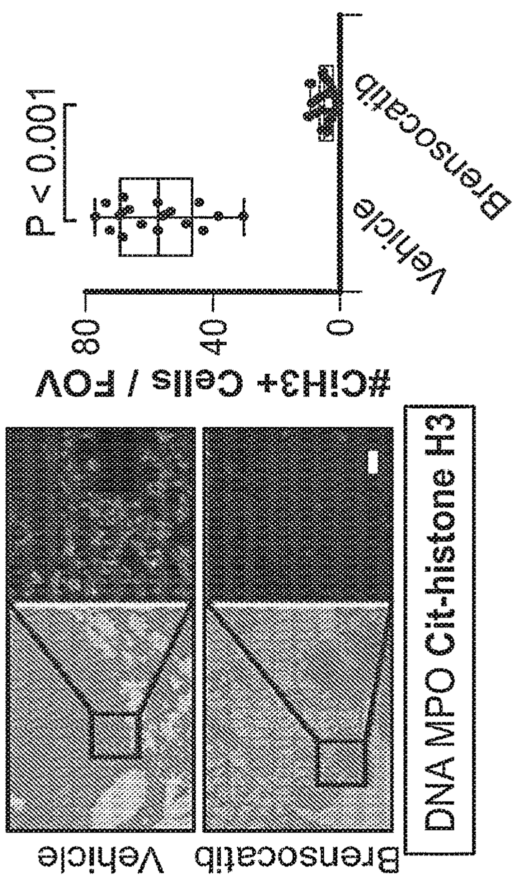
Figure 10F:
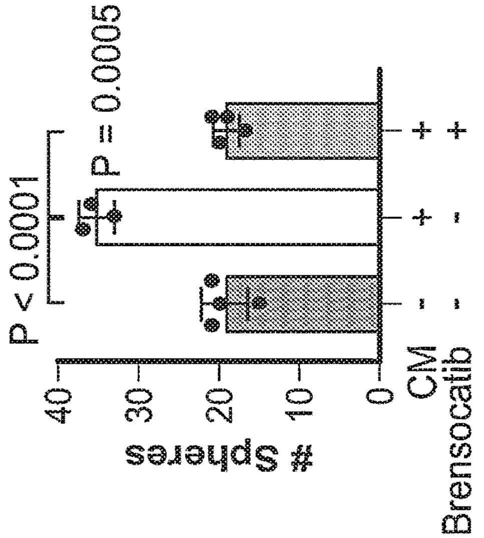

FIG. 10E shows that neutrophil infiltration in the pulmonary lesions of mice treated with brensocatib is reduced relative to untreated mice, indicating that the brensocatib administration significantly inhibits the neutrophil infiltration and formation of NETs in the lung metastatic lesions.

Figure 10H:
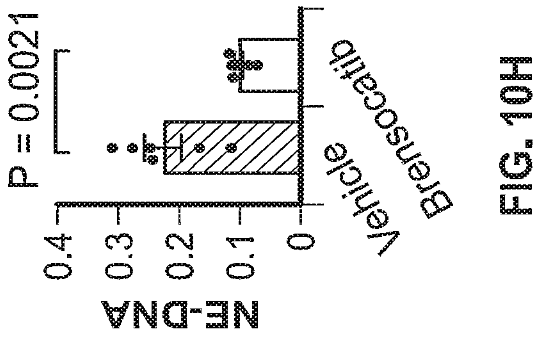
Figure 10G:
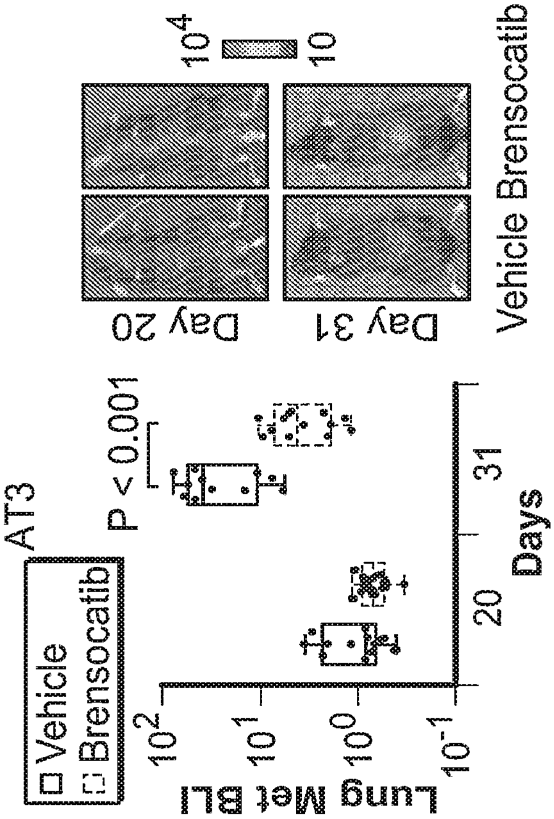
Figure 10I:
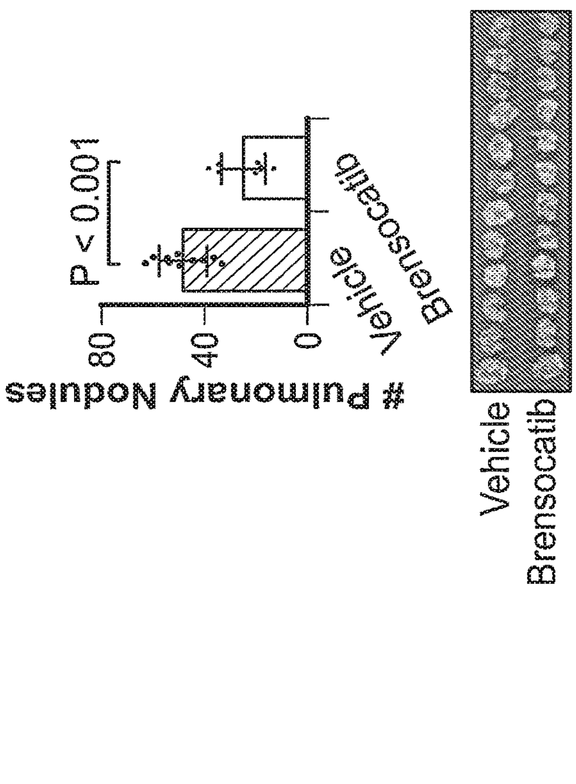
Figure 10J:
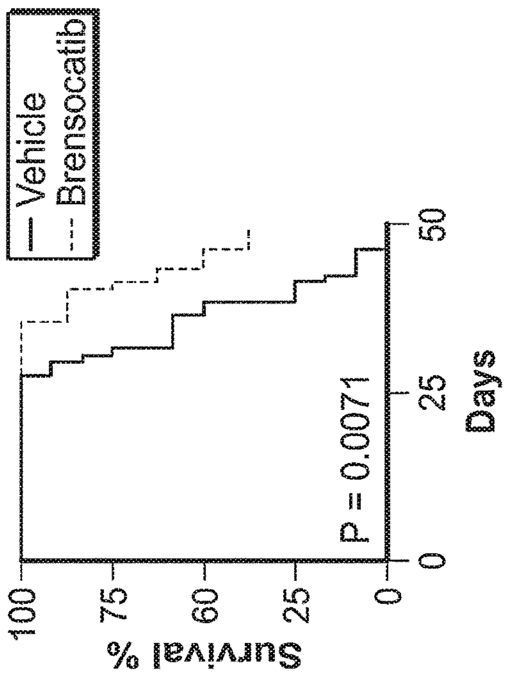
Figure 10K:
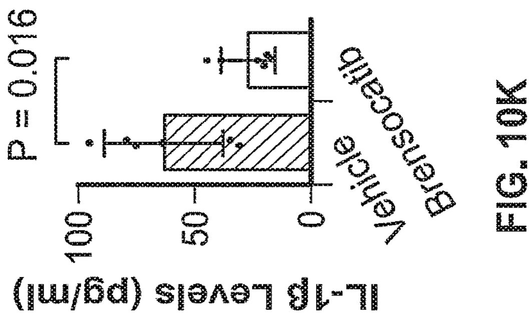

FIG. 10F shows tumor sphere formation of 4T1 breast cancer cells cultured in medium of neutrophils pre-treated with CM of 4T1 is suppressed by brensocatib as compared to untreated control group, indicating that CTSC inhibitor brensocatib suppresses the NETs-promoted tumor sphere formation of breast cancer cells Similar effects are seen in treatment of mice with brensocatib after orthotopic injection of CTSC-overexpressing AT3 cancer cells. Decreases in lung metatheses, circulating NETs, neutrophil migration, and lung metastatic nodule formation resulting from brensocatib treatment are shown in FIGS. 10G-I. Also, a significant increase in survival rate and a decrease in circulating levels of IL-1β is observed in brensocatib-treated mice (FIGS. 10J-K).

All of the data provided above supports CTSC as a potential new target for clinical treatment of lung metastasis of breast cancer. Mechanistically, CTSC promotes lung metastasis of breast cancer through increased neutrophil infiltration and increased numbers of NETs at lesion sites, thereby priming the tumor microenvironment for promoting the lung metastasis of breast cancer. However, CTSC inhibitor brensocatib effectively inhibits neutrophil infiltration and reduces the formation of NETs at lesion sites, thereby inhibiting the lung metastasis of breast cancer in mice.

Example 11: CTSC Inhibitor Brensocatib Inhibits Neutrophil Recruitment, Formation of NETs and Tumor Sphere Formation by Various Types of Metastatic Cancer Cells In view of the promoting effect of CTSC upregulation on neutrophil recruitment and formation of NETs in tumor metastases, as well as the beneficial effects of a CTSC inhibitor (brensocatib) on neutrophil functions, the use of CTSC inhibitors in other diseases of tumor metastasis (including metastasis of breast cancer to liver and bone, and metastasis of lung cancer to bone) is considered.

The CTSC protein secretion level in tumor cells with different capabilities of metastasis to various target organs (including metastasis of breast cancer to liver, bone and metastasis of lung cancer to bone) is examined. In general, CTSC expression levels are increased in highly metastatic tumor cells. Neutrophils from bone marrow are treated with conditioned media (secretions) of these cells, either with or without brensocatib. The capability of tumor secretions to attract neutrophils is then assessed with Transwell permeable cell culture chambers, and the formation of NETs is analyzed by immunofluorescence staining of NET molecular markers (MPO and citrullinated histone H3). The data from this study are shown in FIGS. 11A-J.

The capabilities of drug-treated tumor cell secretions in attracting (recruiting) neutrophils and inducing the formation of NETs are significantly weakened due to brensocatib treatment. Indeed, CTSC protein expression (FIGS. 11A-C), the formation of NETs (FIGS. 11D, F, I), and neutrophil recruitment (FIGS. 11G, J) are significantly reduced in a number of metastatic tumor cell types treated with brensocatib.

Figure 11A:
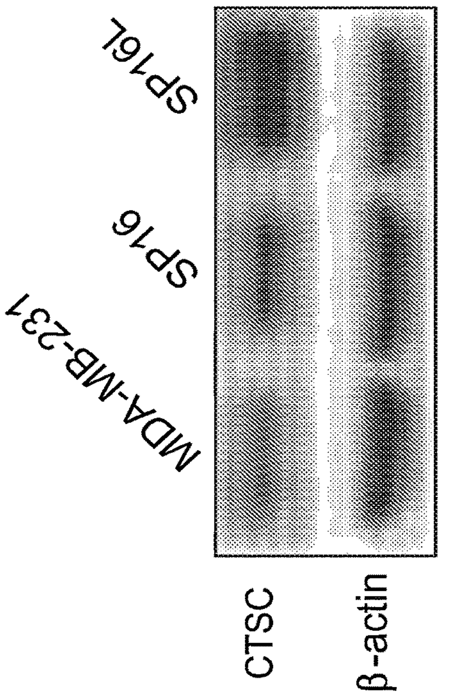
FIG. 11A shows the CTSC expression levels in weak (MDA-MB-231, 231 in short), medium (SP16), and strong (SP16L) liver-metastatic breast cancer cells.
Figure 11B:
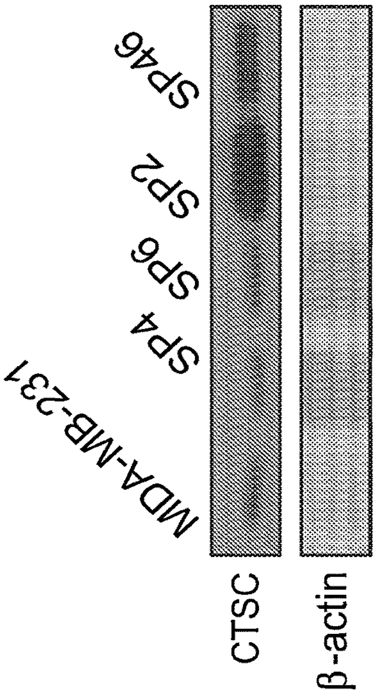
FIG. 11B shows CTSC expression levels in weak or strong bone-metastatic breast cancer cells.
Figure 11C:
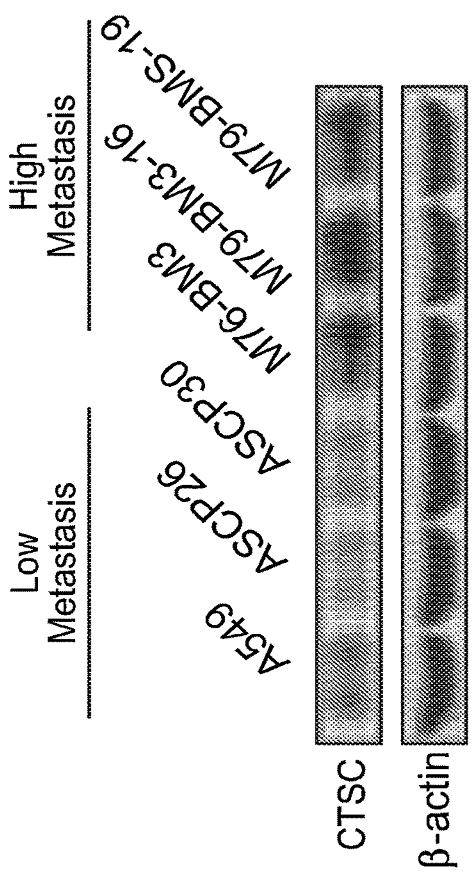
FIG. 11C shows CTSC expression levels in weak or strong bone-metastatic lung cancer cells.
Figure 11D:
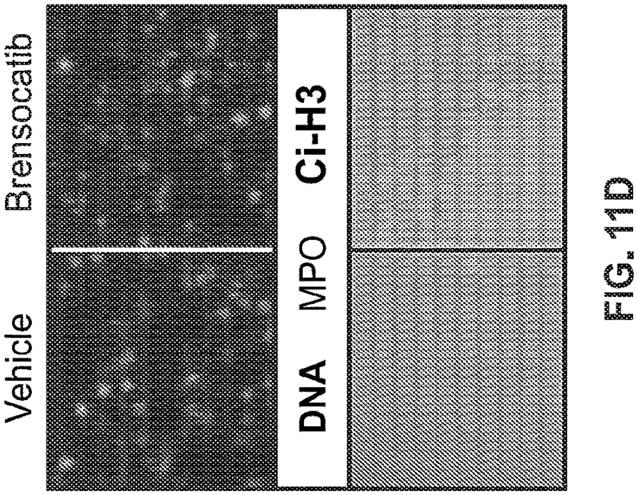
FIG. 11D shows the formation of NETs in neutrophils under stimulation by a cancer cell conditioned medium as observed through immunofluorescence staining with NETs molecular markers (myeloperoxidase (MPO); citrullinated histone H3 (Ci-H3)) after the administration of brensocatib to lung-metastatic breast cancer cell LM2-4175.
Figure 11G:
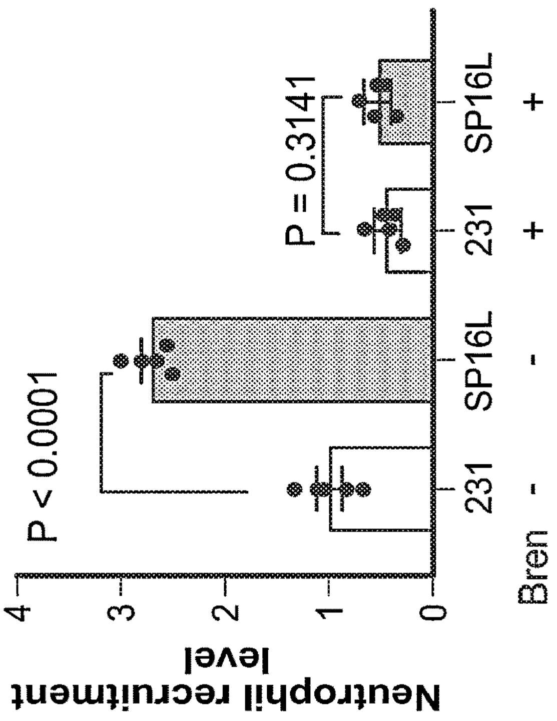
FIG. 11G analyzes neutrophil recruitment in the cancer cell conditioned medium after the administration of brensocatib to different liver-metastatic breast cancer cells.
Figure 11F:
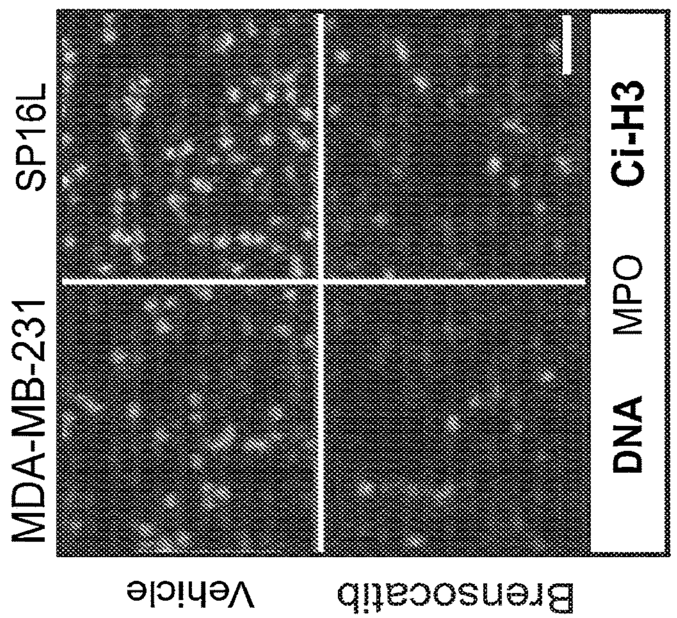
FIG. 11F shows the formation of NETs in neutrophils under stimulation by a cancer cell conditioned medium as observed through immunofluorescence staining after the administration of brensocatib to different liver-metastatic breast cancer cells.
Figure 11E:
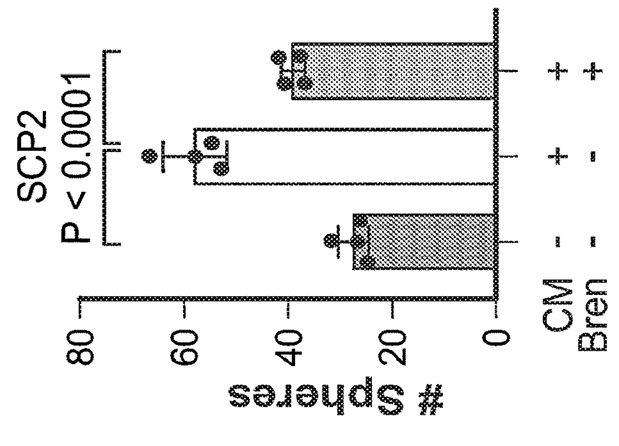
FIG. 11E shows tumor sphere formation of bone-metastatic SCP2 breast cancer cells cultured in medium of neutrophils pre-treated with SCP2 conditioned medium (CM), or Brensocatib (Bren).
Figure 11I:
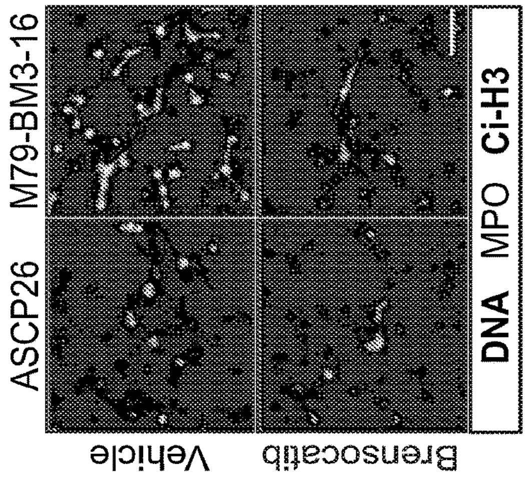
FIG. 11I shows the formation of NETs in neutrophils under stimulation by a cancer cell conditioned medium as observed through immunofluorescence staining after the administration of brensocatib to different bone-metastatic lung cancer cells.
Figure 11K:
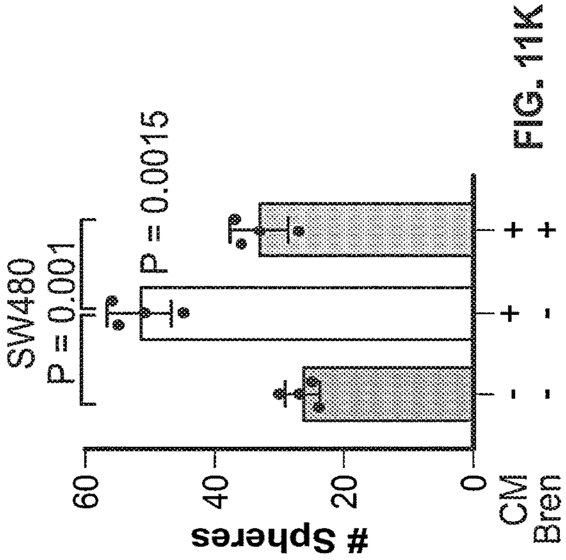
Figure 11H:
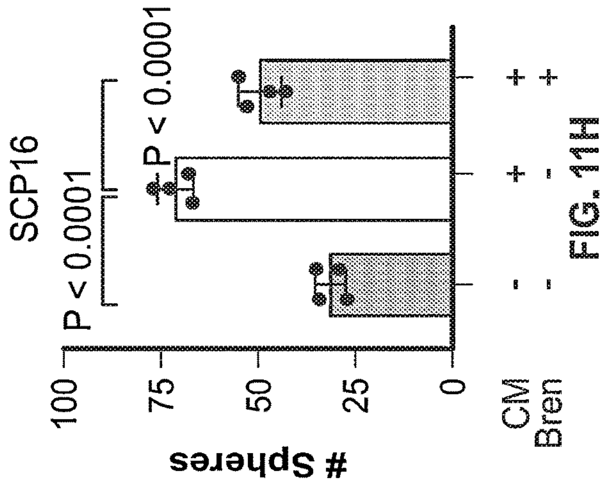
FIG. 11H shows tumor sphere formation of liver-metastatic (SCP16) breast cancer cells cultured in medium of neutrophils pre-treated with CM of SCP16 (CM), or brensocatib.
Figure 11J:
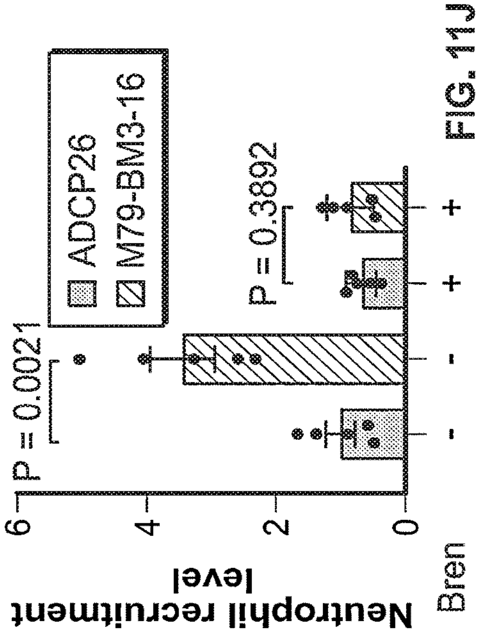
FIG. 11J analyzes neutrophil recruitment in cancer cell conditioned medium after the administration of brensocatib to different bone-metastatic lung cancer cells.
Figure 11L:
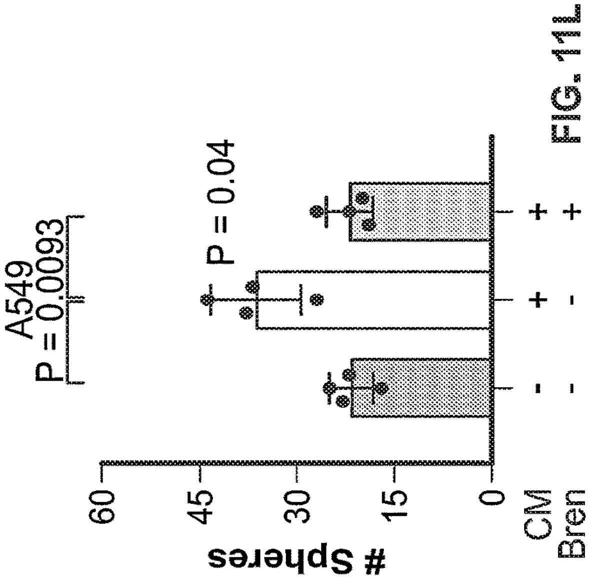
Figure 11M:
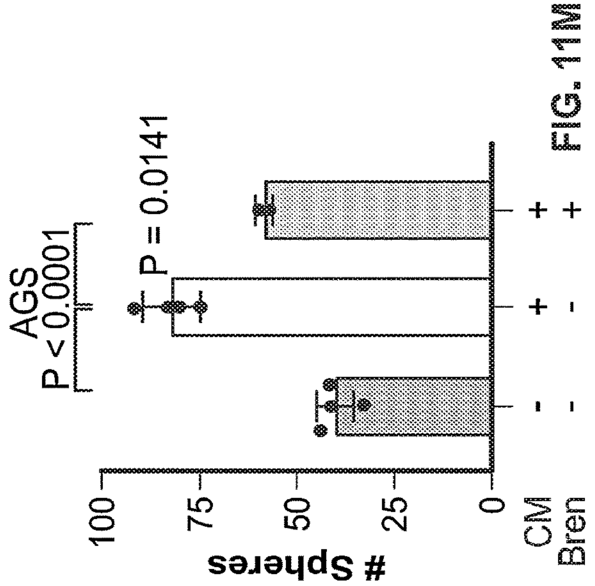
Figure 11N:
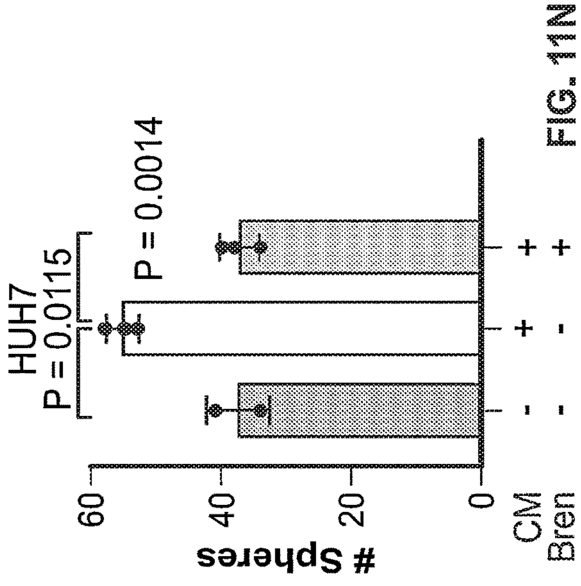
Figure 11O:
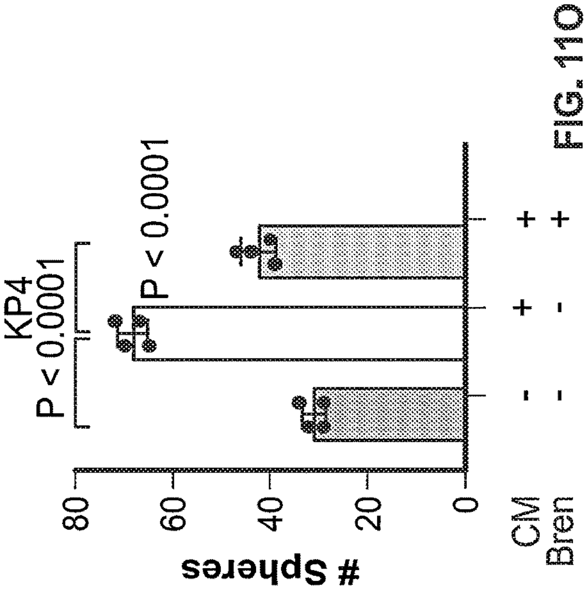

The capabilities of drug-treated neutrophils to facilitate tumor cell growth of bone- and liver-metastatic breast cancer cells in vitro are significantly weakened due to brensocatib treatment. The neutrophils are cultured with conditioned medium from the cancer cells with or without brensocatib treatment to activate NETosis, and then the neutrophil medium was used in tumor sphere formation of bone and liver-metastatic breast cancer cells to analyze the effect of neutrophil medium to facilitate tumor cell growth. The data are shown in FIG. 11E for bone-metastatic breast cancer cell SCP2 and FIG. 11H for liver-metastatic breast cancer cell SCP16.

The data provided in FIGS. 11A-J suggests that CTSC inhibitor brensocatib can reduce the neutrophil infiltration, formation of NETs and tumor cell growth in early metastatic lesions of diseases other than lung metastasis of breast cancer, such as liver metastasis of breast cancer, bone metastasis of breast cancer, and bone metastasis of lung cancer.

Example 12: CTSC Inhibitor Brensocatib Reduces NET-Promoted Tumor Sphere Formation in Various Types of Cancer In Vitro To test the therapeutic effects of brensocatib in different cancer types in vitro, the ability of brensocatib to inhibit NET-promoted tumor sphere formation is investigated. The neutrophils are cultured with conditioned medium from tumor cells of colon cancer, liver cancer, lung cancer, gastric cancer and pancreatic cancer with or without brensocatib treatment to activate NETosis, and then the neutrophil medium was used in tumor sphere formation of these cancer cells to analyze the effect of neutrophil medium to facilitate tumor cell growth. The amount of tumorsphere in each sample is then determined by imaging. The effects of brensocatib to inhibit in vitro tumor growth of these cancer types are seen in FIGS. 11K-O.

Figure 12B:
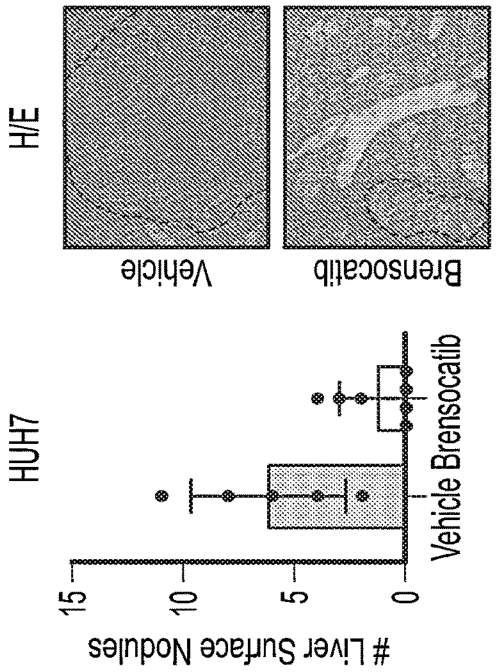
FIG. 12A-B shows that CTSC inhibitor brensocatib suppresses primary tumor growth of liver cancer cells HUH7 (A) and the formation of liver surface nodules (B).
Figure 12A:
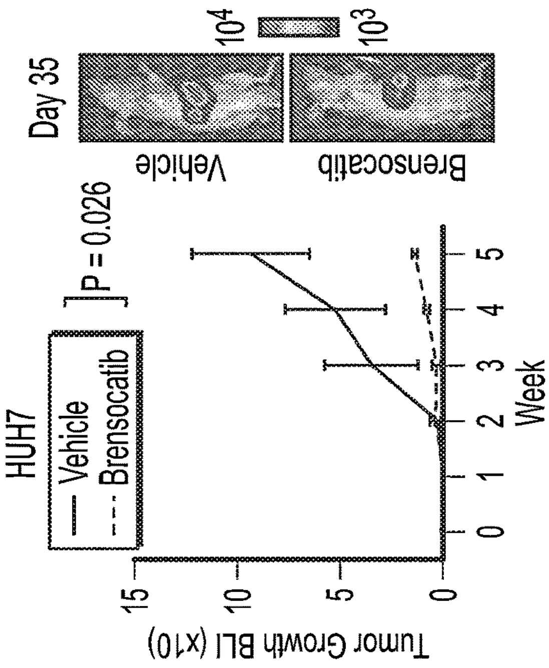
Figure 12C:
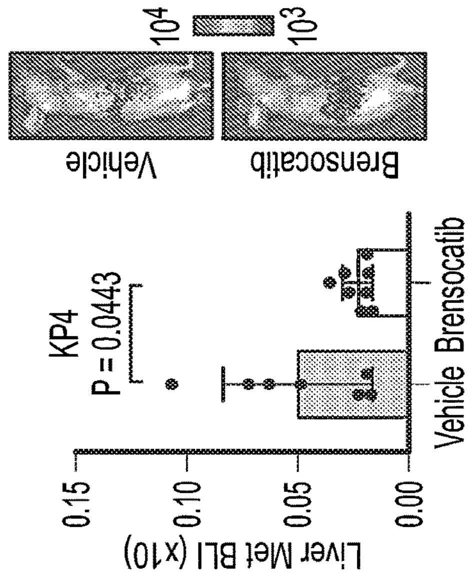
FIG. 12C shows that CTSC inhibitor brensocatib suppresses liver metastasis of pancreatic cancer cells KP4.

Example 13: CTSC Inhibitor Brensocatib Reduces Primary Tumor Growth and Metastasis in Liver In Vivo A series of mouse xenograft studies are conducted by injecting liver and pancreatic tumor cells into nude mice by spleen injection. Then the mice are treated by brensocatib, and the growth of the tumors in liver is observed. It is seen that brensocatib treatment significantly inhibits tumor growth of liver cancer cells HUH7 in liver (FIGS. 12A, B), and the metastatic growth of pancreatic cancer cells KP4 in liver (FIG. 12C).

While the present disclosure has been described with reference to particular embodiments, it will be understood by those skilled in the art that various changes may be made and equivalents may be substituted for elements thereof without departing from the scope of the present disclosure. In addition, many modifications may be made to adopt a particular situation, material, composition of matter, process, process step or steps, to the objective spirit and scope of the described invention. All such modifications are intended to be within the scope of the claims appended hereto.

Therefore, it is intended that the present disclosure not be limited to the particular embodiments disclosed as the best mode contemplated for carrying out the present disclosure, but that the present disclosure will include all embodiments falling within the scope and spirit of the appended claims.

Patents, patent applications, patent application publications, journal articles and protocols referenced herein are incorporated by reference in their entireties, for all purposes.

The invention claimed is:

1. A method of treating a metastasis of a cancer in a patient in need thereof, comprising, administering to the patient in need of treatment for a treatment period, a pharmaceutical composition comprising an effective amount of a cathepsin C (CTSC) inhibitor, wherein the administering inhibits, slows, or reverses the progression of the metastasis, and the administering reduces the formation of neutrophil extracellular traps (NETs), reduces neutrophil migration, or both at the site of metastasis during the treatment period or subsequent to the treatment period; wherein the patient in need thereof has elevated serological levels of CTSC protein prior to the administering, and wherein the administering reduces the serological levels of CTSC protein in the patient in need thereof by about 25% to about 75%;

wherein the CTSC inhibitor is brensocatib:

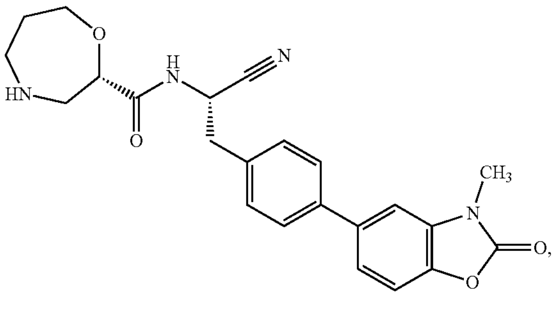 [SMILES: Cn1c(=O)oc2ccc(-c3ccc(C[C@@H](C#N)NC(=O)[C@@H]4CNCCCO4)cc3)cc21]

or a pharmaceutically acceptable salt thereof.

2. A method of treating a primary cancer in a patient in need thereof, comprising, administering to the patient in need of treatment for a treatment period, a pharmaceutical composition comprising an effective amount of a cathepsin C (CTSC) inhibitor, wherein the administering inhibits, slows, or reverses the progression of the primary cancer, and the administering reduces the formation of neutrophil extracellular traps (NETs), reduces neutrophil migration, or both in the primary cancer during the treatment period or subsequent to the treatment period; wherein the patient in need thereof has elevated serological levels of CTSC protein prior to the administering, and wherein the administering reduces the serological levels of CTSC protein in the patient in need thereof by about 25% to about 75%;

wherein the CTSC inhibitor is brensocatib:

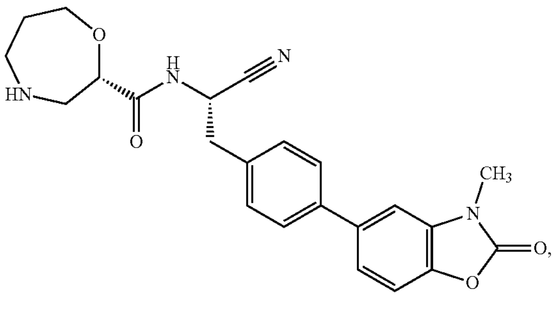 [SMILES: Cn1c(=O)oc2ccc(-c3ccc(C[C@@H](C#N)NC(=O)[C@@H]4CNCCCO4)cc3)cc21]

or a pharmaceutically acceptable salt thereof.

3. The method of claim 1, wherein the metastasis is of a breast cancer.

4. The method of claim 3, wherein the metastasis of a breast cancer is a lung metastasis of a breast cancer, liver metastasis of a breast cancer, bone metastasis of a breast cancer, or brain metastasis of a breast cancer.

5. The method of claim 3, wherein the breast cancer is luminal breast cancer, human epidermal growth factor receptor 2 (HER2) positive breast cancer, or triple-negative breast cancer.

6. The method of claim 1, wherein the metastasis is a bone metastasis of a lung cancer, a liver metastasis of a pancreatic cancer, a liver metastasis of a colon cancer, or a liver metastasis of a gastric cancer.

7. The method of claim 1, wherein the metastasis is of a pancreatic cancer, a gastric cancer, a bone cancer, a liver cancer, a stomach cancer, or a colorectal cancer.

8. The method of claim 1, wherein the administering comprises once per day oral administration of the pharmaceutical composition to the patient in need thereof during the treatment period.

9. The method of claim 1, wherein the CTSC inhibitor is present in the pharmaceutical composition in an amount of about 10 milligrams (mg) to about 70 mg.

10. The method of claim 1, wherein the treating further comprises reducing circulating levels of interleukin 1 beta (IL-1β) in the patient in need thereof during the treatment period or subsequent to the treatment period, compared to circulating levels of IL-1β of the patient in need thereof prior to the treatment period.

11. The method of claim 1, wherein the volume of the metastasis is reduced by from about 5% to about 75% during the treatment period or subsequent to the treatment period, compared to the volume of the metastasis prior to the treatment period.

12. The method of claim 1, wherein the treating further comprises reducing the expression levels of one or more proteins in the patient in need thereof, wherein the one or more proteins are selected from cathepsin C (CTSC), interleukin 6 (IL-6), C—C Motif Chemokine Ligand 3 (CCL3), and RELA (p65).

* * * * *